United States Patent [19]

Watanabe et al.

[11] Patent Number: 4,855,287
[45] Date of Patent: Aug. 8, 1989

[54] AMINOGLYCOSIDE COMPOUNDS, PROCESSES FOR PRODUCTION THEREOF, AND PHARAMACEUTICAL COMPOSITION CONTAINING THE SAME

[75] Inventors: Isamu Watanabe; Kazuhiro Kamiya, both of Higashimurayama; Takahiro Torii, Chofu; Toshihito Mori, Hagashimurayama, all of Japan

[73] Assignee: Kowa Company Ltd., Nagoya, Japan

[21] Appl. No.: 903,137

[22] Filed: Sep. 3, 1986

[30] Foreign Application Priority Data

Sep. 3, 1985 [JP] Japan .................. 60-193166

[51] Int. Cl.$^4$ ...................... C07H 15/22; A61K 31/71
[52] U.S. Cl. ........................................ 514/41; 514/40; 536/13.8; 536/16.1
[58] Field of Search ................ 536/13.8, 16.1; 514/41, 514/40

[56] References Cited

U.S. PATENT DOCUMENTS

| | | | |
|---|---|---|---|
| 4,104,372 | 8/1978 | Umezawa | 536/13.8 |
| 4,136,254 | 1/1979 | Nagabhushan | 536/13.8 |
| 4,547,492 | 10/1985 | Umezawa | 536/13.8 |

*Primary Examiner*—Ronald W. Griffin
*Assistant Examiner*—Pamela S. Webber
*Attorney, Agent, or Firm*—Wenderoth, Lind & Ponack

[57] ABSTRACT

An aminoglycoside compound represented by the following formula (I)

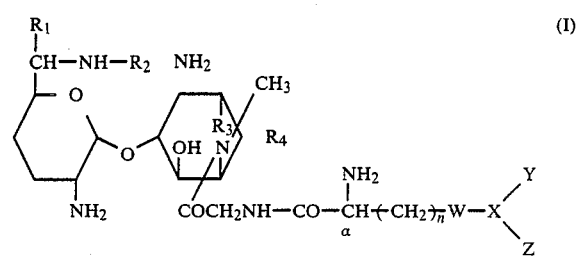

wherein
one of $R_1$ and $R_2$ represents a hydrogen atom, and the other represents a methyl group,
$R_3$ represents a hydrogen atom or a hydroxyl group,
$R_4$ represents a hydrogen atom, a hydroxyl group or a methoxy group,
n represents an integer of 1 to 5,
W represents a divalent group of the formula —NHCO→, —CONH→, —COO→, or —S→ in which→ represents a bond to X, and
X represents (i) a single bond or (ii) a $C_1$–$C_{20}$ trivalent acyclic saturated hydrocarbon group, and
Y and Z are separately defined according to the cases (i) and (ii) above, and its pharmaceutically acceptable acid addition salt; and a process for producing the above aminoglycoside compound. A pharmaceutical composition comprising the above aminoglycoside compound is useful as an antibiotic.

6 Claims, No Drawings

AMINOGLYCOSIDE COMPOUNDS, PROCESSES FOR PRODUCTION THEREOF, AND PHARAMACEUTICAL COMPOSITION CONTAINING THE SAME

This invention relates to aminoglycoside compounds and their pharmaceutically acceptable acid addition salts which have not been described in the known literature and which are useful as antibiotics or as intermediates for the synthesis of antibiotics. The invention also relates to processes for producing these aminoglycoside compounds and their pharmaceutically acceptable acid addition salts. The invention further relates to a pharmaceutical composition comprising such a novel compound or salt.

More specifically, this invention pertains to aminoglycoside compounds represented by the following formula (I)

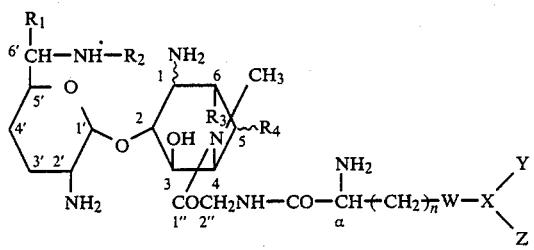

wherein
one of $R_1$ and $R_2$ represents a hydrogen atom, and the other represents a methyl group,
$R_3$ represents a hydrogen atom or a hydroxyl group,
$R_4$ represents a hydrogen atom, a hydroxyl group or a methoxy group,
n represents an integer of 1 to 5,
W represents a divalent group of the formula —NHCO→, —CONH→, —COO→, or —S→ in which → represents a bond to X, and
X represents (i) a single bond or (ii) a $C_1$–$C_{20}$ trivalent acyclic saturated hydrocarbon group, with the proviso that when X represents a single bond (i), the group —Z is absent in the formula, and Y represents a $C_6$–$C_{10}$ aryl group, a 3,12-dihydroxy-24-norcholan-23-yl group, the group —O—$Q^1$ or the group —CO—$Q^1$ in which $Q^1$ represents a $C_1$–$C_9$ alkyl group, and that when X represents a $C_1$–$C_{20}$ trivalent acyclic saturated hydrocarbon group (ii), the groups Z and Y, independently from each other, represent a hydrogen atom, a hydroxyl group, a carboxyl group, the group —COO$Q^1$ in which $Q^1$ is as defined, a phenyl group unsubstituted or substituted by lower alkoxy or nitro, a pyridyl group, a phenyl($C_1$–$C_3$)alkyl group, the group —O—$Q^1$ in which $Q^1$ is as defined, the group —CH$_2$)$_l$O—CO$Q^2$, the group —CO—$Q^3$ or the group —CH$_2$)$_l$NHCO$Q^4$ in which $Q^2$ represents a 3,12-dihydroxy-24-nor-cholan-23-yl group, a 3,12-diacetyloxy-24-nor-cholan-23-yl group, a $C_1$–$C_{20}$ alkyl group or a naphthyl group, $Q^3$ represents a $C_3$–$C_8$ alkylamino group, $Q^4$ represents a 3,12-dihydroxy-24-nor-cholan-23-yl group, a 3,12-diacetyloxy-24-nor-cholan-23-yl group, a 3,12-dipropyloxy-24-nor-cholan-23-yl group or a $C_1$–$C_{25}$ alkyl group, and
l represents 0 or an integer of 1 to 6; and their pharmaceutically acceptable acid addition salts.

This invention further relates to a pharmaceutical composition comprising an aminoglycoside compound of formula (I) or its pharmaceutically acceptable acid addition salt and a pharmaceutically acceptable diluent or carrier, and to processes for producing the compounds of formula (I) and their pharmaceutically acceptable acid addition salts.

In formula (I), the 3,12-dihydroxy-24-nor-cholan-23-yl group denotes a group of the following formula wherein the two R's are hydrogen atoms; the 3,12-diacetyloxy-24-nor-cholan-23-yl group, a group of the following formula wherein the two R's are acetyl groups; and the 3,12-dipropyloxy-24-nor-cholan-23-yl group, a group of the following formula wherein the two R's are propyl groups.

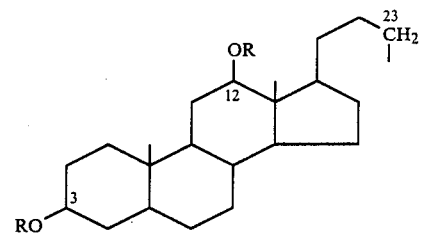

Compounds of the following formulae (II) and (IV) have been known previously.

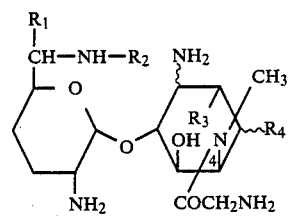

wherein $R_1$, $R_2$, $R_3$ and $R_4$ are as defined above.

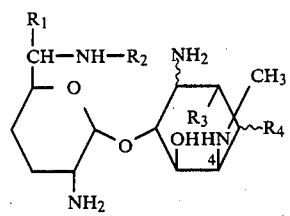

wherein $R_1$, $R_2$, $R_3$ and $R_4$ are as defined above.

These compounds represented by formulae (II) and (IV) are known as KA-6606 substance (sporaricins) obtained as a metabolite of a known *Saccharopolyspora hirsuta* KC-6606 strain (for example, ATCC 20501) and KA-7038 substance (sannamycins) obtained as a metabolite of a known Streptomyces sp. KC-7038 strain (for example, ATCC 31530), fortimicins obtained as metabolites of known micromonospora.olivoasterospora strains, and 4-N-glycyl derivatives of these known substances. They are described in detail, for example, in U.S. Pat. Nos. 3,931,400, 3,976,768, 4,124,756, 4,206,206, 4,255,421, 4,312,858, 4,353,893, 4,425,430 and 4,515,942 and Japanese Laid-Open Patent Publications Nos. 111497/1980 and 164695/1980.

Conventional aminoglycoside antibiotics are hardly absorbable by administration through the digestive tract, for example by oral administration or intrarectal administration, and are presently administered clinically as injectables. Administration by injection, however, is complex and painful to the patient, and side-effects such as local disorders have also been pointed out. It has been desired therefore to develop non-injecting formulations.

The present inventors made investigations in order to solve the above problem with regard to aminoglycoside antibiotics such as those exemplified above, and previously found that compounds resulting from bonding various amino acids or dipeptides to the amino moiety of the glycyl group at the 4-position can be administered through the digestive tract [(U.S. patent application Ser. No. 640,593 (now U.S. Pat. No. 4,647,656); corresponding to Japanese Laid-Open Patent Publication Nos. 42394/1985 and 180798/1986)].

Further work of the present inventors has led to the discovery that the compounds of formula (I) not described in the known literature and their acid addition salts exist stably and can be synthesized; and that the compounds of formula (I) and their acid addition salts are useful as antibiotics which are better than the above compounds and can be administered through the digestive tract.

It is an object of this invention therefore to provide novel aminoglycoside compounds of formula (I) and their pharmaceutically acceptable acid addition salts, and a pharmaceutical composition containing such a compound.

Another object of this invention is to provide processes for producing these compounds.

The above and other objects and advantages of this invention will become apparent from the following description.

The novel aminoglycoside compounds of this invention are represented by the following formula (I)

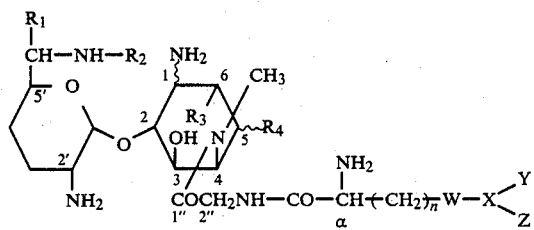

wherein $R_1$, $R_2$, $R_3$, $R_4$, n, W, X, Y and Z are as defined hereinabove.

The outstanding characteristic feature of the compounds of this invention is that in formula (I), they have a moiety (A) having a structure represented by the following formula (A).

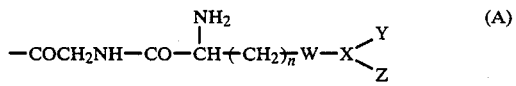

wherein n represents an integer of 1 to 5, preferably 1 to 4,

W represents a divalent group represented by the formula —NHCO→, —CONH→, —COO→, or —S→ in which → represents a bond to X, and X represents (i) a single bond or (ii) a $C_1$–$C_{20}$ trivalent acyclic saturated hydrocarbon group.

Examples of the $C_1$–$C_{20}$ trivalent acyclic saturated hydrocarbon group for X are

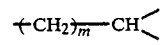

wherein m is 0 or an integer of 1 to 19, and

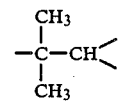

In the moiety (A), Y and Z are defined as follows with regard to the case where X is a single bond (i), and the case where X is a $C_1$–$C_{20}$ trivalent acyclic saturated hydrocarbon group.

When X represents a single bond (i):

The group —Z is absent in the moiety (A), and the moiety (A) is represented by the following formula (A)'

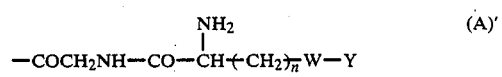

wherein Y represents a $C_6$–$C_{10}$ aryl group such as a phenyl or naphthyl group, a 3,12-dihydroxy-24-nor-cholan-23-yl group, the group —O—$Q^1$ or the group —CO—$Q^1$ in which $Q^1$ represents a $C_1$–$C_9$ alkyl group.

When X represents a $C_1$–$C_{20}$ trivalent acyclic saturated hydrocarbon group (ii):

In the moiety (A), the groups Z and Y, independently from each other, represent a hydrogen atom, a hydroxyl group, a carboxyl group, the group —COO$Q^1$ in which $Q^1$ is as defined, a phenyl group unsubstituted or substituted by lower alkoxy (e.g., methoxy or ethoxy) or nitro, a pyridyl group, a phenyl($C_1$–$C_3$)alkyl group, the group —O—$Q^1$ in which $Q^1$ is as defined, the group $+CH_2)_{\overline{l}}O—COQ^2$, the group —CO—$Q^3$ or the group $+CH_2)_{\overline{l}}NHCOQ^4$ in which $Q^2$ represents a 3,12-dihydroxy-24-nor-cholan-23-yl group, a 3,12-diacetyloxy-24-nor-cholan-23-yl group, a $C_1$–$C_{20}$ alkyl group or a naphthyl group, $Q^3$ represents a $C_3$–$C_8$ alkylamino group, $Q^4$ represents a 3,12-dihydroxy-24-nor-cholan-23-yl group, a 3,12-di-acetyloxy-24-nor-cholan-23-yl group, a 3,12-dipropyloxy-24-nor-cholan-23-yl group or a $C_1$–$C_{25}$ alkyl group, and l represents 0 or an integer of 1 to 6.

In (i) and (ii) above, the alkyl groups for the various symbols may be selected from $C_1$–$C_{25}$ alkyl groups such as methyl, ethyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetrocosyl and pentacosyl groups, and isomeric groups thereof.

The acid addition salts of the compounds of formula (I) are preferably their pharmaceutically acceptable acid addition salts. Examples of the acid addition salts include their inorganic acid salts such as sulfates, hydrochlorides, hydrobromides, hydroiodides, phosphates, carbonates and nitrates, and their organic acid salts such as acetates, fumarates, malates, citrates, mandelates and succinates.

Industrially, the novel aminoglycoside compounds of formula (I) and their acid addition salts can be produced easily by any of the following processes (1) to (4).

(1) A process which comprises reacting a compound represented by the following formula (II)

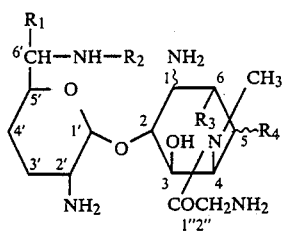

(II)

wherein $R_1$, $R_2$, $R_3$ and $R_4$ are as defined above with regard to formula (I), or a compound resulting from protecting the amino groups at its 1-, 2'- and 6'-positions by protective groups with a compound represented by the following formula (III)

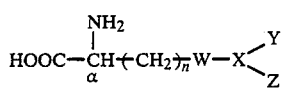

(III)

wherein n, W, X, Y and Z are as defined above with regard to formula (I), or a compound resulting from protecting the amino group at its α-position and a carboxyl group (if present) in Y and Z by protective groups or a reactive derivative thereof in which the carboxyl group at the α-position is its reactive functional group, and thereafter, if required, splitting off the protective groups; or (2) A process which comprises reacting a compound represented by the following formula (IV)

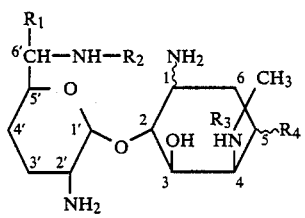

(IV)

wherein $R_1$, $R_2$, $R_3$, and $R_4$ are as defined above with regard to formula (I), or a compound resulting from protecting the amino groups at its 1-, 2'- and 6'-positions by protective groups with a compound represented by the following formula (V)

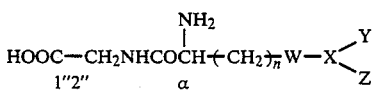

(V)

wherein n, W, X, Y and Z are as defined above with regard to formula (I), or a compound resulting from protecting the amino group at its α-position and a carboxyl group (if present) in Y and Z by protective groups, or a reactive derivative thereof in which the carboxyl group at the 1''-position is its reactive functional group, and if required, splitting off the protective groups; or (3) A process which comprises reacting the compound of formula (II) or the compound resulting from protecting the amino groups at its 1-, 2'- and 6'-positions by protective groups with a compound represented by the following formula (VI)

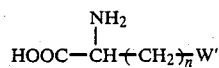

(VI)

wherein W' represents —NH₂ or —COOH, and n is as defined above with regard to formula (I), or a compound resulting from protecting the amino group at its α-position and the amino group or carboxyl group represented by W' by protective groups or a reactive derivative thereof in which the carboxyl group at the α-position is its reactive functional group, and thereafter if required, splitting off the protective group possessed by W', and thereafter (a) amidating the amino group of the compound in which W' is an amino group with a compound represented by the following formula (VII)

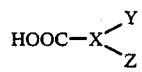

(VII)

wherein X, Y and Z are as defined above with regard to formula (I) or a compound resulting from protecting a carboxyl group (if present) in Y and Z by protective groups, or a reactive derivative thereof in which the —COOH shown in formula (VII) is its reactive functional group, and then if required, splitting off the protective groups;

(b) esterifying the carboxyl group of the compound in which W' is the carboxyl group with a compound represented by the following formula (VIII)

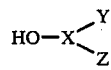

(VIII)

wherein X, Y and Z are as defined above with regard to formula (I) and then if required, splitting off the protective groups; or (c) amidating the carboxyl group of the compound in which W' is the carboxyl group with a compound represented by the following formula (IX)

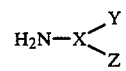

(IX)

wherein X, Y and Z are as defined above with regard to formula (I) and then if required, splitting off the protective groups. thereby to form a compound of formula (I) in which the divalent group W is —NHCO—, —CONH—, or —COO—; or (4) A process which comprises reacting the compound of formula (IV) or the compound resulting from protecting the amino groups at its 1-, 2'- and 6'-positions by protective groups with a compound represented by the following formula (X)

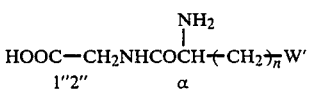

(X)

wherein W' and n are as defined above with regard to formula (VI), or a compound resulting from protecting the amino group at its α-position and the amino or carboxyl group represented by W' by protective groups, or a reactive derivative thereof in which the carboxyl group at the 1″-position is its reactive functional group, and then if required, splitting off the protective group possessed by W', and thereafter performing the same step as (a), (b) or (c) in the process (3), thereby to form a compound of formula (I) in which the divalent group W is —NHCO—→, —CONH—→, or —COO—→.

By contacting the reaction products of formula (I) which can be obtained by processes (1) to (4) above with inorganic or organic acids illustrated above in the examples of the acid addition salts, they can be easily converted into pharmaceutically acceptable acid addition salts.

In the aforesaid processes for producing the amino glycosides compounds of formula (I) and their acid addition salts in accordance with this invention, the starting compounds of formulae (II) and (IV) and processes for their production are known, and can be used in this invention. Examples of the known K-6606 substance, KA-7038 substance and fortimicin are those of the following structural formulae.

Starting compounds of formula (II)

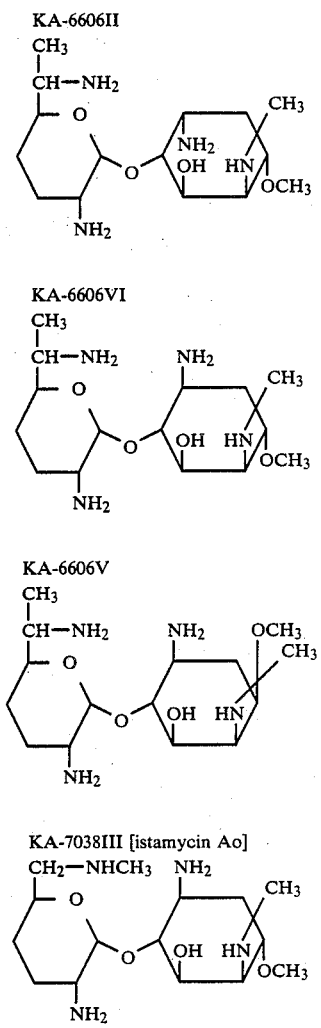

fortimicin A

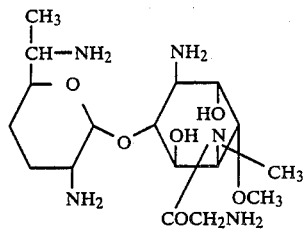

5-de-O-methyl compound and 5-demethoxy compound derived from the above compounds.

Starting compounds of formula (IV)

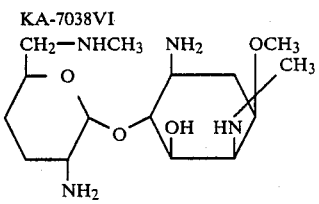

-continued
fortimicin B

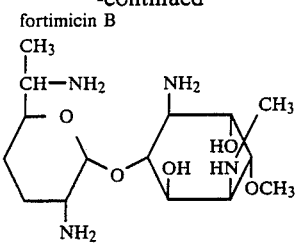

5-de-O-methyl compound and 5-demethoxy compound derived from the above compounds.

When the aminoglycoside compound of formula (I) is to be produced in accordance with process (1) or (2) described above, the reaction is carried out preferably by using the compound obtained by protecting the amino groups of the compound of formula (II) or (IV) at the 1-, 2'- and 6'-positions, with suitable protective groups and the compounds of formula (III) in which the functional groups excepting one carboxyl group, for example the amino group at the α-position and another carboxyl group (if present) in Y and Z, are protected with suitable protective groups or the protected compound of formula (III) in which the aforesaid one carboxyl group is converted into its reactive functional group, or the compound of formula (V) in which the functional groups other than HOOC- at the 1''-position, such as the amino group at the α-position and another carboxyl group (if present) in Y and Z, are protected with suitable protective groups, or the protected compound of formula (V) in which the HOOC- at the 1''-position is converted into its reactive functional group. After the reaction the compound of formula (I) having no protective group can be easily obtained by splitting off the protective groups by a technique known per se.

When the aminoglycoside compound of formula (I) in accordance with this invention is to be produced in accordance with process (3) or (4), it is preferred to react the compound of formula (II) or (IV) in which the amino groups at the 1-, 2'- and 6'-positions are protected with suitable protective groups with the compound of formula (VI) or (X) in which the amino group at the α-position and the amino or carboxyl group represented by W' are protected with suitable protective groups, or the protected compound of formula (VI) or (X) in which the carboxyl group at the α-position or the 1''-position is its reactive functional group, split off the protective group for W' in the resulting reaction product, and thereafter to esterify or amidate the de-protected compound by the method (a), (b) or (c) described above.

In the several embodiments of producing the aminoglycoside compound of formula (I) described above, the compound of formula (II) in which the amino groups at the 1, 2'- and 6'-positions are protected can be obtained by protecting the amino groups at the 1-, 2'- and 6'-positions of the compound of formula (IV), and then glycylating the amino group at the 4-position. The compound of formula (II) in which the amino groups at the 1-, 2'- and 6'-positions are protected can be produced from the compound of formula (IV) by utilizing the following methods described in detail in the Applicant's copending U.S. patent application Ser. No. 640,593 (now U.S. Pat. No. 4,647,656).

First, the amino groups of the compound of formula (IV) are protected in a customary manner, for example with benzyloxycarbonyl groups. Generally, this results in simultaneous protection of the amino groups at the 1-, 4-, 2'- and 6'-positions. But the amino groups at the 1-, 2'- and 6'-positions can be selectively protected by properly selecting the protective group introducing agent in the presence of a divalent metal such as nickel acetate, cobalt acetate or zinc acetate. The preferred introducing agent is, for example, an active ester of a carboxylic acid, preferably its substituted phenyl ester, N-oxysuccinimide ester or N-oxyphthalimide ester. When the methylamino group at the 4-position is simultaneously protected, the methylamino group at the 4-position can be easily rendered free by forming a cyclic carbamate between the hydroxyl group at the 3-position and the methylamino group at the 4-position and then hydrolyzing it. Alternatively, by reacting the tetra-N-protected compound of the compound of formula (IV) with an alkali in a water-containing solvent, the methylamino group at the 4-position can be directly rendered free.

When the resulting compound of formula (IV) in which the amino groups at the 1-, 2'- and 6'-positions are protected is acylated with glycine, a compound of formula (II) in which the amino groups at the 1-, 2'- and 6'-positions are protected can be obtained. The acylation is carried out preferably by using the active derivative at the carboxyl group of the glycine having protected amino groups, particularly its succinimide ester. Preferred protective groups for the amino groups are those which can be split off under different conditions from those under which other protective groups such as benzyloxycarbonyl groups are split off. Examples are a diphenylphosphinothioyl group, a p-methoxybenzyloxycarbonyl group and a t-butoxycarbonyl group. When subsequent to the acylation, the protective group for the amino group at the 2'-position side chain is split off, for example by acid treatment, the 1,2',6'-tris-N-protected compound of formula (II) is obtained.

The compound of formula (II) or (IV) in which $R_4$ is a hydroxyl group can be produced from the starting compound of formula (II) or (IV) having a methoxy group at the 5-position by de-O-methylating it by the method described in U.S. Pat. No. 4,255,421. The compound of formula (II) or (IV) in which $R_4$ is a hydrogen atom can be obtained by dehydroxylating the compound of formula (II) or (IV) in which $R_4$ is a hydroxyl group produced by the above method by the method described in U.S. Pat. No. 4,353,893.

Preferably, the de-O-methylation reaction ($R_4$: OCH$_3$→OH) is carried out before the reaction of protecting the amino groups at the 1-, 2'- and 6'-positions. If desired, the de-O-methylation can be carried out after protecting the amino groups.

The protective groups for the amino groups of the compounds of formulae (II) and (IV) may be any of those protective groups which are used in ordinary peptide syntheses. Especially preferred protective groups include alkyloxycarbonyl groups such as an ethyloxycarbonyl, t-butyloxycarbonyl or t-amyloxycarbonyl group, cycloalkyloxycarbonyl groups such as a cyclohexyloxycarbonyl group, aralkyloxycarbonyl groups such as a benzyloxycarbonyl or p-methoxybenzyloxycarbonyl group, and aryloxycarbonyl groups such as o-nitrophenoxycarbonyl group.

Preferably, the α-amino groups of the compounds of formulae (III), (V), (VI) and (X) are protected prior to the reaction, and protective groups which can be split off under the same conditions as the protective groups for the compound of formula (II) or (Iv) are feasible. The same protective groups are preferred.

The carboxyl group and the amino group to be esterified or amidated in the compound of formula (VI) or (X) used in processes (3) and (4) are preferably protected. Preferred protective groups are those which can be split off under different conditions from those under which the protective groups for the amino groups at the 1-, 2'- and 6'-positions of the compound of formula (II) or (IV) are split off. For example, if benzyloxycarbonyl groups are used as protective groups for the amino groups at the 1-, 2'- and 6'-positions, a tert-butyl ester group is preferably used as a protective group for the carboxyl group to be esterified or amidated in the compound of formula (VI) or (X), and a tert-butyloxycarbonyl group, a p-methoxybenzyloxycarbonyl group, or a diphenylphosphinothioyl group, for example, is preferred as a protective group for the amino group to be amidated in the compound of formula (VI) or (X). If the amino groups at the 1-, 2'- and 6'-positions are protected with tert.-butyloxycarbonyl group, a benzyl ester group which may have a substituent is preferred as a protective group for the carboxyl group to be esterified or amidated in the compound of formula (VI) or (X), and a benzyloxycarbonyl group which may have a substituent is preferred as a protective group for the amino group to be amidated in the compound of formula (VI) or (X).

The reaction of the compound of formula (II) or (IV) with the compound of formula (III), (V), (VI) or (X) may be carried out by the following procedures frequently used in the field of peptide synthesis.

(A) The two compounds are reacted in the presence of a dehydrating agent or a condensing agent. Examples of the dehydrating agent are carbodiimides such as N,N'-dicyclohexylcarbodiimide, and examples of the condensing agent are chloroformate esters and chlorophosphite esters.

(B) The compound of formula (II) or (IV) is reacted with the acid reactive derivative of formula (III), (V), (IV) or (X). Useful acid reactive derivatives are, for example, acid chlorides, acid azides, acid anhydrides, mixed acid anhydrides, and active amides. Preferred are active esters, particularly p-nitrophenyl esters, cyanomethyl esters, N-hydroxysuccinimide esters, and N-hydroxyphthalimide esters.

When the procedure (A) is used in practicing the aforesaid reaction, the compound of formula (II) or (IV) in which the amino group at the 4- or 2''-position is free may be reacted with, for example, 1 to 5 times its amount of the free carboxylic acid of formula (III), (V), (VI) or (X) at a temperature of, for example, 0° to 100° C. for a period of, for example, 1 to 40 hours in a solvent in the presence of a dehydrating agent or a condensing agent. The solvent may, for example, be tetrahydrofuran, acetonitrile, dichloromethane, pyridine, dioxane, or dimethylformamide.

When the procedure (B) is utilized, the compound of formula (II) or (IV) in which the amino group at the 4- or 2''-position is free may be reacted with a nearly equivalent amount of the reactive derivative (e.g., active ester) of formula (III), (V), (VI) or (X) in the same solvent as exemplified with regard to procedure (A) in the presence or absence of a base at a temperature of, for example, 0° to 100° C. for a period of, for example, 1 to 40 hours. Examples of the base are triethylamine, pyridine and diazabicycloundecene.

When processes (3) and (4) are used, it is possible to split off the protective group for the carboxyl or amino group in W' following the reaction by procedure (A) or (B) above, and then to subject the deprotected compound to an ordinary esterification or amidation reaction.

The amidation reaction between the amino group in W' and the carboxylic acid of formula (VII), and the amidation reaction between the carboxyl group in W' and the amine of formula (IX) may be carried out by applying the procedures (A) and (B) described above.

The esterification reaction between the carboxyl group in W' and the alcohol of formula (VIII) may be carried out by reacting a condensate between the compound of formula (II) or (IV) and the compound of formula (VI) or (X) with 1 to 10 times the weight of the condensate of the alcohol of formula (VIII) in a solvent in the presence of a dehydrating agent and a small amount of a base at a temperature of 0° to 100° C. for 1 to 40 hours. Examples of the solvent that can be used in this reaction include acetonitrile, chloroform, dichloromethane, benzene, toluene, and dimethylformamide. The base may, for example, be triethylamine, dimethylaminopyridine, pyridine or diazabicycloundecene.

When the protective groups of the resulting compound of formula (I) in which the amino groups and other functional groups are protected are split off, the free compound of formula (I) is obtained. Ordinary methods can be applied to the elimination of the protective groups, but the use of a catalytic reducing method and an acid-catalyzed cleavage method is preferred.

Palladium, platinum, Raney nickel, rhodium, ruthenium and nickel can be exemplified as a catalyst for the catalytic reduction. The catalytic reduction may be carried out in the same solvent, for example, methanol, ethanol, dioxane, dimethylformamide, acetic acid, and suitable mixtures thereof. This reaction can be carried out, for example, at a hydrogen pressure of 1 to 5 atmospheres and a temperature of 0° to 100° C. for 0.1 to 10 hours.

Acid-catalyzed cleavage can be carried out by contacting the compound of formula (I) in which the amino groups and other functional groups are protected with an acid in a solvent. Examples of the acid are hydrochloric acid, hydrobromic acid, hydrofluoric acid, p-toluene-sulfonic acid, trifluoroacetic acid, etc. The solvent may be acetic acid, methanol, ethanol, dioxane, water, etc. The reaction can be carried out, for example, at 0° to 100° C.

The desired compound of formula (I) and the compound of formula (I) in which the amino groups are protected can be isolated and purified by conventional methods, preferably by column chromatography. It is preferred to use cation exchange resins such as CM-Sephadex, Amberlite IRC-50, IRC-84 and CG-50, carboxymethyl cellulose, silica gel and cellulose as an adsorbent. The column may be developed with a developing solvent, for example an aqueous alkaline solution such as aqueous ammonia and an aqueous solution of ammonium formate or an organic solvent such as chloroform and methanol by a concentration gradient method or a concentration stepwise method. Active fractions are collected from the eluates, and lyophilized to give the desired compound of formula (I) as a pure product.

The compound of formula (I) can be converted to acid addition salts by contacting it with acids. Examples of the acids are inorganic acids such as sulfuric acid, hydrochloric acid, hydrobromic acid, hydriodic acid, phosphoric acid, carbonic acid and nitric acid, and organic acids such as fumaric acid, malic acid, citric acid, mandelic acid and succinic acid. The reaction of forming the acid addition salt is carried out by adding the acid in an amount required for neutralization to an aqueous solution of the compound of formula (I), and lyophilizing the resulting product.

The aminoglycoside compounds and their pharmaceutically acceptable acid addition salts in accordance with this invention are useful as antibiotics or as synthetic intermediates for other antibiotics.

According to this invention, there may be provided a pharmaceutical composition comprising an antibiotically effective amount of an aminoglycoside of formula (1) or its pharmaceutically acceptable acid addition salt and a pharmaceutically acceptable diluent or carrier.

The aminoglycosides of formula (I) or their pharmaceutically acceptable acid addition salts provided by this invention have the advantage of being easily absorbable by administration through the digestive tract. Thus, the pharmaceutical composition of this invention can be, and is preferably, as a formulation administrable through the digestive tract such as an orally administrable formulation or an intrarectally administrable formulation.

The compound of formula (1) and their pharmaceutically acceptable acid addition salts can be formed into pharmaceutical compositions of various known formulations by methods known per se.

Examples of the diluent or carrier used in the pharmaceutical composition include liquid or solid diluents or carriers known in the field of drug preparation, such as excipients, binders, lubricants, disintegrants, coating agents, emulsifiers, suspending agents, solvents, stabilizers and absorption aids.

For oral administrations, such formulations as granules, tablets, sugar-coated tablets, capsules, pills, liquid preparations, emulsions and suspensions may be cited as example. For intrarectal administration, suppositories and soft capsules are preferred. Formulations for oral administration are preferably enteric-coated.

Examples of the excipients are starch, lactose, sucrose, methyl cellulose, carboxymethyl cellulose, sodium alginate, magnesium meta-silicate aluminate, calcium lactate, calcium hydrogen phosphate, synthetic aluminum silicate, microcrystalline cellulose, polyvinylpyrrolidone, colloidal silica gel, hydroxypropyl starch and hardened oils. Examples of the binders are crystalline cellulose, hydroxypropyl cellulose, hydroxypropylmethyl cellulose, polyvinylpyrrolidones, polyvinyl alcohol, waxes and rubbers. Examples of the lubricants are talc, starch, stearic acid, magnesium stearate, calcium stearate, boric acid, paraffin, cacao butter, sodium benzoate, leucine, polyethylene glycol and hydrogenated soybean oil. Examples of the disintegrants are carboxymethyl cellulose, carboxymethyl cellulose calcium salt, starch, hydroxypropyl starch and crystalline cellulose. Examples of the coating agents are shellac, cellulose acetate phthalate, hydroxypropylmethyl cellulose, hydroxypropylmethyl cellulose phthalate, methyl methacrylate/methacrylic acid copolymer, and 2-methyl-5-vinylpyridinemethyl acrylate/methacrylic acid copolymer.

Examples of absorption aids include polyoxyethylated nonionic surfactants, organic acids or salts thereof, N-acyleollagen peptides, N-acylpeptides, N-acylamino acids and bile acid.

Examples of bases that are used in the preparation of the suppositories include oily bases, for example peanut oil, olive oil, corn oil, castor oil, $C_8$–$C_{12}$ fatty acids such as Miglyol (Mitsuba Trading Co., Ltd.), glycerin esters of fatty acids such as Witepsol (Dynamit Nobel) and Pharmasol (Nippon Oils and Fats Co., Ltd.), oleic acid and linolic acid, and water-soluble bases such as polyethylene glycol and propylene glycol.

The pharmaceutical composition of this invention contains an antibiotically effective amount of the aminoglycoside compound of formula (I) of its pharmaceutically acceptable acid addition salt. The amount may be properly varied depending upon the type of the compound of formula (I) or its salt, the type of formulation, etc. For example, it is about 10 to about 90% by weight [in terms of the weight of the compound (I)] based on the weight of the composition.

The pharmaceutical composition can be administered through various routes, such as intramuscular, intravenous, subcutaneous, intrarectal and oral. However, as stated hereinabove, routes through the digestive tract, such as oral and intrarectal routes, are preferred. The dose of the compound of formula (I) or its acid addition salt may, for example, be about 0.1 to about 100 mg/kg/day. This dose may be administered once a day, or be divided into 2 to 4 portions a day.

The pharmaceutical composition of this invention may be used to prevent or treat infectious diseases induced by various pathogenic bacteria such as *Escherichia coli*, *Streptomyces aureus*, *Klebsiera pneumoniae*, *Proteus vulgaris*, *Pseudomonas aeruginosa*, *Enterobacter cloacae* and *Serratia marcescens*.

The biological activities of the compounds of formula (I) and their acid addition salts provided by this invention were tested, and the results are shown below.

I. Test for antibacterial activity

Each of the test compounds shown in the following table was dissolved in a concentration of 200 mcq/ml in a homogenate of a 10% physiological saline solution of an organ of a rat, and incubated at 37° C. for 2 hours. An enzymatic reaction was stopped by adding an equal amount of ethanol. The antibacterial activity of the test compound before incubation was compared with that after incubation. The incubation was carried out in an equal amount mixture of a liver homogenate and a kidney homogenate.

The antibacterial activity was measured by a paper disk having a diameter of 8 mm using *Bacillus subtilis* ATCC 6633 as a test organism, and shown by the diameter of the resulting inhibitory zone. The results are tabulated below. In view of these results, the compounds of formula (I) and their acid addition salts are expected to have excellent antibacterial activity in vivo.

TABLE 1

| Test compound No. (corresponding to Example Nos. given hereinafter) | Diameter of the inhibitory zone (mm) | |
| --- | --- | --- |
| | Before incubation | After incubation |
| 1 | 14.1 | 25.1 |
| 2 | 15.9 | 22.0 |
| 3 | 14.0 | 15.5 |
| 4 | 12.7 | 19.8 |
| 5 | 15.5 | 21.0 |
| 6 | 10.5 | 16.6 |
| 7 | 10.5 | 20.7 |
| 8 | 15.9 | 23.9 |
| 9 | 12.7 | 23.2 |

TABLE 1-continued

| Test compound No. (corresponding to Example Nos. given hereinafter) | Diameter of the inhibitory zone (mm) | |
|---|---|---|
| | Before incubation | After incubation |
| 10 | 14.2 | 21.1 |
| 11 | 14.0 | 19.0 |
| 12 | 12.6 | 18.3 |
| 13 | 13.7 | 18.8 |
| 15 | 13.9 | 24.4 |
| 16 | 12.5 | 17.5 |
| 17 | 10.6 | 19.7 |
| 18 | 16.8 | 23.9 |
| 19 | 13.7 | 22.7 |
| 20 | 14.1 | 21.8 |
| 21 | 15.1 | 22.6 |
| 22 | 10.7 | 18.3 |
| 23 | 10.5 | 19.5 |
| 24 | 16.2 | 22.6 |
| 26 | 14.8 | 21.8 |
| 27 | 13.5 | 23.2 |
| 28 | 14.6 | 23.9 |
| 29 | 15.1 | 24.6 |
| 30 | 15.0 | 19.8 |
| 31 | 15.3 | 19.0 |
| 32 | 14.1 | 19.0 |
| 33 | 15.7 | 23.5 |
| 34 | 10.7 | 23.1 |
| 35 | 10.7 | 20.7 |
| 36 | 10.5 | 22.8 |
| 37 | 14.1 | 25.1 |
| 38 | 17.1 | 23.9 |
| 39 | 9.8 | 21.2 |
| 40 | 14.1 | 16.6 |
| 41 | 8.0 | 14.1 |
| 42 | 15.1 | 23.0 |
| 43 | 10.8 | 18.4 |
| 44 | 8.0 | 20.2 |
| 45 | 14.8 | 16.7 |
| 46 | 15.9 | 16.6 |
| 47 | 9.5 | 17.9 |
| 48 | 18.0 | 18.3 |
| 49 | 15.9 | 16.1 |
| 50 | 15.0 | 23.6 |
| 51 | 18.3 | 25.4 |
| 52 | 20.7 | 26.2 |
| 53 | 16.5 | 24.3 |
| 54 | 14.1 | 25.3 |
| 55 | 10.3 | 18.6 |
| 56 | 17.5 | 24.6 |
| 57 | 15.9 | 23.0 |

II. Test for concentrations in blood (1) Intraduodenal administration

Male rats (body weight 250–350 g: n=3) which had been caused to fast for 18 hours prior to administration were anesthetized with pentobarbirtal. After the abdomen was incised, the upper part of the duodenum was tied. Each of the test compounds was dissolved in water so that its concentration became 12.5 mg/ml as its starting antibiotic (the compound of formula II), and the solution was intraduodenally administered to the rats in a dose of 2 ml/kg. After the administration, blood was drawn periodically from the tail vein, and the concentration of the starting antibiotic in the blood was measured by antimicrobial assay and liquid chromatography. Table 2 shows the maximum concentration in the blood ($C_{max}$) and the time which elapsed until the maximum concentration reached ($T_{max}$).

TABLE 2

| Test compound No. (corresponding to Example Nos. given hereinafter) | Maximum concentration in blood | |
|---|---|---|
| | $C_{max}$ (μg/ml) | $T_{max}$ (min.) |
| 34 | 1.5 | 60 |
| 35 | 2.9 | 180 |
| 36 | 5.1 | 30 |
| 37 | 4.86 | 30 |
| 38 | 3.61 | 60 |
| 39 | 2.54 | 90 |
| 51 | 4.20 | 30 |
| 52 | 1.41 | 90 |
| 53 | 2.65 | 30 |
| 54 | 2.47 | 90 |

(2) Intrarectal administration

Male rats (body weight 250–350 g: n=3) which had been caused to fast for 18 hours prior to administration were anesthetized with pentobarbirtal. After the abdomen was incised, the lower part of the rectum was tied. Each of the test compounds was administered intrarectally in the same dose in the same manner as in (1) above, and the concentration of the starting antibiotic in the blood was measured in the same way as in (1) above. Table 3 shows the maximum concentration in the blood ($C_{max}$) and the time which elapsed until the maximum concentration reached ($T_{max}$).

TABLE 3

| Test compound No. (corresponding to Example Nos. given hereinafter) | Maximum concentration in blood | |
|---|---|---|
| | $C_{max}$ (μg/ml) | $T_{max}$ (min.) |
| 18 | 7.37 | 30 |
| 20 | 7.76 | 30 |
| 21 | 9.29 | 90 |
| 27 | 5.30 | 30 |
| 36 | 1.14 | 60 |
| 37 | 6.26 | 120 |
| 38 | 25.1 | 15 |
| 39 | 4.68 | 180 |

The experimental results given in Tables 2 and 3 demonstrate that the compounds of formula (1) can be well absorbed and show effective concentrations in the blood by oral and intrarectal administration.

EXAMPLE 1

Production of 2''-N-(N$^\epsilon$-acetyl-L-lysyl)-5-de-O-methyl-KA-6606I:

(a) 51 mg of 1,2',6'-tris-N-benzyloxycarbonyl-5-de-O-methyl-KA-6606I was dissolved in 2 ml of dioxane, and 70 mg of an N-hydroxysuccinimide ester of N$^\epsilon$-acetyl-N$^\alpha$-benzyloxycarbonyl-L-lysine and 50 mg of triethylamine were added. The mixture was left to stand overnight at room temperature. The reaction mixture was concentrated to dryness, and the residue was dissolved in chloroform, washed with water, and dried. The solvent was then evaporated. The residue was purified by preparative thin-layer chromatography [carrier: silica gel; solvent: chloroform/methanol (30:1)] to give 64 mg of 2''-N-(N$^\epsilon$-acetyl-N$^\alpha$-benzyloxycarbonyl-L-lysyl)-1,2',6'-tris-N-benzyloxycarbonyl-5de-O-methyl-KA-6606I as a colorless solid.

Specific rotation: $[\alpha]_D^{23}$ +30° (c=2, CHCl$_3$)
IR value: $\nu_{max}^{CHCL_3}$, cm$^{-1}$ 1640 (amide I)
$^1$H-NMR value: $\delta_{CDCl_3}^{TMS}$, ppm
1.04 (3H, d, J=6 Hz, C—CH$_3$)

1.84 (3H, s, N—COCH$_3$)
Elemental analysis for C$_{56}$H$_{71}$N$_7$O$_{15}$:

|  | C | H | N |
|---|---|---|---|
| Calculated (%): | 62.15 | 6.61 | 9.06 |
| Found (%): | 62.40 | 6.58 | 8.87 |

(b) The N-protected compound obtained in (a) (64 mg) was dissolved in 3 ml of 0.2N methanolic hydrochloric acid, and 65 mg of 5% palladium-carbon was added. The mixture was subjected to catalytic reduction at room temperature under atmospheric pressure. The catalyst was removed by filtration. The filtrate was concentrated to dryness, and lyophilized to give 40 mg of the hydrochloride of the captioned compound as a colorless solid.

Specific rotation: $[\alpha]_D^{24}$ +80° (c=1.5, H$_2$O) $^1$H-NMR value: $\delta_{D_2O}^{TMS}$, ppm
1.34 (3H, d, J=7 Hz, C$^{6'}$—CH$_3$)
1.99 (3H, s, N—COCH$_3$)
3.16 (3H, s, N—CH$_3$)
5.48 (1H, d, J=3.5 Hz, H-1')
Elemental analysis for C$_{24}$H$_{47}$N$_7$O$_{17}$.4HCl.2H$_2$O:

|  | C | H | N | Cl |
|---|---|---|---|---|
| Calculated (%): | 39.62 | 7.62 | 13.48 | 19.49 |
| Found (%): | 39.91 | 7.64 | 13.24 | 19.72 |

EXAMPLE 2

Production of 2''-N-(N$^\epsilon$-decanoyl-L-lysyl)-5-de-O-methyl-KA-6606I:

(a) 630 mg of 1,2',6'-tris-N-benzyloxycarbonyl-5-de-O-methyl-KA-6606I and 500 mg of an N-hydroxysuccinimide ester of N$^\alpha$-benzyloxycarbonyl-N$^\epsilon$-decanoyl-L-lysine were reacted and worked up in the same way as in Example 1, (a). Purification of the reaction product by silica gel column chromatography [solvent: chloroform/ethyl acetate/acetone (2:2:1→1:1:1)] to give 490 mg of 1,2',6'-tris-N-benzyloxycarbonyl-2''-N-(N$^\alpha$-benzyloxycarbonyl-N$^\epsilon$-decanoyl-L-lysyl)-5-de-O-methyl-KA6606I as a colorless solid.

Specific rotation: $[\alpha]_D^{23}$ −31° (c=1, CHCl$_3$)
IR value: $\nu_{max}^{CHCL3}$, cm$^{-1}$
1710 (urethane), 1640 (amide I),
1510 (amide II)
$^1$H-NMR value: $\delta_{CDCl_3}^{TMS}$, ppm
0.87 [3H, t, —(CH$_2$)$_8$—C$\underline{H}_3$]
1.02 (3H, d, J=7 Hz, C$^{6'}$—CH$_3$)
~7.3 (20H, aromatic H)
Elemental analysis for C$_{64}$H$_{87}$N$_7$O$_{15}$:

|  | C | H | N |
|---|---|---|---|
| Calculated (%): | 64.36 | 7.34 | 8.21 |
| Found (%): | 64.71 | 7.22 | 8.09 |

(b) The N-protected compound (490 mg) obtained in (a) was reacted and worked up in the same way as in Example 1, (b) to give 329 mg of the hydrochloride of the captioned compound as a colorless solid.

Specific rotation: $[\alpha]_D^{23}$ +75° (c=1, H$_2$O)
IR value: $\nu_{max}^{KBr}$, cm$^{-1}$
1620 (amide I)
$^1$H-NMR value: $\delta_{D_2O}^{TMS}$, ppm
0.88 [3H, t, —(CH$_2$)$_8$—C$\underline{H}_3$]
1.35 (3H, d, J=7 Hz, C$^{6'}$—CH$_3$)
3.18 (3H, s, N—CH$_3$)
5.50 (1H, d, J=3.5 Hz, H-1')
Elemental analysis for C$_{32}$H$_{63}$N$_7$O$_7$.4HCl.H$_2$O:

|  | C | H | N | Cl |
|---|---|---|---|---|
| Calculated (%): | 46.77 | 8.46 | 11.93 | 17.26 |
| Found (%): | 46.49 | 8.73 | 11.69 | 17.02 |

EXAMPLE 3

Production of 2''-N-(N$^\epsilon$-stearoyl-L-lysyl)-5-de-O-methyl-KA-6606I:

(a) 298 mg of 1,2',6'-tris-N-benzyloxycarbonyl-5-de-O-methyl-KA-6606I and 295 mg of an N-hydroxysuccinimide ester of N$^\alpha$-benzyloxycarbonyl-N$^\epsilon$-stearoyl-L-lysine were reacted and worked up in the same way as in Example 1, (a). Purification of the reaction product by silica gel column chromatography [solvent: chloroform/methanol (30:1)] gave 290 mg of 1,2',6'-tris-N-benzyloxycarbonyl-2''-N-(N$^\alpha$-benzyloxycarbonyl-N$^\epsilon$-stearoyl-L-lysyl)-5-de-O-methyl-KA-6606I as a colorless solid.

Specific rotation: $[\alpha]_D^{24}$ +28° (c=2, CHCl$_3$)
$^1$H-NMR value: $\delta_{CDCl_3}^{TMS}$, ppm
0.88 [3H, t, —(CH$_2$)$_{16}$—C$\underline{H}_3$]
1.04 (3H, d, J=6 Hz, C$^{6'}$—CH$_3$)
1.24 (s, stearoyl methylene portion)
2.10 [2H, t, J=7 Hz, —CO—C$\underline{H}_2$—(CH$_2$)$_{15}$—]
Elemental analysis for C$_{72}$H$_{103}$N$_7$O$_{15}$:

|  | C | H | N |
|---|---|---|---|
| Calculated (%): | 66.18 | 7.95 | 7.50 |
| Found (%): | 65.98 | 8.21 | 7.63 |

(b) The N-protected compound (290 mg) obtained in (a) was reacted and worked up in the same way as in Example 1, (b) to give 166 mg of the hydrochloride of the captioned compound as a colorless solid.

Specific rotation: $[\alpha]_D^{24}$ +74° (c=1, H$_2$O)
$^1$H-NMR value: $\delta_{D_2O}^{TMS}$, ppm
0.87 [3H, t, —(CH$_2$)$_{16}$—C$\underline{H}_3$]
1.28 (s, stearoyl methylene portion)
1.34 (3H, d, J=6.7 Hz, C$^{6'}$—CH$_3$)
3.16 (3H, s, N—CH$_3$)
5.47 (1H, d, J=3 Hz, H-1')
Elemental analysis for C$_{40}$H$_{79}$N$_7$O$_{17}$.4HCl.2H$_2$O:

|  | C | H | N | Cl |
|---|---|---|---|---|
| Calculated (%): | 43.20 | 7.89 | 8.82 | 12.75 |
| Found (%): | 43.32 | 7.68 | 8.41 | 13.23 |

EXAMPLE 4

Production of 2''-N-(N$^\epsilon$-deoxycholyl-L-lysyl)-5-de-O-methyl-KA-6606I:

(a) 52 mg of 1,2',6'-tris-N-benzyloxycarbonyl-5-de-O-methyl-KA-6606I and 51 mg of an N-hydroxysuccinimide ester of N$^\alpha$-benzyloxycarbonyl-N$^\epsilon$-deoxycholyl-L-lysine were reacted and worked up in the same way as in Example 1, (a). The product was purified by preparative thin-layer chromatography [carrier: silica gel; solvent: chloroform/methanol/conc. aqueous ammonia (70:10:1)] to give 55 mg of 1,2',6'-tris-N-benzyloxycarbonyl-2''-N-(N$^\alpha$-benzyloxycarbonyl-N$^\epsilon$-deoxycholyl-L-lysyl)-5-de-O-methyl-KA-6606I as a colorless solid.
Specific rotation: $[\alpha]_D^{23}$ +38° (c=2, CHCl$_3$)
IR value: $\nu_{max}^{CHCl_3}$, cm$^{-1}$
1635 (amide I)
$^1$H-NMR value: $\delta_{CDCl_3}^{TMS}$, ppm
0.64 (3H, s, deoxycholyl CH$_3$—18)
7.1–7.4 (20H, aromatic H)
Elemental analysis for C$_{78}$H$_{107}$N$_7$O$_{17}$:

|  | C | H | N |
|---|---|---|---|
| Calculated (%): | 66.22 | 7.62 | 6.93 |
| Found (%): | 66.57 | 7.64 | 6.68 |

(b) The N-protected compound (55 mg) obtained in (a) was reacted and worked up in the same way as in Example 1, (b) to give 36 mg of the hydrochloride of the captioned compound as a colorless solid.
Specific rotation: $[\alpha]_D^{25}$ +78° (c=1, H$_2$O)
$^1$H-NMR value: $\delta_{D_2O}^{TMS}$, ppm
0.72 (3H, s, deoxycholyl CH$_3$—18)
0.94 (3H, s, deoxychlolyl CH$_3$—19)
0.99 (3H, d, J=5.8 Hz, deoxycholyl CH$_3$—21)
1.35 (3H, d, J=7.0 Hz, C$^{6'}$—CH$_3$)
3.17 (3H, s, N—CH$_3$)
5.48 (1H, d, J=3.4 Hz, H-1')
Elemental analysis for C$_{46}$H$_{83}$N$_7$O$_9$.4HCl.2H$_2$O:

|  | C | H | N | Cl |
|---|---|---|---|---|
| Calculated (%): | 52.12 | 8.65 | 9.25 | 13.38 |
| Found (%): | 52.50 | 8.73 | 9.10 | 13.64 |

EXAMPLE 5

Production of 2''-N-[N$^\epsilon$-(N-decanoylglysyl)-L-lysyl)]-5-de-O-methyl-KA-6606I:

(a) 378 mg of 1,2',6'-tris-N-benzyloxycarbonyl-5-de-O-methyl-KA-6606I and 410 mg of an N-hydroxysuccinimide ester of N$^\alpha$-benzyloxycarbonyl-N$^\epsilon$-(N-decanoylglycyl)-L-lysine were reacted and worked up in the same way as in Example 1, (a) to purify silica gel column chromatography [solvent: chloroform-ethyl acetate-acetone (1:1:1→1:1:2)] to give 458 mg of 1,2',6'-tris-N-benzyloxycarbonyl-2''-N-[N$^\alpha$-benzyloxycarbonyl-N$^\epsilon$-(N-decanoylglysyl)-L-lysyl]-5-de-O-methyl-KA-6606I as a colorless solid.
Specific rotation: $[\alpha]_D^{24}$ +30° (c=1, CHCL$_3$)
IR value: $\nu_{max}^{CHCl_3}$, cm$^{-1}$
1710 (urethane), 1640 (amide I), 1510 (amide II)
$^1$H-NMR values: $\delta_{CDCl_3}^{TMS}$, ppm
0.88 [3H, t, —(CH$_2$)$_8$—C$\underline{H_3}$]
1.04 (3H, d, J=7 Hz, C$^{6'}$—CH$_3$)
~7.3 (20H, aromatic H)
Elemental analysis for C$_{66}$H$_{90}$N$_8$O$_{16}$:

|  | C | H | N |
|---|---|---|---|
| Calculated (%): | 63.34 | 7.25 | 8.95 |
| Found (%): | 63.58 | 7.43 | 8.81 |

(b) 402 mg of the N-protected compound obtained in (a) was reacted and worked up in the same way as in Example 1, (b) to give 263 mg of the hydrochloride of the captioned compound as a colorless solid.
Specific rotation: $[\alpha]_D^{20}$ +66° (c=1, H$_2$O)
IR value: $\nu_{max}^{KBr}$, cm$^{-1}$
1630 (amide I)
$^1$H-NMR value: $\delta_{D_2O}^{TMS}$, ppm
0.88 [3H, t, —(CH$_2$)$_8$—C$\underline{H_3}$]
1.35 (3H, d, J=7 Hz, C$^{6'}$—CH$_3$)
3.18 (3H, s, N—CH$_3$)
3.86 (2H, s,

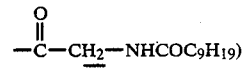

5.50 (1H, d, J=3.5 Hz, H-1')
Elemental analysis for C$_{34}$H$_{66}$N$_8$O$_8$.4HCl.2H$_2$O:

|  | C | H | N | Cl |
|---|---|---|---|---|
| Calculated (%): | 45.54 | 8.32 | 12.49 | 15.81 |
| Found (%): | 45.76 | 8.29 | 12.55 | 15.98 |

EXAMPLE 6

Production of 2''-N-[N$^\epsilon$-(N-stearoylglysyl)-L-lysyl]-5-de-O-methyl-KA-6606I:

(a) 470 mg of 1,2',6'-tris-N-benzyloxycarbonyl-5-de-O-methyl-KA-6606I and 505 mg of an N-hydroxysuccinimide ester of N$^\alpha$-benzyloxycarbonyl-N$^\epsilon$-oleoylglysyl-L-lysine were reacted and worked up in the same way as in Example 1, (a). The reaction product was purified by silica gel column chromatography [solvent:benzene/ethanol (15:1)] to give 359 mg of 1,2',6'-tris-N-benzyloxycarbonyl-2''-N-[N$^\alpha$-benzyloxycarbonyl-N$^\epsilon$-(N-oleoylglycyl-L-lysyl]-5-de-O-methyl-KA-6606I as a colorless solid.
Specific rotation: $[\alpha]_D^{22}$ +24° (c=1, CHCl$_3$)
$^1$H-NMR value: $\delta_{CDCl_3}^{TMS}$, ppm
0.90 (3H, t, oleoyl-CH$_3$)
1.05 (3H, d, J=6 Hz, C$^{6'}$—CH$_3$)
5.40 (2H, m, olefinic H)
Elemental analysis for C$_{74}$H$_{106}$N$_8$O$_{16}$:

|  | C | H | N |
|---|---|---|---|
| Calculated (%): | 65.18 | 7.84 | 8.22 |
| Found (%): | 64.87 | 7.91 | 7.96 |

(b) 169 mg of the N-protected N-(N-oleoylglycyl)-L-lysyl compound contained in (a) was reacted and worked up in the way as in Example 1, (b) to give 106 mg of the hydrochloride of the captioned compound as a colorless solid.
Specific rotation: $[\alpha]_D^{24}$ +68° (c=1, H$_2$O)
$^1$H-NMR value: $\delta_{D_2O}^{TMS}$, ppm
0.87 [3H, t, —CH$_2$)$_{16}$—$\underline{H_3}$]
1.29 (s, stearoyl methylene portion)
1.35 (3H, d, J=6.5 Hz, C$^{6'}$—CH$_3$)
3.17 (3H, s, N—CH$_3$)
3.86 (2H, s, stearoyl glycyl-CH$_2$)
5.48 (1H, d, J=3.5 Hz, H-1')
Elemental analysis for C$_{42}$H$_{82}$N$_8$O$_8$.4HCl.H$_2$O:

|  | C | H | N | Cl |
|---|---|---|---|---|
| Calculated (%): | 50.90 | 8.95 | 11.31 | 14.31 |
| Found (%): | 50.81 | 8.74 | 10.86 | 14.39 |

EXAMPLE 7

Production of 2''-N-(N$^\epsilon$-octyloxycarbonyl-L-lysyl)-5-de-O-methyl-KA-6606I:

(a) 313 mg of 1,2',6'-tris-N-benzyloxycarbonyl-5-de-O-methyl-KA-6606I and 269 mg of an N-hydroxysuccinimide ester of N$^\alpha$-benzyloxycarbonyl-N$^\epsilon$-octyloxycarbonyl-L-lysine were reacted and worked up in the same way as in Example 1, (a). The reaction product was purified by silica gel column chromatography [solvent: chloroform/methanol (50:1)] to give 235 mg of 1,2',6'-tris-N-benzyloxycarbonyl-2''-N-(N$^\alpha$-benzyloxycarbonyl-N$^\epsilon$-octyloxycarbonyl-L-lysyl)-5-de-O-methyl-KA-6606I as a colorless solid.

Specific rotation: $[\alpha]_D^{23} + 29°$ (c=2, CHCl$_3$)
$^1$H-NMR value: $\delta_{CDCl_3}^{TMS}$, ppm
0.89 [3H, t, —(CH$_2$)$_7$—C$\underline{H}_3$]
1.05 (3H, d, J=6.5 Hz, C$^{6'}$—CH$_3$)
2.92 (3H, s, N—CH$_3$)
3.99 (2H, t, J=6 Hz, N$^\epsilon$—COOC$\underline{H}_2$—)
Elemental analysis for C$_{63}$H$_{85}$N$_7$O$_{16}$:

|  | C | H | N |
|---|---|---|---|
| Calculated (%): | 63.25 | 7.16 | 8.20 |
| Found (%): | 62.80 | 7.23 | 7.96 |

(b) The N-protected compound (235 mg) obtained in (a) was reacted and worked up in the same way as in Example 1, (b) to give 140 mg of the hydrochloride of the captioned compound as a colorless solid.

Specific rotation: $[\alpha]_D^{24} + 80°$ (c=5, H$_2$O)
$^1$H-NMR value: $\delta_{D_2O}^{TMS}$, ppm
0.88 [3H, t, —(CH$_2$)$_7$—CH$_3$]
1.36 (3H, d, J=7 Hz, C$^{6'}$—CH$_3$)
3.18 (3H, s, N—CH$_3$)
5.50 (1H, d, J=3.3 Hz, H-1')
Elemental analysis for C$_{31}$H$_{61}$N$_7$O$_8$·4HCl·2H$_2$O:

|  | C | H | N | Cl |
|---|---|---|---|---|
| Calculated (%): | 44.23 | 8.26 | 11.65 | 16.85 |
| Found (%): | 43.65 | 8.53 | 11.38 | 16.59 |

EXAMPLE 8

Production of 2''-N-($\beta$-O-methyl-L-aspartyl)-5-de-O-methyl-KA-666I:

(a) 41 mg of 1,2',6'-tris-N-benzyloxycarbonyl-5-de-O-methyl-KA-6606I and 33 mg of an N-hydroxysuccinimide ester of N-benzyloxycarbonyl-$\beta$-O-methyl-L-aspartic acid were reacted and worked up in the same way as in Example 1, (a). The reaction product was purified by preparative thin-layer chromatography [carrier: silica gel; solvent: chloroform/methanol (10:1)] to give 36 mg of 1,2',6'-tris-N-benzyloxycarbonyl-2''-N-(N-benzyloxycarbonyl-$\beta$-O-methyl-L-aspartyl)-5-de-O-methyl-KA-6606I as a colorless solid.

Specific rotation: $[\alpha]_D^{24} + 37°$ (c=2, CHCl$_3$)
$^1$H-NMR value: $\delta_{CDCl_3}^{TMS}$, ppm
1.04 (3H, d, J=6 Hz, C$^{6'}$—CH$_3$)
2.90, 3.05 (total 3H, s, N—CH$_3$, rotational isomer)
3.61 (3H, s, COOCH$_3$)
Elemental analysis for C$_{53}$H$_{64}$N$_6$O$_{16}$:

|  | C | H | N |
|---|---|---|---|
| Calculated (%): | 61.14 | 6.20 | 8.07 |
| Found (%): | 61.31 | 6.03 | 7.81 |

(b) The N-protected compound (36 mg) obtained in (a) was reacted and worked up in the same way as in Example 1, (b) to give 19 mg of the hydrochloride of the captioned compound as a colorless solid.

Specific rotation: $[\alpha]_D^{24} 30\ 60°$ (c=0.7, H$_2$O)
$^1$H-NMR value: $\delta_{D_2O}^{TMS}$, ppm
1.35 (3H, d, J=7 Hz, C$^{6'}$—CH$_3$)
3.16 (3H, s, N—CH$_3$)
3.78 (3H, s, COOCH$_3$)
5.48 (1H, d, J=3.5 Hz, H-1')
Elemental analysis for C$_{21}$H$_{40}$N$_6$O$_8$·4HCl·2H$_2$O:

|  | C | H | N | Cl |
|---|---|---|---|---|
| Calculated (%): | 36.74 | 7.05 | 12.24 | 20.66 |
| Found (%): | 36.54 | 6.91 | 12.24 | 21.01 |

EXAMPLE 9

Production of 2''-N-($\beta$-O-tert.-butyl-L-aspartyl)-5-de-O-methyl-KA-6606I:

(a) 548 mg of 1,2',6'-tris-N-benzyloxycarbonyl-5-de-O-methyl-KA-6606I and 330 mg of an N-hydroxysuccinimide ester of N-benzyloxycarbonyl-$\beta$-O-tert.-butyl-L-aspartic acid were reacted and worked up in the same way as in Example 1, (a). The reaction product was purified by silica gel column chromatography [solvent: chloroform/methanol (59:1)] to give 260 mg of 1,2',6'-tris-N-benzyloxycarbonyl-2''-N-(N-benzyloxycarbonyl-$\beta$-O-tert.-butyl-L-aspartyl)-5-de-O-methyl-KA-6606I as a colorless solid.

Specific rotation: $[\alpha]_D^{18} + 35°$ (c=1.7, CHCl$_3$)
$^1$H-NMR value: $\delta_{CDCl_3}^{TMS}$, ppm
1.03 (3H, d, J=6 Hz, C$^{6'}$—CH$_3$)
1.38 [9H, s, C(CH$_3$)$_3$]
2.87 (3H, s, N—CH$_3$)
Elemental analysis for C$_{56}$H$_{70}$N$_6$O$_{16}$:

|  | C | H | N |
|---|---|---|---|
| Calculated (%): | 62.09 | 6.51 | 7.76 |
| Found (%): | 61.65 | 6.62 | 7.59 |

(b) 33 mg of the N-protected compound obtained in (a) was reacted and worked up in the same way as in Example 1, (b) to give 19 mg of the hydrochloride of the captioned compound as a colorless solid.

Specific rotation: $[\alpha]_D^{18} + 84°$ (c=0.6, H$_2$O)
$^1$H-NMR value: $\delta_{D_2O}^{TMS}$, ppm
1.35 (3H, d, J=6.7 Hz, C$^{6'}$—CH$_3$)
1.50 [9H, s, C(CH$_3$)$_3$]
3.17 (3H, s, N—CH$_3$)
5.49 (1H, d, J=3.5 Hz, H-1')
Elemental analysis for C$_{24}$H$_{46}$N$_6$O$_8$·4HCl·H$_2$O:

|  | C | H | N | Cl |
|---|---|---|---|---|
| Calculated (%): | 40.57 | 7.38 | 11.83 | 19.96 |
| Found (%): | 40.44 | 7.41 | 11.23 | 20.28 |

EXAMPLE 10

Production of 2''-N-(β-O-octyl-L-aspartyl)-5-de-O-methyl-KA-6606I:

(a) Forty milligrams of the N-protected-β-O-tertbutyl-L-aspartyl compound obtained in Example 9, (a) was dissolved in 0.3 ml of trifluoroacetic acid under ice cooling. The solution was left to stand at the same temperature for 1 hour, and concentrated to dryness. The residue was dissolved in chloroform, and after adding toluene, concentrated to dryness to give 38 mg of a compound resulting from elimination of the tert.-butyl group from the above compound.

The resulting compound was dissolved in 0.33 ml of acetonitrile, and 10.5 mg of dicyclohexylcarbodiimide, 13 mg of n-octyl alcohol, and 0.8 mg of dimethylaminopyridine were added. The mixture was stirred overnight at room temperature. The reaction mixture was worked up in a custormary manner, and then purified by preparative thin-layer chromatography [carrier: silica gel; solvent; chloroform/methanol (10:1)] to give 15.6 mg of 1,2',6'-tris-N-benzyloxycarbonyl-2''-N-(N-benzyloxycarbonyl-β-O-octyl-L-aspartyl)-5-de-O-methyl-KA-6606I as a colorless solid.

Specific rotation: $[\alpha]_D^{23} + 33°$ (c=1, CHCl$_3$)
$^1$H-NMR value: $\delta_{CDCl_3}^{TMS}$, ppm
0.88 [3H, t, —(CH$_2$)$_7$—CH$_3$]
1.05 (3H, d, J=6 Hz, C$^{6'}$—CH$_3$)
2.90 (3H, s, N—CH$_3$)
Elemental analysis for C$_{60}$H$_{78}$N$_6$O$_{16}$:

|  | C | H | N |
|---|---|---|---|
| Calculated (%): | 63.25 | 6.90 | 7.38 |
| Found (%): | 63.21 | 6.63 | 7.17 |

(b) 16 mg of the N-protected compound obtained in (a) was reacted and worked up in the same way as in Example 1, (b) to give 9 mg of the hydrochloride of the captioned compound as a colorless solid.

Specific rotation: $[\alpha]_D^{18} + 78°$ (c=0.4, H$_2$O)
$^1$H-NMR value: $\delta_{D_2O}^{TMS}$, ppm
0.88 [3H, t, —(CH$_2$)$_7$—CH$_3$]
1.32 (s, octyl methylene portion)
1.35 (3H, d, J=6.5 Hz, C$^{6'}$—CH$_3$)
3.17 (3H, s, N—CH$_3$)
5.49 (1H, d, J=3.5 Hz, H-1')
Elemental analysis for C$_{28}$H$_{54}$N$_6$O$_8$·4HCl·2H$_2$O:

|  | C | H | N | Cl |
|---|---|---|---|---|
| Calculated (%): | 42.86 | 7.96 | 10.71 | 18.07 |
| Found (%): | 42.92 | 7.83 | 10.25 | 18.51 |

EXAMPLE 11

Production of 2''-N-(β-O-phenyl-L-aspartyl)-5-de-O-methyl-KA-6606I:

(a) 62 mg of 1,2',6'-tris-N-benzyloxycarbonyl-5-de-O-methyl-KA-6606I and 46 mg of an N-hydroxysuccinimide ester of N-benzyloxycarbonyl-β-O-phenyl-L-aspartic acid were reacted and worked up in the same way as in Example 1, (a). The reaction product was purified by preparative thin-layer chromatography [carrier: silica gel; solvent; chloroform/methanol (15:1)] to give 34 mg of 1,2',6'-tris-N-benzyloxycarbonyl-2''-N-(N-benzyloxycarbonyl-β-O-phenyl-L-aspartyl)-5-de-O-methyl-KA-6606I as a colorless solid.

Specific rotation: $[\alpha]_D^{25} + 35°$ (c=1, CHCl$_3$)
$^1$H-NMR value: $\delta_{CDCl_3}^{TMS}$, ppm
1.05 (3H, d, J=7 Hz, C$^{6'}$—CH$_3$)
2.91 (3H, s, N—CH$_3$)

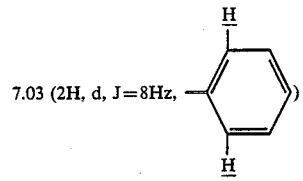

7.03 (2H, d, J=8Hz, —)

Elemental analysis for C$_{58}$H$_{66}$N$_6$O$_{16}$:

|  | C | H | N |
|---|---|---|---|
| Calculated (%): | 63.15 | 6.03 | 7.62 |
| Found (%): | 63.08 | 6.31 | 7.54 |

(b) 26 mg of the N-protected compound obtained in (a) was reacted and worked up in the same way as in Example 1, (b) to give 14 mg of the hydrochloride of the captioned compound as a colorless solid.

Specific rotation: $[\alpha]_D^{24} + 66°$ (c=1, H$_2$O)
$^1$H-NMR value: $\delta_{D_2O}^{TMS}$, ppm
1.34 (3H, d, J=6.7 Hz, C$^{6'}$—CH$_3$)
3.18 (2H, s, N—CH$_3$)

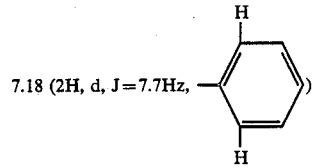

7.18 (2H, d, J=7.7Hz, —)

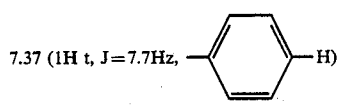

7.37 (1H t, J=7.7Hz, —H)

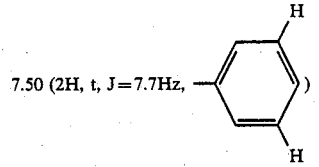

7.50 (2H, t, J=7.7Hz, —)

Elemental analysis for C$_{26}$H$_{42}$N$_6$O$_8$ 4HCl 3/2H$_2$O:

|  | C | H | N | Cl |
|---|---|---|---|---|
| Calculated (%): | 42.23 | 6.68 | 11.36 | 19.18 |
| Found (%): | 42.05 | 6.68 | 10.87 | 19.22 |

EXAMPLE 12

Production of 2''-N-[β-O-(α-naphthyl)-L-aspartyl]-5-de-O-methyl-KA-6606I:

(a) 156 mg of 1,2',6'-tris-N-benzyloxycarbonyl-5-de-O-methyl-KA-6606I and 105 mg of an N-hydroxysuccinimide ester of N-benzyloxycarbonyl-β-O-(α-naphthyl)-L-aspartic acid were reacted and worked up in the same way as in Example 1, (a). The reaction product was purified by preparative thin-layer chromatography [carrier: silica gel; solvent: chloroform/methanol (13:1)]

to give 117 mg of 1,2',6'-tris-N-benzyloxycarbonyl-2''-N-[N-benzyloxy-carbonyl-β-O-(α-napthyl)-L-aspartyl]-5-de-O-methyl-KA-6606I as a colorless solid.

Specific rotation: $[\alpha]_D^{25} +30°$ (c=1, CHCl$_3$)

$^1$H-NMR value: $\delta_{CDCl_3}^{TMS}$, ppm 1.00 [3H, d, J=6 Hz, C$^{6'}$—CH$_3$)
2.84 (3H, s, N—CH$_3$)
7.1–7.9 (27H, aromatic H)

Elemental analysis for C$_{62}$H$_{68}$N$_6$O$_{16}$:

|  | C | H | N |
|---|---|---|---|
| Calculated (%): | 64.57 | 5.94 | 7.29 |
| Found (%): | 64.31 | 5.81 | 6.88 |

(b) 70 mg of the N-protected compound obtained in (a) was reacted and worked up in the same way as in Example 1, (b) to give 40 mg of the hydrochloride of the captioned compound as a colorless solid.

Specific rotation: $[\alpha]_D^{20} +61°$ (c=2, H$_2$O)

$^1$H-NMR value: $\delta_{D_2O}^{TMS}$, ppm 1.34 (3H, d, J=7 Hz, C$^{6'}$—CH$_3$)
3.20 (1H, s, N—CH$_3$)
7.4–8.1 (9H, m, α-naphthyl group)

Elemental analysis for C$_{30}$H$_{44}$N$_6$O$_8$·4HCl·2H$_2$O:

|  | C | H | Cl |
|---|---|---|---|
| Calculated (%): | 45.12 | 6.56 | 10.52 | 17.76 |
| Found (%): | 44.77 | 6.59 | 10.18 | 17.96 |

EXAMPLE 13

Production of 2''-N-[β-O-(3-stearoyloxy-2-hydroxypropyl)-L-aspartyl]-5-de-O-methyl-KA-6606I:

(a) 68 mg of the tert.-butyl-eliminated compound obtained by the procedure of the first half of Example 10, (a) and 70 mg of mono-olein were reacted and worked up by the same procedure as in the latter half of Example 10, (a). The reaction product was purified by silica gel column chromatography (solvent: ethyl acetate) to give 49 mg of 1,2',6'-tris-N-benzyloxycarbonyl-2''-N-[N-benzyloxy-carbonyl-β-O-(3-oleoyloxy-2-hydroxypropyl)-L-aspartyl]-5-de-O-methyl-KA-6606I as a colorless solid.

Specific rotation: $[\alpha]_D^{23} +31°$ (c=2, CHCL$_3$)

$^1$H-NMR value: $\delta_{CDCl_3}^{TMS}$, ppm 0.90 (3H, t, oleoyl-CH$_3$)
1.04 (3H, br.s, C$^{6'}$—CH$_3$)
5.33 (2H, t, olefinic H)

Elemental analysis for C$_{73}$H$_{100}$N$_6$O$_{19}$:

|  | C | H | N |
|---|---|---|---|
| Calcullated (%): | 64.20 | 7.38 | 6.15 |
| Found (%): | 64.13 | 7.16 | 5.95 |

(b) 36 mg of the N-protected compound obtained in (a) was reacted and worked up in the same way as in Example 1, (b) to give 16 mg of the hydrochloride of the captioned compound as a colorless solid.

Specific rotation: $[\alpha]_D^{24} +70°$ (c=1, H$_2$O)

$^1$H-NMR value: $\delta_{D_2O}^{TMS}$, ppm 0.87 [3H, t, —(CH$_2$)$_{16}$—CH$_3$]
1.28 (s, stearoyl methylene portion H)
1.36 (3H, d, J=6.5 Hz, C$^{6'}$—CH$_3$)
5.47 (1H, br.s, H-1')

Elemental analysis for C$_{41}$H$_{78}$N$_6$O$_{11}$·4HCl·2H$_2$O:

|  | C | H | N | Cl |
|---|---|---|---|---|
| Calculated (%): | 39.68 | 7.21 | 11.57 | 19.52 |
| Found (%): | 39.25 | 7.33 | 11.28 | 19.49 |

EXAMPLE 14

Production of 2''-N-[γ-O-(3-hydroxypropyl)-L-glutamyl]-5-de-O-methyl-KA-6606I:

(a) 1.17 g of 1,2',6'-tris-N-benzyloxycarbonyl-5-de-O-methyl-KA-6606I and 730 mg of an N-hydroxysuccinimide ester of N-benzyloxycarbonyl-γ-O-tert.-butyl-L-glutamic acid were reacted and worked up in the same way as in Example 1, (a). The reaction product was purified by silica gel column chromatography [solvent: chloroform/methanol (40:1)] to give 844 mg of 1,2',6'-tris-N-benzyloxycarbonyl-2''-N-(N-benzyloxycarbonyl-γ-O-tert.-butyl-L-glutamyl)-5-de-O-methyl-KA-6606I as a colorless solid.

Specific rotation: $[\alpha]_D^{18} +54°$ (c=1, CHCl$_3$)

$^1$H-NMR value: $\delta_{CDCl_3}^{TMS}$, ppm 1.03 (3H, d, J=7 Hz, C$^{6'}$—CH$_3$)
1.41 [9H, s, C(CH$_3$)$_3$]
2.88 (3H, s, N—CH$_3$)

Elemental analysis for C$_{57}$H$_{72}$N$_6$O$_{16}$:

|  | C | H | N |
|---|---|---|---|
| Calculated (%): | 62.40 | 6.61 | 7.66 |
| Found (%): | 62.13 | 6.88 | 7.32 |

(b) Forty milligrams of the N-protected-γ-O-tert.-butyl-L-glutamyl compound obtained in (a) was reacted and worked up in the same way as in the first half of Example 10, (a) to give 38 mg of a compound resulting from elimination of the tert.-butyl group from the above compound.

The above free carboxylic acid (38 mg) and 0.05 ml of 1,3-propanediol were reacted and worked up in the same way as in the latter half of Example 10, (s). The reaction product was purified by preparative thin-layer chromatography [carrier: silica gel; solvent: chloroform/ethyl acetate/acetone (1:1:1)] to give 25 mg of 1,2',6'-tris-N-benzyloxycarbonyl-2''-N-[N-benzyloxycarbonyl-γ-O-(3-hydroxypropyl)-L-glutamyl]-5-de-O-methyl-KA-6606I.

Specific rotation: $[\alpha]_D^{24} +30°$ (c=1, CHCl$_3$)

$^1$H-NMR value: $\delta_{CDCl_3}^{TMS}$, ppm 1.04 (3H, d, J=6 Hz, C$^{6'}$—CH$_3$)
2.91 (3H, s, N—CH$_3$)

Elemental analysis for C$_{56}$H$_{70}$N$_6$O$_{17}$:

|  | C | H | N |
|---|---|---|---|
| Calculated (%): | 61.19 | 6.42 | 7.76 |
| Found (%): | 60.88 | 6.31 | 7.22 |

(c) 24 mg of the N-protected compound obtained in (b) was reacted and worked up in the same way as in Example 1, (b) to give 10 mg of the hydrochloride of the captioned compound as a colorless solid.

Specific rotation: $[\alpha]_D^{24} +54°$ (c=0.5, H$_2$O)

$^1$H-NMR value: $\delta_{D_2O}^{TMS}$, ppm 1.34 (3H, d, J=6.7 Hz, C$^{6'}$—CH$_3$)
1.91 (2H, quint, J=6.7 Hz, —O—CH$_2$—C$\underline{H_2}$—CH$_2$—O—)
3.17 (3H, s, N—CH$_3$)

5.48 (1H, d, J=3.5 Hz, H-1′)
Elemental analysis for $C_{24}H_{46}N_6O_9 \cdot 4HCl \cdot H_2O$:

|  | C | H | N | Cl |
|---|---|---|---|---|
| Calculated (%): | 39.68 | 7.21 | 11.57 | 19.52 |
| Found (%): | 39.77 | 6.89 | 10.86 | 19.72 |

EXAMPLE 15

Production of 2″-N-[γ-O-(2-decanoyloxyethyl)-L-glutamyl]-5-de-O-methyl-KA-6606I:

(a) 78 mg of 1,2′,6′-tris-N-benzyloxycarbonyl-5-de-O-methyl-KA-6606I and 55 mg of an N-hydroxysuccinimide ester of N-benzyloxycarbonyl-γ-(2-decanoyloxyethyl)-L-glutamic acid were reacted and worked up in the same way as in Example 1, (a). The reaction product was purified by preparative thin-layer chromatography [carrier: silica gel; solvent: chloroform/methanol (10:1)] to give 66 mg of 1,2′,6′-tris-N-benzyloxycarbonyl-2″-N-[N-benzyloxycarbonyl-γ-O-(2-decanoyloxyethyl)-L-glutamyl]-5-de-O-methyl-KA-6606I as a colorless solid.

Specific rotation: $[\alpha]_D^{26}$ +26° (c=1, CHCl$_3$)
IR value: $\nu_{max}^{CHCl_3}$, cm$^{-1}$
1710 (urethane, ester) 1635 (amide I),
1500 (amide II)
$^1$H-NMR value: $_{CDCl_3}^{TMS}$, ppm
0.87 [3H, t, —(CH$_2$)$_8$—C$\underline{H}_3$]
1.02 (3H, d, J=7 Hz, C$^{6'}$—CH$_3$)
1.26 (br.s, decanoyl methylene portion)
~7.3 (20H, aromatic H)
Elemental analysis for $C_{65}H_{86}N_6O_{18}$:

|  | C | H | N |
|---|---|---|---|
| Calculated (%): | 62.99 | 6.99 | 6.78 |
| Found (%): | 63.21 | 7.12 | 6.68 |

(b) 62 mg of the N-protected compound obtained in (a) was reacted and worked up in the same way as in Example 1, (b) to give 40 mg of the hydrochloride of the captioned compound as a colorless solid.

Specific rotation: $[\alpha]_D^{24}$ +50° (c=1, H$_2$O)
$^1$H-NMR value: $\delta_{D_2O}^{TMS}$, ppm
0.89 [3H, t, —(CH$_2$)$_8$—C$\underline{H}_3$]
1.31 (br.s, decanoyl methylene portion)
1.37 (3H, d, J=7 Hz, C$^{6'}$—CH$_3$)
3.19 (3H, s, N—CH$_3$)
5.51 (1H, d, J=3.5 Hz, H-1′)
Elemental analysis for $C_{33}H_{62}N_6O_{10} \cdot 4HCl \cdot 2H_2O$:

|  | C | H | N | Cl |
|---|---|---|---|---|
| Calculated (%): | 44.80 | 7.97 | 9.50 | 16.03 |
| Found (%): | 44.53 | 7.79 | 9.63 | 16.28 |

EXAMPLE 16

Production of 2″-N-{γ-O-[2-(1,3-bis-decanoyloxy)propyl]-L-glutamyl}-5-de-O-methyl-KA-6606I:

(a) Fifty milligrams of the free carboxylic acid obtained by the procedure of the first half of Example 14, (b) and 29 mg of 1,3-didecanoylglycerol were reacted and worked up by the same procedure as the latter half of Example 10, (a). The reaction product was purified by preparative thin-layer chromatography [carrier: silica gel; solvent: benzene/acetone (3:2)] to give 8 mg of 1,2′,6′-tris-N-benzyloxycarbonyl-2″-N-{N-benzyloxycarbonyl-γ-O-[2-(1,3-bis-decanoyloxy)propyl]-L-glutamyl}-5-de-O-methyl-KA-6606I as a colorless solid.

Specific rotation: $[\alpha]_D^{20}$ +23° (c=0.5, CHCl$_3$)
$^1$H-NMR value: $\delta_{CDCl_3}^{TMS}$, ppm
0.88 [6H, t, —(CH$_2$)$_8$—CH$_3$×2]
1.06 (3H, d, J=7 Hz, C$^{6'}$—CH$_3$)
2.92 (3H, s, N—CH$_3$)
Elemental analysis for $C_{76}H_{106}N_6O_{20}$:

|  | C | H | N |
|---|---|---|---|
| Calculated (%): | 64.12 | 7.50 | 5.90 |
| Found (%): | 63.18 | 7.44 | 5.43 |

(b) The N-protected compound (8 mg) obtained in (a) was reacted and worked up in the same way as in Example 1, (b) to give 3 mg of the hydrochloride of the captioned compound as a colorless solid.

Specific rotation: $[\alpha]_D^{18}$ +33° (c=0.2, H$_2$O)
$^1$H-NMR value: $\delta_{D_2O}^{TMS}$, ppm
0.90 [6H, t, —(CH$_2$)$_8$—CH$_3$×2]
1.32 (s, decanoyl methylene portion)
1.38 (3H, d, J=6.5 Hz, C$^{6'}$—CH$_3$)
3.20 (3H, s, N—CH$_3$)
5.52 (1H, d, J=3 Hz, H-1′)
Elemental analysis for $C_{44}H_{82}N_6O_{12} \cdot 4HCl \cdot 2H_2O$:

|  | C | H | N | Cl |
|---|---|---|---|---|
| Calculated (%): | 49.43 | 8.49 | 7.86 | 13.27 |
| Found (%): | 48.96 | 8.31 | 7.77 | 13.41 |

EXAMPLE 17

Production of 2″-N-[γ-O-(2,3-bis-decanoyloxypropyl)-L-glutamyl]-5-de-O-methyl-KA-66606I:

(a) Fifty milligrams of the free carboxylic acid obtained in the first half of Example 14, (b) and 29 mg of 1,2-didecanoylglycerol were reacted and worked up by the same procedure as in the latter half of Example 10, (a). The reaction product was purified by preparative thin-layer chromatography [carrier: silica gel; sovlent: benzene/acetone (1:1)] to give 18 mg of 1,2′,6′-tris-N-benzyloxycarbonyl-2″-N-[N-benzylolxycarbonyl-γ-O-(2,3-bis-decanoyloxypropyl)-L-glutamyl]-5-de-methyl-KA-6606I as a colorless solid.

Specific rotation: $[\alpha]_D^{22}$ +23° (c=1, CHCl$_3$)
$^1$H-NMR value: $\delta_{CDCl_3}^{TMS}$, ppm
0.88 [6H, t, —(CH$_2$)$_8$—CH$_3$×2]
1.06 (3H, d, J=7 Hz, C$^{6'}$—CH$_3$)
2.92 (3H, s, N—CH$_3$)
Elemental analysis for $C_{76}H_{106}N_6O_{20}$:

|  | C | H | N |
|---|---|---|---|
| Calculated (%): | 64.12 | 7.50 | 5.90 |
| Found (%): | 64.28 | 7.66 | 5.63 |

(b) 16 mg of the N-protected compound obtained in (a) was reacted and worked up in the same way as in Example 1, (b) to give 10 mg of the hydrochloride of the captioned compound as a colorless solid.

Specific rotation: $[\alpha]_D^{22}$ +48° (c=0.5, H$_2$O)
$^1$H-NMR value: $\delta_{D_2O}^{TMS}$, ppm
0.92 [6H, t, —(CH$_2$)$_8$—CH$_3$×2]
1.33 (s, decanoyl methylene portion)
1.39 (3H, d, J=6.5 Hz, C$^{6'}$—CH$_3$)
3.24 (3H, s, N—CH$_3$)

5.53 (1H, d, J=3.5 Hz, H-1')
Elemental analysis for C$_{44}$H$_{82}$N$_6$O$_{12}$.4HCl.2H$_2$O:

|  | C | H | N | Cl |
|---|---|---|---|---|
| Calculated (%): | 49.43 | 8.49 | 7.86 | 13.27 |
| Found (%): | 48.96 | 8.52 | 7.51 | 13.49 |

EXAMPLE 18

Production of 2''-N-[γ-O-(3-decanoyloxypropyl)-L-glutamyl]-5-de-O-methyl-KA-6606I:

(a) Fifty milligrams of the free carboxylic acid obtained in the first half of Example 14, (b) and 17 mg of 3-decanoyloxypropanol were reacted and worked up in the same way as in the latter half of Example 10, (a). The reaction product was purified by preparative thin-layer chromatography [carrier: silica gel; solvent: benzene/-acetone (3:2)] to give 9 mg of 1,2',6'-tris-N-benzyloxycarbonyl-2''-N-[N-benzyloxycarbonyl-γ-O-(3-decanoyloxypropyl)-L-glutamyl]-5-de-O-methyl-KA-6606I as a colorless solid.

Specific rotation: $[\alpha]_D^{20}$ +28° (c=0.5, CHCl$_3$)
$^1$H-NMR value: $\delta_{CDCl_3}^{TMS}$, ppm
0.88 [3H, t, —(CH$_2$)$_8$—CH$_3$]
1.06 (3H, d, J=6.5 Hz, C$^{6'}$—CH$_3$)
1.28 (s, decanoyl methylene portion)
2.84, 2.96 (total 3H, s, N—CH$_3$, rotational isomer)
Elemental analysis for C$_{66}$H$_{88}$N$_6$O$_{18}$:

|  | C | H | N |
|---|---|---|---|
| Calculated (%): | 63.24 | 7.08 | 6.71 |
| Found (%): | 62.53 | 7.13 | 6.28 |

(b) The N-protected compound (9 mg) obtained in (a) was reacted and worked up in the same way as in Example 1, (b) to give 4 mg of the hyrochloride of the captioned compound as a colorless solid.

Specific rotation: $[\alpha]_D^{24}$ +68° (c=4, H$_2$O)
$^1$H-NMR value: $\delta_{D_2O}^{TMS}$, ppm
0.91 [3H, t, —(CH$_2$)$_8$—CH$_3$]
1.33 (s, decanoyl methylene portion)
1.38 (3H, d, J=6.5 Hz, C$^{6'}$—CH$_3$)
3.21 (3H, s, N—CH$_3$)
5.51 (1H, d, J=3.5 Hz, H-1')
Elemental analysis for C$_{34}$H$_{64}$N$_6$O$_{10}$.4HCl.3/2H$_2$O:

|  | C | H | N | Cl |
|---|---|---|---|---|
| Calculated (%): | 45.89 | 8.04 | 9.45 | 15.94 |
| Found (%): | 45.52 | 7.95 | 9.16 | 16.20 |

EXAMPLE 19

Production of 2''-N-[γ-O-(3-stearoyloxypropyl)-L-glutamyl]-5-de-O-methyl-KA-6606I:

(a) 43 mg of the free carboxylic acid obtained in the first half of Example 14, (b) and 28 mg of 3-oleoyloxypropanol were reacted and worked up in the same way as in the latter half of Example 10, (a). The reaction product was purified by preparative thin-layer chromatography [carrier: silica gel; solvent: chloroform/methanol (10:1)] to give 12 mg of 1,2',6'-tris-N-benzyloxycarbonyl-2''-N-[N-benzyloxycarbonyl-γ-O-(3-oleoyloxypropyl)-L-glutamyl]-5-de-O-methyl-KA-6606I as a colorless solid.

Specific rotation: $[\alpha]_D^{19}$+30° (c=0.61, CHCl$_3$)
IR value: $\nu_{max}^{CHCl_3}$, cm$^{-1}$ 1635 (amide I)
$^1$H-NMR value: $\delta_{CDCl_3}^{TMS}$, ppm
0.8–0.96 [3H, —CH=CH—(CH$_2$)$_7$—CH$_3$]
1.03 (3H, br.s, C$^{6'}$—CH$_3$)
Elemental analysis for C$_{74}$H$_{102}$N$_6$O$_{18}$:

|  | C | H | N |
|---|---|---|---|
| Calculated (%): | 65.18 | 7.54 | 6.16 |
| Found (%): | 64.92 | 7.77 | 6.09 |

(b) The N-protected compound (12 mg) obtained in (a) was reacted and worked up in the same way as in Example 1, (b) to give 7.7 mg of the hydrochloride of the captioned compound as a colorless solid.

Specific rotation: $[\alpha]_D^{19}$+58° (c=0.33, H$_2$O)
IR value: $\nu_{max}^{KBr}$, cm$^{-1}$ 1720 (shoulder, ester), 1680 (amide I)
$^1$H-NMR value: $\delta_{D_2O}^{TMS}$, ppm
0.88 [3H, t, —(CH$_2$)$_{16}$—CH$_3$]
3.17 (3H, s, N—CH$_3$)
5.48 (1H, br.s, H-1')
Elemental analysis for C$_{42}$H$_{80}$N$_6$O$_{10}$.4HCl.2H$_2$O:

|  | C | H | N | Cl |
|---|---|---|---|---|
| Calculated (%): | 49.90 | 8.77 | 8.31 | 14.03 |
| Found (%): | 49.95 | 9.03 | 7.98 | 14.51 |

EXAMPLE 20

Production of 2''-N-[γ-O-(3-deoxycholyloxypropyl)-L-glutamyl]-5-de-O-methyl-KA-6606I:

(a) 49 mg of the free carboxylic acid obtained in the first half of Example 14, (b) and 28 mg of 3-(deoxycholyloxy)propanol were reacted and worked up in the same way as in the latter half of Example 10, (a). The reaction product was purified by preparative thin-layer chromatography [carrier: silica gel: sovlent: chloroform/methanol (7:1)] to give 12 mg of 1,2',6'-tris-N-benzyloxycarbonyl-2''-N-[N-benzyloxycarbonyl-γ-O-(3-deoxycholyloxypropyl)-L-glutamyl]-5-de-O-methyl-KA-6606I as a colorless syrup.

Specific rotation: $[\alpha]_D^{18}$+37° (c=0.58 CHCl$_3$)
IR value: $\nu_{max}^{CHCl_3}$, cm$^{-1}$ 1637 (amide I)
$^1$H-NMR value: $\delta_{CDCl_3}^{TMS}$, ppm
0.66 (3H, s, deoxycholyl CH$_3$-18)
0.89 (3H, s, deoxycholyl CH$_3$-19)
0.95 (3H, d, J=6 Hz, deoxycholyl CH$_3$-21)
1.04 (3H, br.d, J=7 Hz, C$^{6'}$—CH$_3$)
2.93, 3.08 (total 3H, s, N—CH$_3$, rotational isomer)
Elemental analysis for C$_{80}$H$_{108}$N$_6$O$_{20}$:

|  | C | H | N |
|---|---|---|---|
| Calculated (%): | 65.20 | 7.39 | 5.70 |
| Found (%): | 64.97 | 7.67 | 5.50 |

(b) The N-protected compound (12 mg) obtained in (a) was reacted and worked up in the same way as in Example 1, (b) to give 7.6 mg of the hydrochloride of the captioned compound as a colorless solid.

Specific rotation: $[\alpha]_D^{19}$+71° (c=0.38, H$_2$O)
IR value: $\nu_{max}^{KBr}$, cm$^{-1}$ 1720 (ester), 1680 (amide I)
$^1$H-NMR value: $\delta_{D_2O}^{TMS}$, ppm
0.70 (3H, s, deoxycholyl CH$_3$-18)
0.92 (3H, s, deoxycholyl CH$_3$-19)
0.97 (3H, d, J=6 Hz, deoxycholyl CH$_3$-21)

1.34 (3H, d, J=7 Hz, C$^{6'}$—CH$_3$)
3.16 (3H, s, N—CH$_3$)
5.47 (1H, d, J=3.5 Hz, H-1')
Elemental analysis for C$_{48}$H$_{84}$N$_6$O$_{12}$.4HCl.2H$_2$O:

|  | C | H | N | Cl |
|---|---|---|---|---|
| Calculated (%): | 51.52 | 8.29 | 7.51 | 12.67 |
| Found (%): | 52.01 | 8.33 | 7.24 | 12.98 |

EXAMPLE 21

Production of 2''-N-{γ-O-[4-(α-naphthoyloxy)butyl]-L-glutamyl}-5-de-O-methyl-KA-6606I:

(a) 665 mg of the free carboxylic acid obtained in the first half of Example 14, (b) and 335 mg of (α-naphthoyloxy)-1-butanol were reacted and worked up in the same way as in the latter half of Example 10, (a). The reaction product was purified by silica gel column chromatography [solvent: chloroform/ethyl acetate/acetone (5:4:2→2:2:1) to give 350 mg of 1,2',6'-tris-N-benzyloxycarbonyl-2''-N-{N-benzyloxycarbonyl-γ-[4-(α-naphthoyloxy)butyl]-L-glutamyl}-5-de-O-methyl-KA-6606I.

Specific rotation: [α]$_D^{21}$+28° (c=1 CHCl$_3$)
IR value: ν$_{max}^{CHCl_3}$, cm$^{-1}$ 1710 (urethane, ester), 1635 (amide I), 1500 (amide II)
$^1$H-NMR value: δ$_{CDCl_3}^{TMS}$, ppm
1.00 (3H, d, J=7 Hz, C$^{6'}$—CH$_3$)
~7.3 (20H, phenyl group H)
7.45–7.65 (2H, m, naphthyl H)
7.8–8.1 (4H, m, naphthyl H)
8.57 (1H, s, naphthyl H)
Elemental analysis for C$_{68}$H$_{78}$N$_6$O$_{18}$:

|  | C | H | N |
|---|---|---|---|
| Calculated (%): | 64.44 | 6.20 | 6.63 |
| Found (%): | 64.69 | 6.33 | 6.40 |

(b) The N-protected compound (350 mg) obtained in (a) was reacted and worked up in the same way as in Example 1, (b) to give 126 mg of the hydrochloride of the captioned compound as a colorless solid.

Specific rotation: [α]$_D^{22}$+43° (c=1, H$_2$O)
IR value: ν$_{max}^{KBr}$, cm$^{-1}$ 1680 (ester), 1610 (amide I)
$^1$H-NMR value: δ$_{D_2O}^{TMS}$, ppm
1.36 (3H, d, J=7 Hz, C$^{6'}$—CH$_3$)
3.10 (3H, s, N—CH$_3$)
5.48 (1H, d, J=3.5 Hz, H-1')
7.5–7.75 (2H, m, naphthyl H)
7.8–8.0 (4H, m, naphthyl H)
8.36 (1H, s, naphthyl H)
Elemental analysis for C$_{36}$H$_{54}$N$_6$O$_{10}$.4HCl.2H$_2$O:

|  | C | H | N | Cl |
|---|---|---|---|---|
| Calculated (%): | 47.37 | 6.85 | 9.21 | 15.54 |
| Found (%): | 47.70 | 7.01 | 9.32 | 15.33 |

EXAMPLE 22

Production of 2''-N-{γ-[3,4-bis-(decanoyloxy)butyl]-L-glutamyl}-5-de-O-methyl-KA-6606I:

(a) Fifty milligrams of the free carboxylic acid obtained in the first half of Example 14, (b) and 38 mg of 3,4-bis-(decanoyloxy)-1-butanol were reacted and worked up in the same way as in the latter half of Example 10, (a). The reaction product was purified by preparative thin-layer chromatography [carrier: silica gel; solvent: chloroform/ethyl acetate/acetone (2:2:1)] to give 16 mg of 1,2',6'-tris-N-benzyloxycarbonyl-2''-N-}N-benzyloxycarbonyl-γ-[3,4-bis-(decanoyloxybutyl]-L-glutamyl}-5-de-O-methyl-KA-6606I as a colorless solid.

Specific rotation: [α]$_D^{19}$+36° (c=1, CHCl$_3$)
IR value: ν$_{max}^{CHCl_3}$, cm$^{-1}$ 1710 (urethane, ester), 1630 (amide I), 1495 (amide II)
$^1$H-NMR value: δ$_{CDCl_3}^{TMS}$, ppm
0.87 [6H, t, —(CH$_2$)$_8$—CH$_3$]
1.03 (3H, d, J=7 Hz, C$^{6'}$—CH$_3$)
1.25 (br.s, decanoyl methylene portion)
~7.3 (20H, aromatic H)
Elemental analysis for C$_{77}$H$_{108}$N$_6$O$_{20}$:

|  | C | H | N |
|---|---|---|---|
| Calculated (%): | 64.33 | 7.57 | 5.85 |
| Found (%): | 64.52 | 7.73 | 5.57 |

(b) Fifteen milligrams of the N-protected compound obtained in 9, (a) was reacted and worked up in the same way as in Example 1, (b) to give 8 mg of the hydrochloride of the captioned compound as a colorless solid.

Specific rotation: [α]$_D^{22}$+40° (c=0.25, H$_2$O)
IR value: ν$_{max}^{KBr}$, cm$^{31\ 1}$ 1735 (ester), 1625 (amide I)
$^1$H-NMR value: δ$_{D_2O}^{TMS}$, ppm
0.92 [6H, t, —(CH$_2$)$_7$—CH$_3$]
1.31 (br.s, decanoyl methylene portion)
1.39 (3H, d, J=7 Hz, C$^{6'}$—CH$_3$)
3.22 (3H, s, N—CH$_3$)
5.52 (1H, br.s, H-1')
Elemental analysis for C$_{45}$H$_{84}$N$_6$O$_{12}$.4HCl.H$_2$O:

|  | C | H | N | Cl |
|---|---|---|---|---|
| Calculated (%): | 50.75 | 8.50 | 7.89 | 13.31 |
| Found (%): | 50.51 | 8.77 | 7.63 | 13.09 |

EXAMPLE 23

Production of 2''-N-{γ-[5,6-bis-(decanoyloxy)hexyl]-L-glutamyl}-5-de-O-methyl-KA-6606I:

(a) Fifty milligrams of the free carboxlic acid obtained in the first half of Example 14, (b) and 39 mg of 5,6-bis-(decanoyloxy)-1-hexanol were reacted and worked up in the same way as in the latter half of Example 10, (a) to give 17 mg of 1,2',6'-tris-N-benzyloxycarbonyl-2''-N-{N-benzyloxycarbonyl-γ-[5,6-bis-(decanoyloxy)-hexyl]-L-glutamyl}-5-de-O-methyl-KA-6606I as a colorless solid.

Specific rotation: [α]$_D^{19}$+26° (c=1, CHCl$_3$)
IR value: ν$_{max}^{CHCl_3}$, cm$^{-1}$ 1710 (urethane, ester), 1635 (amide I) $^1$H-NMR value: δ$_{CDCl_3}^{TMS}$, ppm
0.87 [6H, t, —(CH$_2$)$_8$—CH$_3$]
1.03 (3H, d, J=7 Hz, C$^{6'}$—CH$_3$)
1.26 (br.s, decanoyl methylene portion)
~7.3 (20H, aromatic H)
Elemental analysis for C$_{79}$H$_{112}$N$_6$O$_{20}$:

|  | C | H | N |
|---|---|---|---|
| Calculated (%): | 64.73 | 7.70 | 5.73 |
| Found (%): | 65.01 | 7.83 | 5.54 |

(b) Fifteen milligrams of the N-protected compound obtained in (a) was reacted and worked up in the same way as in Example 1, (b) to give 10 mg of the hydrochloride of the captioned compound as a colorless solid.

Specific rotation: $[\alpha]_D^{22}+53°$ (c=1, H$_2$O)
IR value: $\nu_{max}^{KBr}$, cm$^{-1}$ 1730 (ester), 1620 (amide I)
$^1$H-NMR value: $\delta_{D_2O}^{TMS}$, ppm
0.91 [6H, t, —(CH$_2$)$_8$—C$\underline{H}_3$]
1.32 (br.s, decanoyl methylene portion)
1.38 (3H, d, J=7 Hz, C$^{6'}$—CH$_3$)
3.20 (3H, s, N—CH$_3$)
5.52 (1H, br.s, H-1')
Elemental analysis for C$_{47}$H$_{88}$N$_6$O$_{12}$·4HCl·2H$_2$O:

|  | C | H | N | Cl |
|---|---|---|---|---|
| Calculated (%): | 50.81 | 8.71 | 7.56 | 12.76 |
| Found (%): | 51.02 | 8.88 | 7.31 | 12.49 |

EXAMPLE 24

Production of 2''-N-[γ-O-(4-stearoyloxybutyl)-L-glutamyl]-5-de-O-methyl-KA-6606I:

(a) Fifty milligrams of the free carboxylic acid obtained in the first half of Example 14, (b) and 30 mg of 4-hydroxybutyl oleate were reacted and worked up in the same way as in the latter half of Example 10, (a). The reaction product was purified by preparative thin-layer chromatography [carrier: silica gel; solvent: chloroform/ethyl acetate/acetone (2:2:1)] to give 11 mg of 1,2',6'-tris-N-benzyloxycarbonyl-2''-N-[N-benzyloxycarbonyl-γ-O-(4-oleoyloxybutyl)-L-glutamyl]-5-de-O-methyl-KA-6606I as a colorless solid.

Specific rotation: $[\alpha]_D^{18}+26°$ (c=0.5, CHCl$_3$)
$^1$H-NMR value: $\delta_{CDCl_3}^{TMS}$, ppm
0.88 [3H, t, —(CH$_2$)$_7$—C$\underline{H}_3$]
1.04 (3H, d, J=7 Hz, C$^{6'}$—CH$_3$)
2.90 (3H, s, N—CH$_3$)
5.32 (2H, t, —CH=CH—)
Elemental analysis for C$_{75}$H$_{104}$N$_6$O$_{18}$:

|  | C | H | N |
|---|---|---|---|
| Calculated (%): | 65.39 | 7.61 | 6.10 |
| Found (%): | 64.66 | 7.29 | 6.03 |

(b) The N-protected compound (11 mg) obtained in (a) was reacted and worked up in the same way as in Example 1, (b) to give 7.8 mg of the hydrochloride of the captioned compound as a colorless solid.

Specific rotation: $[\alpha]_D^{18}+67°$ (c=0.35, H$_2$O)
$^1$H-NMR value: $\delta_{D_2O}^{TMS}$, ppm
0.88 [3H, t, —(CH$_2$)$_{16}$—C$\underline{H}_3$]
1.28 (s, stearoyl methylene portion)
1.34 (3H, d, J=7 Hz, C$^{6'}$—CH$_3$)
3.17 (3H, s, N—CH$_3$)
5.47 (1H, br.s, H-1')
Elemental analysis for C$_{43}$H$_{82}$N$_6$O$_{10}$·4HCl·3H$_2$O:

|  | C | H | N | Cl |
|---|---|---|---|---|
| Calculated (%): | 49.51 | 8.89 | 8.06 | 13.60 |
| Found (%): | 48.87 | 8.63 | 7.84 | 13.35 |

EXAMPLE 25

Production of 2''-N-[γ-O-(6-stearoyloxyhexyl)-L-glutamyl]-5-de-O-methyl-KA-6606I:

(a) 51 mg of the free carboxylic acid obtained in the first half of Example 14, (b) and 35 mg of 6-hydroxyhexyloleate were reacted and worked up in the same way as in the latter half of Example 10, (a). The reaction product was purified by preparative thin-layer chromatography [carrier: silica gel; solvent: chloroform/ethyl acetate/acetone (2:2:1)] to give 13 mg of 1,2',6'-tris-N-benzyloxycarbonyl-2''-N-[N-benzyloxycarbonyl-γ-O-(6-oleoyloxyhexyl)-L-glutamyl]-5-de-O-methyl-KA-6606I as a colorless solid.

Specific rotation: $[\alpha]_D^{22}+24°$ (c=0.5, CHCl$_3$)
$^1$H-NMR value: $\delta_{CDCl_3}^{TMS}$, ppm
0.89 [3H, t, —(CH$_2$)$_7$—CH$_3$]
1.06 (3H, d, J=6 Hz, C$^{6'}$—$^{CH}$$_3$)
2.92 (3H, br.s, N—CH$_3$)
5.33 (2H, t, —CH=CH—)
Elemental analysis for C$_{77}$H$_{108}$N$_6$O$_{18}$:

|  | C | H | N |
|---|---|---|---|
| Calculated (%): | 65.79 | 7.74 | 5.98 |
| Found (%): | 64.92 | 7.51 | 6.16 |

(b) The N-protected compound (13 mg) obtained in (a) was reacted and worked up in the same way as in Example 1, (b) to give 5.4 mg of the hydrochloride of the captioned compound as a colorless solid.

Specific rotation: $[\alpha]_D^{20}+66°$ (c=0.3, H$_2$O)
$^1$H-NMR value: $\delta_{D_2O}^{TMS}$, ppm
0.88 [3H, t, —(CH$_2$)$_{16}$—CH$_3$]
1.29 (s, stearoyl methylene portion)
1.34 (3H, d, J=6.5 Hz, C$^{6'}$—CH$_3$)
3.17 (3H, s, N—CH$_3$)
5.47 (1H, d, J=3.5 Hz, H-1')
Elemental analysis for C$_{45}$H$_{86}$N$_6$O$_{10}$·4HCl·2H$_2$O:

|  | C | H | N | Cl |
|---|---|---|---|---|
| Calculated (%): | 51.32 | 9.00 | 7.98 | 13.47 |
| Found (%): | 50.85 | 9.21 | 7.82 | 13.06 |

EXAMPLE 26

Production of 2''-N-[γ-O-(4-deoxycholyloxybutyl)-L-glutamyl]-5-de-O-methyl-KA-6606I:

(a) 570 mg of the free carboxylic acid obtained in the first half of Example 14, (b) and 524 mg of 4-(deoxycholyloxy)butanol were reacted and worked up in the same way as in the latter half of Example 10, (a). The reaction product was purified by silica gel column chromatography [solvent: chloroform/ethyl acetate/acetone (1:1:1)] and preparative thin-layer chromatography [carrier: silica gel; sovlent: chloroform/methanol (7:1)] to give 183 mg of 1,2',6'-tris-N-benzyloxycarbonyl-2'-N-[N-benzyloxycarbonyl-γ-O-(4-deoxycholyloxybutyl)-L-glutamyl]-5-de-O-methyl-KA-6606I as a colorless syrup.

Specific rotation: $[\alpha]_D^{22}+34°$ (c=1 CHCl$_3$)
$^1$H-NMR value: $\delta_{CDCl_3}^{TMS}$, ppm
0.65 (3H, s, deoxycholyl CH$_3$-18)
0.89 (3H, s, deoxycholyl CH$_3$-19)
0.99 (3H, d, J=6 Hz, deoxycholyl CH$_3$-21)
1.05 (3H, d, J=6 Hz, C$^{6'}$—CH$_3$)
2.93, 3.07 (total 3H, s, N—CH$_3$, rotational isomer)
Elemental analysis for C$_{81}$H$_{110}$N$_6$O$_{20}$:

|  | C | H | N |
|---|---|---|---|
| Calculated (%): | 65.39 | 7.45 | 5.65 |
| Found (%): | 65.11 | 7.82 | 5.30 |

(b) The N-protected compound (183 mg) obtained in (a) was reacted and worked up in the same way as in Example 1, (b) to give 115 mg of the hydrochloride of the captioned compound as a colorless solid.

Specific rotation: $[\alpha]_D^{20} +60°$ (c=0.5, H$_2$O)
$^1$H-NMR value: $\delta_{D_2O}^{TMS}$, ppm
0.70 (3H, s, deoxycholyl CH$_3$-18)
0.92 (3H, s, deoxycholyl CH$_3$-19)
0.99 (3H, br.s, deoxycholyl CH$_3$-21)
1.34 (3H, d, J=7 Hz, C$^{6'}$—CH$_3$)
3.16 (3H, s, N—CH$_3$)
5.47 (1H, d, J=3.5 Hz, H-1')
Elemental analysis for C$_{49}$H$_{86}$N$_6$O$_{12}$.4HCl.2H$_2$O:

|  | C | H | N | Cl |
|---|---|---|---|---|
| Calculated (%): | 51.94 | 8.36 | 7.42 | 12.51 |
| Found (%): | 52.47 | 8.43 | 7.54 | 13.04 |

EXAMPLE 27

Production of 2″-N-{γ-O-[4-(3,12-di-O-acetyldeoxycholyloxy)butyl]-L-glutamyl}-5-de-O-methyl-KA-6606I:

(a) 470 mg of 1,2',6'-tris-N-benzyloxycarbonyl-5-de-O-methyl-KA-6606I and 880 mg of an N-hydroxysuccinimide ester of N-benzyloxycarbonyl-γ-O-[4-(3,12-di-O-acetyldeoxycholyloxy)butyl]-L-glutamic acid were reacted and worked up in the same way as in Example 1, (a). The reaction product was purified first by silica gel column chromatography [solvent: chloroform/ethyl acetate/acetone (2:2:1)] and then by alumina column chromatography [solvent: chloroform/methanol (40:1)] to give 286 mg of 1,2',6'-tris-N-benzyloxycarbonyl-2″-N-{N-benzyloxycarbonyl-γ-O-[4-(3,12-di-O-acetyl-deoxycholyloxy)butyl]-L-glutamyl}-5-de-O-methyl-KA-6606I.

Specific rotation: $[\alpha]_D^{24} +50°$ (c=1, CHCl$_3$)
IR value: $\nu_{max}^{CHCl_3}$, cm$^{-1}$ 1710 (urethane, ester), 1635 (amide I), 1500 (amide II)
$^1$H-NMR value: $\gamma_{CDCl_3}^{TMS}$, ppm
0.71 (3H, s, deoxycholyl CH$_3$-18)
0.78 (3H, d, J=6 Hz, deoxycholyl CH$_3$-21)
0.90 (3H, s, deoxycholyl CH$_3$-19)
1.02 (3H, d, J=7 Hz, C$^{6'}$—CH$_3$)
2.03, 2.09 (each 3H, s, OCOCH$_3$)
~7.3 (20H, aromatic H)
Elemental analysis for C$_{85}$H$_{114}$N$_6$O$_{22}$:

|  | C | H | N |
|---|---|---|---|
| Calculated (%): | 64.95 | 7.31 | 5.35 |
| Found (%): | 65.12 | 7.32 | 5.23 |

(b) 62 mg of the N-protected compound obtained in (a) was reacted and worked up in the same way as in Example 1, (b) to give 40 mg of the hydrochloride of the captioned compound as a colourless solid.

Specific rotation: $[\alpha]_D^{26} +90°$ (c=1, H$_2$O)
IR value: $\nu_{max}^{KBr}$, cm$^{-1}$ 1710 (ester), 1610 (amide) I
$^1$H-NMR value: $\delta_{D_2O}^{TMS}$, ppm
1.36 (3H, d, J=7 Hz, C$^{6'}$—CH$_3$)
2.16, 2.04 (each 3H, s, OCOCH$_3$)
3.18 (3H, s, N—CH$_3$)
5.47 (1H, br.s, H-1')
Elemental analysis for C$_{53}$H$_{90}$N$_6$O$_{14}$.4HCl.2H$_2$O:

|  | C | H | N | Cl |
|---|---|---|---|---|
| Calculated (%): | 52.30 | 8.12 | 6.90 | 11.65 |
| Found (%): | 52.52 | 8.40 | 6.71 | 11.38 |

EXAMPLE 28

Production of 2″-N-[γ-O-(3-decanoylaminopropyl)-L-glutamyl]-5-de-O-methyl-KA-6606I:

(a) Fifty milligrams of the free carboxylic acid obtained in the first half of Example 14, (b) and 17 mg of 3-decanoylaminopropanol were reacted and worked up in the same way as in the latter half of Example 10, (a). The reaction product was purified by preparative thin-layer chromatography [carrier: silica gel; solvent: chloroform/ethyl acetate/acetone (4:4:3)] to give 16 mg of 1,2',6'-tris-N-benzyloxycarbonyl-2″-N-[N-benzyloxycarbonyl-γ-O-(3-decanoylaminopropyl)-L-glutamyl]-5-de-O-methyl-KA-6606I as a colorless solid.

Specific rotation: $[\alpha]_D^{20} +26°$ (c32 1, CHCl$_3$)
$^1$H-NMR value: $\delta_{CDCl_3}^{TMS}$, ppm
0.87 [3H, t, —(CH$_2$)$_8$-CH$_3$]
1.05 (3H, d, J=7 Hz, C$^{6'}$—CH$_3$)
1.24 (s, decanoyl methylene portion)
2.91 (3H, br.s, N—CH$_3$)
Elemental analysis for C$_{66}$H$_{89}$N$_7$O$_{17}$:

|  | C | H | N |
|---|---|---|---|
| Calculated (%): | 63.29 | 7.16 | 7.83 |
| Found (%): | 62.87 | 7.31 | 7.82 |

(b) The N-protected compound (16 mg) obtained in (a) was reacted and worked up in the same way as in Example 1, (b) to give 4 mg of the hydrochloride of the captioned compound as a colorless solid.

Specific rotation: $[\alpha]_D^{18} +47°$ (c=0.15, H$_2$O)
$^1$H-NMR value: $\delta_{D_2O}^{TMS}$, ppm
0.94 [3H, t, —(CH$_2$)$_8$—C$\underline{H}_3$]
1.28 (s, decanoyl methylene portion)
1.36 (3H, d, J=6.7 Hz, C$^{6'}$—CH$_3$)
3.16 (3H, s, N—CH$_3$)
5.48 (1H, d, J=3.5 Hz, H-1')
Elemental analysis for C$_{34}$H$_{65}$N$_7$O$_9$.4HCl.3H$_2$O:

|  | C | H | N | Cl |
|---|---|---|---|---|
| Calculated (%): | 44.59 | 8.25 | 10.71 | 15.49 |
| Found (%): | 43.92 | 8.14 | 10.61 | 15.48 |

EXAMPLE 29

Production of 2″-N-(Nγ-propyl-L-glutaminyl)-5-de-O-methyl-KA-6606I:

(a) 380 mg of 1,2',6'-tris-N-benzyloxycarbonyl-5-de-O-methyl-KA-6606I and 184 mg of an N-hydroxysuccinimide ester of N$^\alpha$-benzyloxycarbonyl-N$^\gamma$-propyl-L-glutamine were reacted and worked up in the same way as in Example 1, (a). The reaction product was purified by silica gel column chromatography [solvent: chloroform/methanol (97:3)] to give 236 mg of 1,2',6'-tris-N-benzyloxycarbonyl-2″-N-(N$^{\alpha\text{-}benzyloxycarbonyl\text{-}N\gamma}$-propyl- L-glutaminyl)-5-de-O-methyl-KA-6606I as a colorless solid.

Specific rotation: $[\alpha]_D^{24} +30°$ (c=3, CHCl$_3$)
IR value: $\nu_{max}^{CHCl_3}$, cm$^{-1}$ 1635 (amide I)
$^1$H-NMR value: $\delta_{CDCl_3}^{TMS}$, ppm
0.84 (3H, t, J=7.5Hz, —CH$_2$—CH$_2$—C$\underline{H}_3$)
1.04 (3H, br.d, J=6 Hz, C$^{6'}$—CH$_3$)
Elemental analysis for C$_{56}$H$_{71}$N$_7$O$_{15}$:

|  | C | H | N |
|---|---|---|---|
| Calculated (%): | 62.15 | 6.61 | 9.06 |
| Found (%): | 62.28 | 6.54 | 8.74 |

(b) The N-protected compound (236 mg) obtained in (a) was reacted and worked up in the same way as in Example 1, (b) to give 141 mg of the hydrochloride of the captioned compound as a colorless solid.

Specific rotation: $[\alpha]_D^{21} +83°$ (c=1.03, H$_2$O)
$^1$H-NMR value: $\delta_{D_2O}^{TMS}$, ppm
0.91 (3H, t, J=7.5 Hz, —CH$_2$—CH$_2$—C$\underline{H}_3$)
1.36 (3H, d, J=7 Hz, C$^{6'}$—CH$_3$)
3.19 (3H, s, N—CH$_3$)
5.49 (1H, d, J=3.5 Hz, H-1')
Elemental analysis for C$_{24}$H$_{47}$N$_7$O$_7$.4HCl.2H$_2$O:

|  | C | H | N | Cl |
|---|---|---|---|---|
| Calculated (%): | 39.62 | 7.62 | 13.48 | 19.49 |
| Found (%): | 40.01 | 7.84 | 13.18 | 19.63 |

EXAMPLE 30

Production of 2''-N-(N$^{\gamma\text{-}hexyl\text{-}L\text{-}glutaminyl}$)-5-de-O-methyl-KA-6606I:

(a) 437 mg of 1,2',6'-tris-N-benzyloxycarbonyl-5-de-O-methyl-KA-6606I and 247 mg of an N-hydroxysuccinimide ester of N$^{\alpha\text{-}benzyloxycarbonyl\text{-}N\gamma}$-hexyl-L-glutamine were reacted and worked up in the same way as in Example 1, (a). The reaction product was purified by silica gel column chromatography [solvent: chloroform/methanol (97:3)] to give 270 mg of 1,2',6'-tris-N-benzyloxycarbonyl-2''-N-(N$^{\alpha}$-benzyloxycarbonyl-N$^{\gamma\text{-}}$hexyl-L-glutaminyl)-5-de-O-methyl-KA-66066I as a colorless solid.

Specific rotation: $[\alpha]_D^{24} +30°$ (c=1, CHCl$_3$)
IR value: $\nu_{max}^{CHCl_3}$, cm$^{-1}$ 1638 (amide I)
$^1$H-NMR value: $\delta_{CDCl_3}^{TMS}$, ppm
0.86 [3H, t, —(CH$_2$)$_5$—C$\underline{H}_3$]
1.05 (3H, br.d, J=6 Hz, C$^{6'}$—CH$_3$)
Elemental analysis for C$_{59}$H$_{77}$N$_7$O$_{15}$:

|  | C | H | N |
|---|---|---|---|
| Calculated (%): | 63.03 | 6.90 | 8.72 |
| Found (%): | 63.18 | 7.13 | 8.48 |

(b) The N-protected compound (270 mg) obtained in (a) was reacted and worked up in the same way as in Example 1, (b) to give 166 mg of the hydrochloride of the captioned compound as a colorless solid.

Specific rotation: $[\alpha]_D^{24} +71°$ (c=1.21, H$_2$O)
$^1$H-NMR value: $\delta_{D_2O}^{TMS}$, ppm
0.88 [3H, t, —(CH$_2$)$_5$—C$\underline{H}_3$]
1.34 (3H, d, J=6.5 Hz, C$^{6'}$—CH$_3$)
3.17 (3H, s, N—CH$_3$)
5.48 (1H, d, J=3.5 Hz, H-1')

Elemental analysis for C$_{27}$H$_{53}$N$_7$O$_7$.4HCl.H$_2$O:

|  | C | H | N | Cl |
|---|---|---|---|---|
| Calculated (%): | 43.15 | 7.91 | 13.05 | 18.87 |
| Found (%): | 42.67 | 7.60 | 13.19 | 19.29 |

EXAMPLE 31

Production of 2''-N-(N$^{\gamma\text{-}octyl\text{-}L\text{-}glutaminyl}$)-5-de-O-methyl-KA-6606I:

(a) 452 mg of 1,2',6'-tris-N-benzyloxycarbonyl-5-de-O-methyl-KA-6606I and 258 mg of an N-hydroxysuccinimide ester of N$^{\alpha}$-benzyloxycarbonyl-N$^{\gamma\text{-}octyl\text{-}L\text{-}gluta}$-mine were reacted and worked up in the same way as in Example 1, (a). The reaction product was purified by silica gel column chromatography [solvent: chloroform/methanol (97:3)] to give 340 mg of 1,2',6'-tris-N-benzyloxycarbonyl-2''-N-(N$^{\alpha}$-benzyloxycarbonyl-N$^{\gamma}$-octyl-L-glutaminyl)-5-de-O-methyl-KA-6606I as a colorless solid.

Specific rotation: $[\alpha]_D^{23} +29°$ (c=5, CHCl$_3$)
IR value: $\nu_{max}^{CHCl_3}$, cm$^{-1}$ 1640 (shoulder, amide I)
$^1$H-NMR value: $\delta_{CDCl_3}^{TMS}$, ppm
0.86 [3H, t, —(CH$_2$)$_7$—CH$_3$]
1.04 (3H, br.d, J=6 Hz, C$^{6'}$—CH$_3$)
Elemental analysis for C$_{61}$H$_{81}$N$_7$O$_{15}$:

|  | C | H | N |
|---|---|---|---|
| Calculated (%): | 63.58 | 7.09 | 8.51 |
| Found (%): | 63.61 | 7.41 | 8.28 |

(b) The N-protected compound (340 mg) obtained in (a) was reacted and worked up in the same way as in Example 1, (b) to give 216 mg of the hydrochloride of the captioned compound as a colorless solid.

Specific rotation: $[\alpha]_D^{26} +72°$ (c=1.10, H$_2$O)
$^1$H-NMR value: $\delta_{D_2O}^{TMS}$, ppm
0.87 [3H, t, —(CH$_2$)$_7$—CH$_3$]
1.35 (3H, d, J=7 Hz, C$^{6'}$—CH$_3$)
3.18 (3H, s, N—CH$_3$)
5.49 (1H, d, J=3.5 Hz, H-1')
Elemental analysis for C$_{29}$H$_{57}$N$_7$O$_7$4HCl2H$_2$O:

|  | C | H | N | Cl |
|---|---|---|---|---|
| Calculated (%): | 43.67 | 8.21 | 12.29 | 17.78 |
| Found (%): | 44.10 | 8.50 | 12.02 | 18.14 |

EXAMPLE 32

Production of 2''-N-(N$^{\gamma}$-decyl-L-glutaminyl)-5-de-O-methyl-KA-6606I:

(a) 460 mg of 1,2',6'-tris-N-benzyloxycarbonyl-5-de-O-methyl-KA-6606I and 279 mg of an N-hydroxysuccinimide ester of N$^{\alpha}$-benzyloxycarbonyl-N$^{\gamma}$-decyl-L-glutamine were reacted and worked up in the same way as in Example 1, (a). The reaction product was purified by silica gel column chromatography [solvent: chloroform/methanol (97:3)] to give 304 mg of 1,2', 6'-tris-N-benzyloxycarbon-yl-2''-N-(N$^{\alpha\text{-}benzyloxycarbonyl\text{-}N\gamma\text{-}decyl\text{-}L\text{-}}$ glutaminyl)-5-de-O-methyl-KA-6606I as a colorless solid.

Specific rotation: $[\alpha]_D^{26} +27°$ (c=2, CHCl$_2$)
$^1$H-NMR value: $\delta_{CDCl_3}^{TMS}$, ppm
0.87 [3H, t, —(CH$_2$)$_9$—C$\underline{H}_3$]
1.04 (3H, d, J=6 Hz, C$^{6'}$—CH$_3$)
Elemental analysis for C$_{63}$H$_{85}$N$_7$O$_{15}$:

| | C | H | N |
|---|---|---|---|
| Calculated (%): | 64.10 | 7.26 | 8.31 |
| Found (%): | 63.71 | 7.48 | 8.04 |

(b) The N-protected compound (304 mg) obtained in (a) was reacted and worked up in the same way as in Example 1, (b) to give 187 mg of the hydrochloride of the captioned compound as a colorless solid.

Specific rotation: $[\alpha]_D^{24} +71°$ (c=1.04, H$_2$O)
$^1$H-NMR value: $\delta_{D_2O}^{TMS}$, ppm
0.89 [3H, t, —(CH$_2$)$_9$—CH$_3$]
1.36 (3H, d, J=7 Hz, C$^{6'}$—CH$_3$)
3.19 (3H, s, N—CH$_3$)
5.49 (1H, d, J=3.5 Hz, H-1')
Elemental analysis for C$_{31}$H$_{61}$N$_7$O$_7$·4HCl·2H$_2$O:

| | C | H | N | Cl |
|---|---|---|---|---|
| Calculated (%): | 45.09 | 8.42 | 11.87 | 17.17 |
| Found (%): | 44.61 | 8.87 | 11.52 | 17.42 |

EXAMPLE 33

Production of 2"-N-[Nγ-(1-naphthyl)-L-glutamin-yl]-de-O-methyl-KA-6606I:

(a) 479 mg of 1,2',6'-tris-N-benzyloxycarbonyl-5-de-O-methyl-KA-6606I and 322 mg of an N-hydroxysuccinimide ester of N$^\alpha$-benzyloxycarbonyl-Nγ-(1-naphthyl)-L-glutamine were reacted and worked up in the same way as in Example 1, (a). The reaction product was purified by silica gel column chromatography [solvent: chloroform/methanol (97:3)] to give 274 mg of 1,2',6'-tris-N-benzyloxycarbonyl-2"-N-[N$^{\alpha\text{-}benzyloxycarbonyl}$-Nγ-(1-naphthyl)-L-glutaminyl]-5-de-O-methyl-KA-6606I as a colorless solid.

Specific rotation: $[\alpha]_D^{24} +30°$ (c=2, CHCl$_3$)
IR value: $\nu_{max}^{CHCl_3}$, cm$^{-1}$ 1635 (amide I)
$^1$H-NMR value: $\delta_{CDCl_3}^{TMS}$, ppm
0.97 (3H, br.s, C$^{6'}$—CH$_3$)
2.80, 2.97 (total 3H, s, N—CH$_3$, rotational isomer)
Elemental analysis for C$_{63}$H$_{71}$N$_7$O$_{15}$:

| | C | H | N |
|---|---|---|---|
| Calculated (%): | 64.88 | 6.14 | 8.41 |
| Found (%): | 65.09 | 6.34 | 8.13 |

(b) The N-protected compound (274 mg) obtained in (a) was reacted and worked up in the same way as in Example 1, (b) to give 167 mg of the hydrochloride of the captioned compound as a colorless solid.

Specific rotation: $[\alpha]_D^{24} +66°$ (c=1.22, H$_2$O)
$^1$H-NMR value: $\delta_{D_2O}^{TMS}$, ppm
1.28 (3H, d, J=7 Hz, C$^{6'}$—CH$_3$)
3.14 (3H, s, N—CH$_3$)
5.36 (1H, d, J=3.5 Hz, H-1')
7.6–8.1 (7H, naphthyl H)
Elemental analysis for C$_{31}$H$_{47}$N$_7$O$_7$·4HCl·2H$_2$O:

| | C | H | N | Cl |
|---|---|---|---|---|
| Calculated (%): | 45.88 | 6.83 | 12.08 | 17.47 |
| Found (%): | 46.41 | 6.50 | 11.94 | 17.68 |

EXAMPLE 34

Production of 2"-N-[Nγ-(3-acetylaminopropyl)-L-glutaminyl]-5-de-O-methyl-KA-6606I:

(a) 315 mg of 1,2',6'-tris-N-benzyloxycarbonyl-5-de-O-methyl-KA-6606I and 300 mg of an N-hydroxysuccinimide ester of Nγ-(3-acetylaminopropyl)-N$^\alpha$-benzyloxycarbonyl-L-glutamine were reacted and worked up in the same way as in Example 1, (a). The reaction product was purified by silica gel column chromatography [solvent: chloroform/methanol (30:1→10:1)] to give 303 mg of 1,2',6'-tris-N-benzyloxycarbonyl-2"-N-[Nγ-(3-acetylaminopropyl)-N$^\alpha$-benzyloxycarbonyl-L-glutaminyl]-5-de-O-methyl-KA-6606I as a colorless solid.

Specific rotation: $[\alpha]_D^{21} +30°$ (c=1, CHCl$_3$)
IR value: $\nu_{max}^{CHCl_3}$, cm$^{-1}$ 1710 (urethane), 1655 (amide I), 1510 (amide II)
$^1$H-NMR value: $\delta_{CDCl_3}^{TMS}$, ppm
1.03 (3H, d, J=7 Hz, C$^{6'}$—CH$_3$)
1.89 (3H, s, COCH$_3$)
~7.3 (20H, aromatic H)
Elemental analysis for C$_{58}$H$_{74}$N$_8$O$_{16}$:

| | C | H | N |
|---|---|---|---|
| Calculated (%): | 61.15 | 6.55 | 9.84 |
| Found (%): | 61.27 | 6.74 | 9.76 |

(b) 254 mg of the N-protected compound obtained in (a) was reacted and worked up in the same way as in Example 1, (b) to give 163 mg of the hydrochloride of the captioned compound as a colorless solid.

Specific rotation: $[\alpha]_D^{21} +74°$ (c=1, H$_2$O)
IR value: $\nu_{max}^{KBr}$, cm$^{-1}$ 1625 (amide I)
$^1$H-NMR value: $\delta_{D_2O}^{TMS}$, ppm
1.36 (3H, d, J=7 Hz, C$^{6'}$—CH$_3$)
2.01 (3H, s, COCH$_3$)
3.18 (3H, s, N—CH$_3$)
5.50 (1H, d, J=3.5 Hz, H-1')
Elemental analysis for C$_{26}$H$_{50}$N$_8$O$_8$·4HCl·2H$_2$O:

| | C | H | N | Cl |
|---|---|---|---|---|
| Calculated (%): | 39.80 | 7.45 | 14.28 | 18.07 |
| Found (%): | 39.90 | 7.57 | 14.22 | 17.95 |

EXAMPLE 35

Production of 2"-N-[Nγ-(3-n-butyrylaminopropyl)-L-glutaminyl]-5de-O-methyl-KA-6606I:

(a) 315 mg of 1,2',6'-tris-N-benzyloxycarbonyl-5-de-O-methyl-KA-6606I and 350 mg of an N-hydroxysuccinimide ester of N$^\alpha$-benzyloxycarbonyl-Nγ-(3-n-butyrylaminopropyl)-L-glutamine were reacted and worked up in the same way as in Example 1, (a). The reaction product was purified by silica gel column chromatography [solvent: chloroform/methanol (20:1)] to give 297 mg of 1,2',6'-tris-N-benzyloxycarbonyl-2"-N-[N$^\alpha$-benzyloxycarbonyl-Nγ-(3-n-butyrylaminopropyl)-L-glutaminyl]-5-de-O-methyl-KA-6606I as a colorless solid.

Specific rotation: $[\alpha]_D^{21} +32°$ (c=1, CHCl$_3$)
IR value: $\nu_{max}^{CHCl_3}$, cm$^{-1}$ 1705 (urethane), 1635 (amide I), 1510 (amide II)
$^1$H-NMR value: $\delta_{CDCl_3}^{TMS}$, ppm
0.88 [3H, t, J=6.5 Hz, —(CH$_2$)$_2$—CH$_3$]
1.02 (3H, d, J=7 Hz, C$^{6'}$—CH$_3$)

~7.3 (20H, aromatic H)
Elemental analysis for $C_{60}H_{78}N_8O_{16}$:

|  | C | H | N |
|---|---|---|---|
| Calculated (%): | 61.74 | 6.74 | 9.60 |
| Found (%): | 61.99 | 6.87 | 9.55 |

(b) The N-protected compound (297 mg) obtained in (a) above was reacted and worked up in the same ways in Example 1, (b) to give 189 mg of the hydrochloride of the captioned compound as a colorless solid.

Specific rotation: $[\alpha]_D^{21}$ +72° (c=1, $H_2O$)
IR value: $\nu_{max}^{KBr}$, cm$^{-1}$ 1625 (amide I)
$^1$H-NMR value: $\delta_{D_2O}^{TMS}$, ppm
0.92 [3H, t, J=6.5 Hz, —(CH$_2$)$_2$—CH$_3$]
1.36 (3H, d, J=7 Hz, C$^{6'}$—CH$_3$)
3.19 (3H, s, N—CH$_3$)
5.50 (1H, d, J=3.5 Hz,, H-1')
Elemental analysis for $C_{28}H_{54}N_8O_8 \cdot 4HCl \cdot 3/2H_2O$:

|  | C | H | N | Cl |
|---|---|---|---|---|
| Calculated (%): | 41.85 | 7.65 | 13.94 | 17.65 |
| Found (%): | 41.92 | 7.57 | 13.68 | 17.52 |

EXAMPLE 36

Production of 2''-N-[N$^\gamma$-(3-hexanoylaminopropyl)-L-glutaminyl]-5-de-O-methyl-KA-6606I:

315 mg of 1,2',6'-tris-N-benzyloxycarbonyl-5-de-O-methyl-KA-6606I and 360 mg of an N-hydroxysuccinimide ester of N$^\alpha$-benzyloxycarbonyl-N$^\gamma$-(3-hexanoylaminopropyl)-L-glutamine were reacted and worked up in the same way as in Example 1, (a). The reaction product was purified by silica gel column chromatography [sovlent: chloroform/methanol (20:1)] to give 278 mg of 1,2',6'-tris-N-benzyloxycarbonyl-2''-N-[N$^\alpha$-benzyloxycarbonyl-N$^\gamma$-(3-hexanoylaminopropyl-L-glutaminyl]-5-de-O-methyl-KA-6606I as a colorless solid.

Specific rotation: $[\alpha]_D^{21}$ +31° (c=1, CHCl$_3$)
IR value: $\nu_{max}^{CHCl_3}$, cm$^{-1}$ 1710 (urethane), 1640 (amide I), 1510 (amide II)
$^1$H-NMR value: $\delta_{CDCl_3}^{TMS}$, ppm
0.86 [3H, t, —(CH$_2$)$_4$—CH$_3$]
1.03 (3H, d, J=7 Hz, C$^{6'}$—CH$_3$)
~7.3 (20H, aromatic H)
Elemental analysis for $C_{62}H_{82}N_8O_{16}$:

|  | C | H | N |
|---|---|---|---|
| Calculated (%): | 62.30 | 6.91 | 9.37 |
| Found (%): | 62.55 | 7.03 | 9.11 |

(b) 272 mg of the N-protected compound obtained in (a) was reacted and worked up in the same way as in Example 1, (b) to give 177 mg of the hydrochloride of the captioned compound as a colorless solid.

Specific rotation: $[\alpha]_D^{21}$ +69° (c=1, $H_2O$)
IR value: $\nu_{max}^{KBr}$, cm$^{-1}$ 1625 (amide I)
$^1$H-NMR value: $\delta_{D_2O}^{TMS}$, ppm
0.88 [3H, t, —(CH$_2$)$_4$—CH$_3$]
1.35 (3H, d, J=7 Hz, C$^{6'}$—CH$_3$)
3.13 (3H, s, N—CH$_3$)
5.44 (1H, d, J=3.5 Hz, H-1')
Elemental analysis for $C_{30}H_{58}N_8O_8 \cdot 4HCl \cdot 2H_2O$:

|  | C | H | N | Cl |
|---|---|---|---|---|
| Calculated (%): | 42.86 | 7.91 | 13.33 | 16.87 |
| Found (%): | 42.73 | 7.76 | 13.09 | 16.60 |

EXAMPLE 37

Production of 2''-N-[N$^\gamma$-(3-octanoylaminopropyl)-L-glutaminyl]-5-do-O-methyl-KA-6606I:

(a) 313 mg of 1,2',6'-tris-N-benzyloxycarbonyl-5-de-O-methyl-KA-6606I and 210 mg of an N-hydroxysuccinimide ester of N$^\alpha$-benzyloxycarbonyl-N$^\gamma$-(3-octanoylaminopropyl)-L-glutamine were reacted and worked up in the same way as in Example 1 (a). The reaction product was purified by silica gel column chromatography [solvent: chloroform/ethyl acetate/acetone (1:1:2)] to give 118 mg of 1,2',6'-tris-N-benzyloxycarbonyl-2''-N-[N$^\alpha$-benzyloxycarbonyl-N$^\gamma$-(3-octanoylaminopropyl)-L-glutaminyl]-5-de-O-methyl-KA-6606I as a colorless solid.

Specific rotation: $[\alpha]_D^{24}$ +28° (c=2, CHCl$_3$)
$^1$H-NMR value: $\delta_{CDCl_3}^{TMS}$, ppm
0.87 [3H, t, —(CH$_2$)$_6$—CH$_3$]
1.07 (3H, br.s, C$^{6'}$—CH$_3$)
2.92 (3H, br.s, N—CH$_3$)
Elemental analysis for $C_{64}H_{86}N_8O_{16}$:

|  | C | H | N |
|---|---|---|---|
| Calculated (%): | 62.83 | 7.09 | 9.16 |
| Found (%): | 62.68 | 6.66 | 8.71 |

(b) 116 mg of the N-protected compound obtained in (a) was reacted and worked up in the same way as in Example 1, (b) to give 70 mg of the hydrochloride captioned compound as a colorless solid.

Specific rotation: $[\alpha]_D^{24}$ +76° (c=1, $H_2O$)
$^1$H-NMR value: $\delta_{D_2O}^{TMS}$, ppm
0.87 [3H, t, —(CH$_2$)$_6$—CH$_3$]
1.29 (3H, s, octanoyl methylene portion)
1.35 (3H, d, J=6.8 Hz, C$^{6'}$—CH$_3$)
3.18 (3H, s, N—CH$_3$)
5.49 (1H, d, J=3.5 Hz, H-1')
Elemental analysis for $C_{32}H_{62}N_8O_8 \cdot 4HCl \cdot 2H_2O$:

|  | C | H | N | Cl |
|---|---|---|---|---|
| Calculated (%): | 44.24 | 8.12 | 12.90 | 16.32 |
| Found (%): | 44.45 | 8.03 | 12.48 | 16.11 |

EXAMPLE 38

Production of 2''-N-[N$^\gamma$-(3-decanoylaminopropyl)-L-glutaminyl]-5-de-O-methyl-KA-6606I:

263 mg of 1,2',6'-tris-N-benzyloxycarbonyl-5-de-O-methyl-KA-6606I and 181 mg of an N-hydroxysuccinimide ester of N$^\alpha$-benzyloxycarbonyl-N$^\gamma$-(3-decanoylaminopropyl)-L-glutamine were reacted and worked up in the same way as in Example 1, (a). The reaction product was purified by silica gel column chromatography [solvent: chloroform/methanol (95:5)] to give 188 mg of 1,2',6'-tris-N-benzyloxycarbonyl-2''-N-[N$^\alpha$-benzyloxycarbonyl-N$^\gamma$-(3-decanoylaminopropyl)-L-glutaminyl]-5-de-O-methyl-KA-6606I as a colorless solid.

Specific rotation: $[\alpha]_D^{25}$ +26° (c=1.5, CHCl$_3$)
IR value: $\nu_{max}^{CHCl_3}$, cm$^{-1}$ 1635 (amide I)

$^1$H-NMR value: $\delta_{CDCl_3}^{TMS}$, ppm
~0.87 [3H, t, —(CH$_2$)$_8$—CH$_3$]
1.04 (3H, br.d, C$^{6'}$—CH$_3$)
Elemental analysis for C$_{66}$H$_{90}$N$_8$O$_{16}$:

|  | C | H | N |
|---|---|---|---|
| Calculated (%): | 63.34 | 7.25 | 8.95 |
| Found (%): | 63.54 | 7.04 | 8.67 |

(b) The N-protected compound (188 mg) obtained in (a) was reacted and worke up in the same way as in Example 1, (b) to give 127 mg of the hydrochloride of the captioned compound as colorless solid.

Specific rotation: $[\alpha]_D^{26}$ +60° (c=1, H$_2$O)
$^1$H-NMR value: $\delta_{D_2O}^{TMS}$, ppm
0.87 [3H, t, —(CH$_2$)$_8$—CH$_3$]
1.36 (3H, d, J=7 Hz, C$^{6'}$—CH$_3$)
3.19 (3H, s, N—CH$_3$)
5.49 (1H, d, J=3.5 Hz, H-1')
Elemental analysis for C$_{34}$H$_{66}$N$_8$O$_8$·4HCl·2H$_2$O:

|  | C | H | N | Cl |
|---|---|---|---|---|
| Calculated (%): | 45.54 | 8.32 | 12.50 | 15.81 |
| Found (%): | 45.11 | 8.40 | 12.31 | 16.33 |

EXAMPLE 39

Production of 2"-N-[N$^\gamma$-(3-lauroylaminopropyl)-L-glutaminyl]-5-de-O-methyl-KA-6606I:

(a) 313 mg of 1,2',6'-tris-N-benzyloxycarbonyl-5-de-O-methyl-KA-6606I and 290 mg of an N-hydroxylsuccinimide ester of N$^\alpha$-benzyloxycarbonyl-N$^\gamma$-(3-lauroylaminopropyl)-L-glutamine were reacted and worked up in the same way as in Example 1, (a). The reaction product was purified by silica gel column chromatography [solvent: chloroform/methanol (20:1)] to give 228 mg of 1,2',6'-tris-N-benzyloxycarbonyl-2"-N-[N$^\alpha$-benzyloxycarbonyl-N$^\gamma$-(3-lauroylaminopropyl)-L-glutaminyl]-5-de-O-methyl-KA-6606I as a colorless solid.

Specific rotation: $[\alpha]_D^{24}$ +27° (c=1, CHCl$_3$)
$^1$H-NMR value: $\delta_{CDCl_3}^{TMS}$, ppm
0.88 [3H, t, —(CH$_2$)$_{10}$—CH$_3$]
1.06 (3H, d, J=6 Hz, C$^{6'}$—CH$_3$)
2.93 (3H, s, N—CH$_3$)
Elemental analysis for C$_{68}$H$_{94}$N$_8$O$_{16}$:

|  | C | H | N |
|---|---|---|---|
| Calculated (%): | 63.83 | 7.41 | 8.76 |
| Found (%): | 63.18 | 7.16 | 8.53 |

(b) The N-protected compound (228 mg) obtained in (a) was reacted and worked up in the same way as in Example 1, (b) to give 140 mg of the hydrochloride of the captioned compound as a colorless solid.

Specific rotation: $[\alpha]_D^{24}$ +74° (c=5, H$_2$O)
$^1$H-NMR value: $\delta_{D_2O}^{TMS}$, ppm
0.88 [3H, t, —(CH$_2$)$_{10}$—CH$_3$]
1.30 (s, lauroyl methylene portion)
1.35 (3H, d, J=7 Hz, C$^{6'}$—CH$_3$)
3.19 (3H, s, N—CH$_3$)
5.48 (1H, br.s., H-1')
Elemental analysis for C$_{36}$H$_{70}$N$_8$O$_8$·4HCl·3/2H$_2$O:

|  | C | H | N | Cl |
|---|---|---|---|---|
| Calculated (%): | 47.21 | 8.47 | 12.24 | 15.48 |
| Found (%): | 46.56 | 8.51 | 11.99 | 15.53 |

EXAMPLE 40

Production of 2"-N-[N$^\gamma$-(3-stearoylaminopropyl)-L-glutaminyl]-5-de-O-methyl-KA-6606I:

(a) 315 mg of 1,2',6'-tris-N-benzoyloxycarbonyl-5-de-O-methyl-KA-6606I and 370 mg of an N-hydroxysuccinimide ester of N$^\alpha$-benzyloxycarbonyl-N$^\gamma$-(3-stearoylaminpropyl)-L-glutamine were reacted and worked up in the same way as in Example 1, (a). The reaction product was purified by silica gel column chromatography [solvent: chloroform/ethyl acetate/acetone (2:2:3→1:1:2)→chloroformmethanol (10:1)] to give 346 mg of 1,2',6'-tris-N-benzyloxycarbonyl-2"-N-[N$^\alpha$-benzyloxycrbonyl-N$^\gamma$-(3-stearoylaminopropyl)-L-glutaminyl]-5-de-O-methyl-KA-6606I as a colorless solid.

Specific rotation: $[\alpha]_D^{23}$ +25° (c=1, CHCl$_3$)
$^1$H-NMR value: $\delta_{CDCl_3}^{TMS}$, ppm
0.88 [3H, t, —(CH$_2$)$_{16}$—CH$_3$]
1.04 (3H, d, J=7 Hz, C$^{6'}$—CH$_3$)
~1.26 (br.s, stearoyl methylene portion)
~7.3 (20H, aromatic H)
Elemental analysis for C$_{74}$H$_{106}$N$_8$O$_{16}$:

|  | C | H | N |
|---|---|---|---|
| Calculated (%): | 65.18 | 7.84 | 8.22 |
| Found (%): | 65.22 | 7.95 | 8.13 |

(b) 326 mg of the N-protected compound obtained in (a) was reacted and worked up in the same way as in Example 1, (b) to give 203 mg of the hydrochloride of the captioned compound as a colorless solid.

Specific rotation: $[\alpha]_D^{22}$ +51° (c=1, H$_2$O)
IR value: $\nu_{max}^{KBr}$, cm$^{-1}$ 1630 (amide I)
$^1$H-NMR value: $\delta_{D_2O}^{TMS}$, ppm
0.88 [3H, t, —(CH$_2$)$_{16}$—CH$_3$]1.28 (br.s, stearoyl methylene portion)
1.36 (3H, d, J=7 Hz, C$^{6'}$—CH$_3$)
3.18 (3H, s, N—CH$_3$)
5.50 (1H, d, J=3.5 Hz, H-1')
Elemental analysis for C$_{42}$H$_{82}$N$_8$O$_8$·4HCl·H$_2$O:

|  | C | H | N | Cl |
|---|---|---|---|---|
| Calculated (%): | 50.90 | 8.95 | 11.31 | 14.31 |
| Found (%): | 51.28 | 9.13 | 11.15 | 14.56 |

EXAMPLE 41

Production of 2"-N-[N$^\gamma$-(3-lignocerolylaminopropyl)-L-glutaminyl]-5-de-O-methyl-KA-6606I:

(a) 315 mg of 1,2',6'-tris-N-benzyloxycarbonyl-5-de-O-methyl-KA-6606I and 480 mg of an N-hydroxysuccinimide ester of N$^\alpha$-benzyloxycarbonyl-N$^\gamma$-(3-lignocerolylaminopropyl)-L-glutamine were reacted and worked up in the same way as in Example 1, (a). The reaction product was purified by silica gel column chromatography [solvent: chloroform/ethyl acetate/acetone (1:1:2)] to give 306 mg of 1,2',6'-tris-N-benzyloxycarbonyl 2"-N-[N$^\alpha$-benzyloxycarbonyl-N$^\gamma$-(3-lignoceroylaminopropyl)-L-glutaminyl]-5-de-O-methyl-KA-6606I as a colorless solid.

Specific rotation: $[\alpha]_D^{22}$ +25° (c=1, CHCl$_3$)
$^1$H-NMR value: $\delta_{CDCl_3}^{TMS}$, ppm
0.88 [3H, t, —(CH$_2$)$_{22}$—C$\underline{H}_3$]
1.04 (3H, d, J=7 Hz, C$^{6'}$—CH$_3$)
1.27 (br.s, lignoceroyl methylene portion)
~7.3 (20H, aromatic H)
Elemental analysis for C$_{80}$H$_{118}$N$_8$O$_{16}$:

|  | C | H | N |
|---|---|---|---|
| Calculated (%): | 66.36 | 8.22 | 7.74 |
| Found (%): | 66.63 | 8.47 | 7.48 |

(b) 300 mg of the N-protected compound obtained in (a) was reacted and worked up in the same way as in Example 1, (a) to give 198 mg of the hydrochloride of the captioned compound as a colorless solid.

Specific rotation: $[\alpha]_D^{23}$ +49° (c=1, H$_2$O)
IR value: $\nu_{max}^{KBr}$, cm$^{-1}$ 1625 (amide I)
$^1$H-NMR value: $\delta_{D_2O}^{TMS}$, ppm
0.88 [3H, t, —(CH$_2$)$_{22}$—C$\underline{H}_3$]
1.36 (3H, d, J=7 Hz, C$^{6'}$—CH$_3$)
3.18 (3H, s, N—CH$_3$)
5.50 (1H, br.s, H-1')
Elemental analysis for C$_{48}$H$_{94}$N$_8$O$_8$·4HCl·2H$_2$O:

|  | C | H | N | Cl |
|---|---|---|---|---|
| Calculated (%): | 52.74 | 9.40 | 10.25 | 12.97 |
| Found (%): | 52.94 | 9.63 | 10.02 | 12.70 |

EXAMPLE 42

Production of 2''-N-[N$\gamma$-(8-hydroxyoctyl)-L-glutaminyl]-5-de-O-methyl-KA-6606I:

315 mg of 1,2',6'-tris-N-benzyloxycarbonyl-5-de-O-methyl-KA-6606I and 350 mg of an N-hydroxysuccinimide ester of N$^\alpha$-benzyloxycarbonyl-N$\gamma$-(8-hydroxyoctyl)-L-glutamine were reacted and worked up in the same way as in Example 1, (a). The reaction product was purified by silica gel column chromatography [solvent: chloroform/methanol (30:1→20:1)] to give 298 mg of 1,2',6'-tris-N-benzyloxycarbonyl-2''-N-[N$^\alpha$-benzyloxycarbonyl-N$\gamma$-8-hydroxyoctyl)-L-glutaminyl]-5-de-O-methyl-KA-6606I as a colorless solid.

Specific rotation: $[\alpha]_D^{21}$ +31° (c=1, CHCl$_3$)
IR value: $\nu_{max}^{CHCl_3}$, cm$^{-1}$ 1710 (urethane), 1635 (amide I), 1505 (amide II)
$^1$H-NMR value: $\delta_{CDCl_3}^{TMS}$, ppm
1.03 (3H, t, J=7 Hz, C$^{6'}$—CH$_3$)
1.25 [12H, br.s, —CH$_2$—(C$\underline{H}_2$)$_6$—CH$_2$—]
3.56 (2H, t, J=6.5 Hz, —C$\underline{H}_2$—OH)
~7.3 (20H, aromatic H)
Elemental analysis for C$_{61}$H$_{81}$N$_7$O$_{16}$:

|  | C | H | N |
|---|---|---|---|
| Calculated (%): | 62.71 | 6.99 | 8.39 |
| Found (%): | 62.89 | 7.13 | 8.18 |

(b) 263 mg of the N-protected compound obtained in (a) was reacted and worked up in the same way as in Example 1, (b) to give 166 mg of the hydrochloride of the captioned compound as a colorless solid.

Specific rotation: $[\alpha]_D^{22}$ +78° (c=1, H$_2$O)
IR value: $\nu_{max}^{KBr}$, cm$^{-1}$ 1620 (amide I)
$^1$H-NMR value: $\delta_{D_2O}^{TMS}$, ppm
1.33 [12H, br.s, —CH$_2$—(C$\underline{H}_2$)$_6$—CH$_2$—]
1.35 (3H, d, J=7 Hz, C$^{6'}$—CH$_3$)
3.18 (3H, s, N—CH$_3$)
3.61 (2H, t, J=6.5 Hz, —C$\underline{H}_2$—OH)
5.50 (1H, d, J=3.5 Hz, H-1')
Elemental analysis for C$_{29}$H$_{57}$N$_7$O$_8$·4HCl·2H$_2$O:

|  | C | H | N | Cl |
|---|---|---|---|---|
| Calculated (%): | 42.81 | 8.05 | 12.05 | 17.43 |
| Found (%): | 43.06 | 7.79 | 12.31 | 17.60 |

EXAMPLE 43

Production of 2''-N-[N$\gamma$-(3-isopropoxypropyl)-L-glutaminyl]-5-de-O-methyl-KA-6606I:

295 mg of 1,2',6'-tris-N-benzyloxycarbonyl-5-de-O-methyl-KA-6606I and 181 mg of an N-hydroxysuccinimide ester of N$^\alpha$-benzyloxycarbonyl-N$\gamma$-(3-isopropoxypropyl)-L-glutamine were reacted and worked up in the same way as in Example 1, (a). The reaction product was purified by silica gel column chromatography [solvent: chloroform/methanol (97:3)] to give 204 mg of 1,2',6'-tris-N-benzyloxycarbonyl-2''-N-[N$^\alpha$-benzyloxycarbonyl-N$\gamma$-(3-isopropoxypropyl)-L-glutaminyl]-5-de-O-methyl-KA-6606I as a colorless solid.

Specific rotation: $[\alpha]_D^{18}$ +26° (c=3, CHCl$_3$)
IR value: $\nu_{max}^{CHCl_3}$, cm$^{-1}$ 1635 (amide I)
$^1$H-NMR value: $\delta_{CDCl_3}^{TMS}$, ppm
1.11 [6H, d, J=6 Hz, —CH(C$\underline{H}_3$)$_2$]
2.89, 3.04 (total 3H, s, N—CH$_3$, rotational isomer)
Elemental analysis for C$_{59}$H$_{77}$N$_7$O$_{16}$:

|  | C | H | N |
|---|---|---|---|
| Calculated (%): | 62.14 | 6.81 | 8.60 |
| Found (%): | 62.33 | 7.87 | 8.38 |

(b) The N-protected compound (204 mg) obtained in (a) was reacted and worked up in the same way as in Example 1, (b) to give 133 mg of the hydrochloride of the captioned compound as a colorless solid.

Specific rotation: $[\alpha]_D^{20}$ +77° (c=1.02, H$_2$O)
$^1$H-NMR value: $\delta_{D_2O}^{TMS}$, ppm
1.18 [6H, d, J=6 Hz, —CH(C$\underline{H}_2$)$_3$]
1.36 (3H, d, J=6.5 Hz, C$^{6'}$—CH$_3$)
3.19 (3H, s, N—CH$_3$)
5.50 (1H, d, J=3.5 Hz, H-1')
Elemental analysis for C$_{27}$H$_{53}$N$_7$O$_8$·4HCl·2H$_2$O:

|  | C | H | N | Cl |
|---|---|---|---|---|
| Calculated (%): | 41.28 | 7.83 | 12.48 | 18.05 |
| Found (%): | 41.74 | 8.07 | 11.99 | 18.51 |

EXAMPLE 44

Production of 2''-N-[N$\gamma$-(hexylaminocarbonylmethyl)-L-glutaminyl]-5-de-O-methyl-KA-6606I:

(a) 315 mg of 1,2',6'-tris-N-benzyloxycarbonyl-5-de-O-methyl-KA-6606I and 380 mg of an N-hydroxysuccinimide ester of N$^\alpha$-benzyloxycarbonyl-N$\gamma$-(hexylaminocarbonylmethyl)-L-glutamine were reacted and worked up in the same way as in Example 1, (a). The product was purified by silica gel column chromatography [solvent: chloroform/methanol (30:1→20:1)] to give 352 mg of 1,2',6'-tris-N-benzyloxycarbonyl-2''-N-

[Nα-benzyloxycarbonyl-Nγ-(hexylaminocarbonylmethyl)-L-glutaminyl]-5-de-O-methyl-KA-6606I as a colorless solid.

Specific rotation: $[\alpha]_D^{19}$ +40° (c=1, CH$_3$OH)
IR value: $\nu_{max}^{KBr}$, cm$^{-1}$ 1700 (urethane), 1640 (amide II)
$^1$H-NMR value: $\delta_{CDCl_3-CD_3OD}^{TMS}$, ppm
0.86 [3H, t, —(CH$_2$)$_5$—CH$_3$]
1.04 (3H, d, J=7 Hz, C$^{6'}$—CH$_3$)
~7.3 (20H, m, aromatic H)
Elemental analysis for C$_{61}$H$_{80}$N$_8$O$_{16}$:

|  | C | H | N |
|---|---|---|---|
| Calculated (%): | 62.02 | 6.83 | 9.49 |
| Found (%): | 62.24 | 7.02 | 9.56 |

(b) The N-protected compound (352 mg) obtained in (a) was reacted and worked up in the same way as in Example 1, (b) to give 233 mg of the hydrochloride of the captioned compound as a colorless solid.

Specific rotation: $[\alpha]_D^{19}$ +70° (c=1, H$_2$O)
IR value: $\nu_{max}^{KBr}$, cm$^{-1}$ 1630 (amide I)
$^1$H-NMR value: $\delta_{D_2O}^{TMS}$, ppm
0.88 [3H, t, —(CH$_2$)$_5$—CH$_3$]
1.30 (br.s, hexyl methylene portion)
1.36 (3H, d, J=6.5 Hz, C$^{6'}$—CH$_3$)
3.19 (3H, s, N—CH$_3$)
3.90 (2H, s, —CH$_2$—CONHC$_6$H$_{13}$)
5.50 (1H, d, J=3.5 Hz, H-1')
Elemental analysis for C$_{29}$H$_{56}$N$_8$O$_8$.4HCl.2H$_2$O:

|  | C | H | N | Cl |
|---|---|---|---|---|
| Calculated (%): | 42.13 | 7.80 | 13.55 | 17.15 |
| Found (%): | 42.35 | 8.09 | 13.22 | 16.87 |

EXAMPLE 45

Production of 2''-N-{Nγ-[3-(3,12-di-O-acetyldeoxycholylamino)propyl]-L-glutaminyl}-5-de-O-methyl-KA-6606I:

(a) 590 mg of 1,2',6'-tris-N-benzyloxycarbonyl-5-de-O-methyl-KA-6606I and 727 mg of an N-hydroxysuccinimide ester of Nα-benzyloxycarbonyl-Nγ-[3-(3,12-di-O-acetyldeoxycholylamino)propyl]-L-glutamine were reacted and worked up in the same way as in Example 1, (a). The reaction product was purified by silica gel column chromatography [solvent: chloroform/methanol (95:5)] to give 544 mg of 1,2',6'-tris-N-benzyloxycarbonyl-2''-N-{Nα-benzyloxycarbonyl-Nγ-[3-(3,12-di-O-acetyldeoxycholylamino)propyl]-L-glutaminyl}-5-de-O-methyl-KA-6606I as a colorless solid.

Specific rotation: $[\alpha]_D^{25}$ +46° (c=2, CHCl$_3$)
$^1$H-NMR value: $\delta_{CDCl_3}^{TMS}$, ppm
0.70 (3H, s, deoxycholyl CH$_3$-18)
0.80 (3H, br.d, deoxycholyl CH$_3$-21)
0.91 (3H, s, deoxycholyl CH$_3$-19)
2.02 (3H, s, COCH$_3$)
2.07 (3H, s, COCH$_3$)
Elemental analysis for C$_{84}$H$_{114}$N$_8$O$_{20}$:

|  | C | H | N |
|---|---|---|---|
| Calculated (%): | 64.85 | 7.39 | 7.20 |
| Found (%): | 65.11 | 7.30 | 7.29 |

(b) The N-protected compound (544 mg) obtained in (a) above was reacted and worked up in the same way as in Example 1, (b) to give 343.5 mg of the hydrochloride of the captioned compound as a colorless solid.

Specific rotation: $[\alpha]_D^{26}$ +89° (c=1, H$_2$O)
$^1$H-NMR value: $\delta_{D_2O}^{TMS}$, ppm ~0.7–1.0 (9H, deoxycholyl CH$_3$×3)
1.32 (3H, d, J=7 Hz, C$^{6'}$—CH$_3$)
2.01 (3H, s, COCH$_3$)
2.12 (3H, s, COCH$_3$)
3.15 (3H, s, N—CH$_3$)
5.45 (1H, d, J=3.5 Hz, H-1')
Elemental analysis for C$_{52}$H$_{90}$N$_8$O$_{12}$.4HCl.H$_2$O:

|  | C | H | N | Cl |
|---|---|---|---|---|
| Calculated (%): | 52.79 | 8.18 | 9.47 | 11.98 |
| Found (%): | 52.21 | 8.34 | 9.07 | 12.30 |

EXAMPLE 46

Production of 2''-N-{Nγ-[3-(3,12-di-O-propyldeoxycholylamino)propyl]-L-glutaminyl}-5-di-O-methyl-KA-6606I:

(a) 315 mg of 1,2',6'-tris-N-benzyloxycarbonyl-5-de-O-methyl-KA-6606I and 500 mg of an N-hydroxysuccinimide ester of Nα-benzyloxycarbonyl-Nγ-[3-(3,12-di-O-allyl-deoxycholylamino)propyl]-L-glutamine were reacted and worked up in the same way as in Example 1, (a). The reaction product was purified by silica gel column chromatography [solvent: chloroform/methanol (20:1)] to give 256 mg of 1,2',6'-tris-N-benzyloxycarbonyl-2''-N-{Nα-benzyloxycarbonyl-Nγ-[3-(3,12-di-O-allyl-deoxycholylamino)-propyl]-L-glutaminyl}-5-de-O-methyl-KA-6606I as a colorless solid.

Specific rotation: $[\alpha]_D^{24}$ +41° (c=1, CHCl$_3$)
$^1$H-NMR value: $\delta_{CDCl_3}^{TMS}$, ppm
0.65 (3H, s, deoxycholyl CH$_3$-18)
0.91 (6H, br.s, deoxycholyl CH$_3$-19, 21)
1.04 (3H, d, J=7 Hz, C$^{6'}$—CH$_3$)
5.90 (2H, octet, —CH$_2$—CH=CH$_2$)
~7.30 (20H, aromatic H)
Elemental analysis for C$_{86}$H$_{118}$N$_8$O$_{18}$:

|  | C | H | N |
|---|---|---|---|
| Calculated (%): | 66.56 | 7.66 | 7.22 |
| Found (%): | 66.72 | 7.83 | 7.10 |

(b) 236 mg of the N-protected compound obtained in (a) was reacted and worked up in the same way as in Example 1, (b) to give 136 mg of the hydrochloride of the captioned compound as a colourless solid.

Specific rotation: $[\alpha]_D^{23}$ +65° (c=1, H$_2$O)
IR value: $\nu_{max}^{KBr}$, cm$^{-1}$ 1625 (amide I)
$^1$H-NMR value: $\delta_{D_2O}^{TMS}$, ppm
1.34 (3H, d, J=7 Hz, C$^{6'}$—CH$_3$)
3.16 (3H, s, N—CH$_3$)
5.04 (1H, br.s, H-1')
Elemental analysis for C$_{54}$H$_{98}$N$_8$O$_{10}$.4HCl.2H$_2$O:

|  | C | H | N | Cl |
|---|---|---|---|---|
| Calculated (%): | 54.00 | 8.88 | 9.33 | 11.81 |
| Found (%): | 53.87 | 9.01 | 9.16 | 11.62 |

EXAMPLE 47

Production of 2''-N-{N$^\gamma$-[(s)-1-carboxy-2-phenylethyl]-L-glutaminyl}-5-de-O-methyl-KA-6606I:

(a) 543 mg of 1,2',6'-tris-N-benzyloxycarbonyl-5-de-O-methyl-KA-6606I and 421 mg of an N-hydroxysuccinimide ester of N$^\alpha$-benzyloxycarbonyl-N$^\gamma$-[(s)-1-benzyloxycarbonyl-2-phenylethyl]-L-glutamine were reacted and worked up in the same way as in Example, (a). The reaction product was purified by silica gel column chromatography [solvent: chloroform/methanol (98:2)] to give 436 mg of 1,2',6'-tris-N-benzyloxycarbonyl-2''-N-{N$^\alpha$-benzyloxycarbonyl-N$^\gamma$-[(s)-1-benzyloxycarbonyl-2-phenylethyl]-L-glutaminyl}-5-de-O-methyl-KA-6606I as a colorless solid.

Specific rotation: $[\alpha]_D^{25}+8°$ (c=2, CHCl$_3$)
IR value: $\nu_{max}^{CHCl_3}$, cm$^{-1}$ 1623 (amide I)
$^1$H-NMR value: $\delta_{CDCl_3}^{TMS}$, ppm
1.04 (3H, br.d, C$^{6'}$—CH$_3$)
~7.3 (30H, aromatic H)
Elemental analysis for C$_{69}$H$_{79}$N$_7$O$_{17}$:

|  | C | H | N |
|---|---|---|---|
| Calculated (%): | 64.83 | 6.23 | 7.67 |
| Found (%): | 64.58 | 6.49 | 7.80 |

(b) The N-protected compound (436 mg) obtained in (a) above was reacted and worked up in the same way as in Example 1, (b) to give 248 mg of the hydrochloride of the captioned compound as a colorless solid.

Specific rotation: $[\alpha]_D^{22}+72°$ (c=1.09, H$_2$O)
$^1$H-NMR value: $\delta_{D_2O}^{TMS}$, ppm
1.33 (3H, d, J=6.5 Hz, C$^{6'}$—CH$_3$)
3.20 (3H, s, N—CH$_3$)
5.51 (1H, d. J=3.5 Hz, H-1')
7.41 (5H, s, aromatic H)
Elemental analysis for C$_{30}$H$_{49}$N$_7$O$_9$4HCl1H$_2$O

|  | C | H | N | Cl |
|---|---|---|---|---|
| Calculated (%): | 44.18 | 6.80 | 12.02 | 17.39 |
| Found (%): | 43.61 | 7.04 | 11.55 | 17.78 |

EXAMPLE 48

Production of 2''-N-{N$^\gamma$-[5-(decanoylamino)-5-(methoxycarbonyl)pentyl]-L-glutaminyl}-5-de-O-methyl-KA-6606I:

(a) 550 mg of 1,2',6'-tris-N-benzyloxycarbonyl-5-de-O-methyl-KA-6606I and 390 mg of an N-hydroxysuccinimide ester of N$^\alpha$-benzyloxycarbonyl-N$^\gamma$-[5-(decanoylamino)-5-(methoxycarbonyl)pentyl]-L-glutamine were reacted and worked up in the same way as in Example 1, (a). The reaction product was purified by silica gel column chromatography [solvent: chloroform/ethyl acetate/acetone (1:1:1→2:2:3→1:1:2) to give 328 mg of 1,2',6'-tris-N-benzyloxycarbonyl-2''-N-{N$^\alpha$-benzyloxycarbonyl-N$^\gamma$-([5-(decanoylamino)-5-(methoxycarbonyl)pentyl]-L-glutamin-yl}-5-de-O-methyl-KA-6606I as a colorless solid.

Specific rotation: $[\alpha]_D^{24}+22°$ (c=1, CHCl$_3$)
IR value: $\nu_{max}^{CHCl_3}$, cm$^{-1}$ 1705 (urethane), 1660 (amide I), 1500 (amide II)
$^1$H-NMR value: $\delta_{CDCl_3}^{TMS}$, ppm
0.87 [3H, t, —(CH$_2$)$_8$—CH$_3$]
1.04 (3H, d, J=6.5 Hz, C$^{6'}$—CH$_3$)
1.25 (br.s, decanoyl methylene portion)
3.68 (3H, s, COOCH$_3$)
~7.3 (20H, m, aromatic H)
Elemental analysis for C$_{70}$H$_{96}$N$_8$O$_{18}$:

|  | C | H | N |
|---|---|---|---|
| Calculated (%): | 62.86 | 7.23 | 8.38 |
| Found (%): | 62.98 | 7.50 | 8.07 |

(b) 53 mg of the N-protected compound obtained in (a) was reacted and worked up in the same way as in Example 1, (b) to give 33 mg of the hydrochloride of the captioned compound as a colorless solid.

Specific rotation: $[\alpha]_D^{22}+52°$ (c=1, H$_2$O)
IR value: $\nu_{max}^{KBr}$, cm$^{-1}$ 1625 (br. amide I)
H-NMR value: $\delta_{D_2O}^{TMS}$, ppm
0.88 [3H, t, —(CH$_2$)$_8$—C$_3$]
1.30 (br.s, decanoyl methylene portion)
1.36 (3H, d, J=6.5 Hz, C$^{6'}$—CH$_3$)
3.19 (3H, s, N—CH$_3$)
3.78 (3H, s, COOCH$_3$)
5.50 (1H, d, J=3.5 Hz, H-1')
Elemental analysis for C$_{38}$H$_{72}$N$_8$O$_{10}$.4HCl.2H$_2$O:

|  | C | H | N | Cl |
|---|---|---|---|---|
| Calculated (%): | 46.43 | 8.20 | 11.40 | 14.43 |
| Found (%): | 46.12 | 8.35 | 11.61 | 14.80 |

EXAMPLE 49

Production of 2''-N-{N$^\gamma$-[5-(decanoylamino)-1-(methoxycarbonyl)pentyl]-L-glutaminyl}-5-de-O-methyl-KA-6606I:

(a) 930 mg of 1,2',6'-tris-N-benzyloxycarbonyl-5-de-O-methyl-KA-6606I and 660 mg of an N-hydroxysuccinimide ester of N$^\alpha$-benzyloxycarbonyl-N$^\gamma$-[5-(decanoylamino)-1-(methoxycarbonyl)pentyl]-L-glutamine were reacted and worked up in the same way as in Example 1, (a). The reaction product was purified by silica gel column chromatography [solvent: chloroform/ethyl acetate-acetone (1:1:1→2:2:3)] to give 677 mg of 1,2',6'-tris-N-benzyloxycarbonyl-2''-N-{N$^\alpha$-benzyloxycarbonyl-N$^\gamma$-[5-(decanoylamino-1-(methoxycarbonyl)pentyl]-L-glutaminyl}-5-de-O-methyl-KA-6606I as a colorless solid.

Specific rotation: $[\alpha]_D^{24}+6°$ (c=1, CHCl$_3$)
IR value: $\nu_{max}^{CHCl_3}$, cm$^{-1}$ 1710 (urethane), 1660 (amide I), 1500 (amide II)
$^1$H-NMR value: $\delta_{CDCl_3}^{TMS}$, ppm
0.88 [3H, t, —(CH$_2$)$_8$—CH$_3$]
1.06 (3H, d, J=6.5 Hz, C$^{6'}$—CH$_3$)
1.24 (br.s, decanoyl methylene portion)
3.76 (3H, s, COOCH$_3$)
~7.3 (20H, m, aromatic H)
Elemental analysis for C$_{70}$H$_{96}$N$_8$O$_{18}$:

|  | C | H | N |
|---|---|---|---|
| Calculated (%): | 62.86 | 7.23 | 8.38 |
| Found (%): | 63.01 | 7.46 | 8.15 |

(b) 70 mg of the N-protected compound obtained in (a) was reacted and worked up in the same way as in Example 1, (b) to give 46 mg of the hydrochloride of the captioned compound as a colorless solid.

Specific rotation: $[\alpha]_D^{22}+56°$ (c=1, H$_2$O)
IR value: $\nu_{max}^{KBr}$, cm$^{-1}$ 1630 (amide I)

$^1$H-NMR value: $\delta_{D_2O}{}^{TMS}$, ppm
0.88 [3H, t, —(CH$_2$)$_8$—C$\underline{H_3}$]
1.30 (br.s, decanoyl methylene portion)
1.36 (3H, d, J=6.5 Hz, C$^{6'}$—CH$_3$)
3.19 (3H, s, N—CH$_3$)
3.78 (3H, s, COOCH$_3$)
5.50 (1H, d, J=3.5 Hz, H-1')
Elemental analysis for C$_{38}$H$_{72}$N$_8$O$_{10}$.4HCl.2H$_2$O:

|  | C | H | N | Cl |
|---|---|---|---|---|
| Calculated (%): | 46.43 | 8.20 | 11.40 | 14.43 |
| Found (%): | 46.70 | 8.51 | 11.53 | 14.66 |

EXAMPLE 50

Production of 2''-N-[N$^\gamma$-(3-decanoylaminopropyl)-L-glutaminyl]fortimicin A:

(a) 276 mg of 1,2',6'-tris-N-benzyloxycarbonylfortimicin A and 210 mg of an N-hydroxysuccinimide ester of N$^\alpha$-benzyloxycarbonyl-N-$\gamma$-(3-decanoylaminopropyl)-L-glutamine were reacted and worked up in the same way as in Exampel 1, (a). The reaction product was purified by silica gel column chromatography [solvent: chloroform/methanol (40:1→20:1)] to give 240 mg of 1,2',6'-tris-N-benzyloxycarbonyl-2''-N-[N$^\alpha$-benzyloxycarbonyl-N$\gamma$-(3-decanoylaminopropyl)-L-glutaminyl]fortimicin A as a colorless solid.

Specific rotation: [α]$_D{}^{21}$+31° (c=1, CHCl$_3$)
IR value: $\nu_{max}{}^{CHCl_3}$, cm$^{-1}$ 1710 (urethane), 1640 (amide I), 1500 (amide II)
$^1$H-NMR value: $\delta_{CDCl_3}{}^{TMS}$, ppm
0.87 [3H, t, J=7 Hz, —(CH$_2$)$_8$—C$\underline{H_3}$]
1.24 (br.s, decanoyl methylene portion)
3.32 (3H, s, O—CH$_3$)
~7.32 (20H, br.s, aromatic H)
Elemental analysis for C$_{67}$H$_{92}$N$_8$O$_{17}$:

|  | C | H | N |
|---|---|---|---|
| Calculated (%): | 62.80 | 7.24 | 8.74 |
| Found (%): | 63.01 | 7.43 | 8.48 |

(b) The N-protected compound (240 mg) obtained in (a) above was reacted and worked up in the same way as in Example 1, (b) to give 157 mg of the hydrochloride of the captioned compound as a colorless solid.

Specific rotation: [α]$_D{}^{22}$+67° (c=1, H$_2$O)
IR value: $\nu_{max}{}^{KBr}$, cm$^{-1}$ 1630 (amide I)
$^1$H-NMR value: $\delta_{D_2O}{}^{TMS}$, ppm
0.92 [3H, t, J=7 Hz, —(CH$_2$)$_8$—C$\underline{H_3}$]
1.33 (br.s, decanoyl methylene portion)
1.40 (3H, d, J=7 Hz, C$^{6'}$—CH$_3$)
3.24 (3H, s, N—CH$_3$)
3.28 (4H, t, —NH—C$\underline{H_2}$—CH$_2$—C$\underline{H_2}$—NH—)
3.56 (3H, s, O—CH$_3$)
5.36 (1H, d, J=3.5 Hz, H-1')
Elemental analysis for C$_{35}$H$_{68}$N$_8$O$_9$.4HCl.H$_2$O:

|  | C | H | N | Cl |
|---|---|---|---|---|
| Calculated (%): | 46.25 | 8.21 | 12.33 | 15.61 |
| Found (%): | 46.11 | 8.40 | 12.05 | 15.37 |

EXAMPLE 51

Production of 2''-N-[S-(p-methoxybenzyl)-L-cysteinyl]-5-de-O-methyl-KA-6606I:

(a) 1.22 g of 1,2',6'-tris-N-(p-methoxybenzyloxycarbonyl)-5-de-O-methyl-KA-6606 II was dissolved in 40 ml of dioxane, and 840 mg of an N-hydroxysuccinimide ester of S-(p-methoxybenzyl)-N-(p-methoxybenzyloxycarbonyl)-L-cysteinylglycine and 2 ml of triethylamine were added. The mixture was left to stand overnight at 37° C. The solvent was evaporated from the reaction mixture, and the residue was dissolved in chloroform. The solution was washed with water, dried and then separated and purified by silica gel column chromatography [solvent: chloroform/methanol (40:1→20:1)] to give 866 mg of 1,2',6'-tris-N-(p-methoxybenzyloxycarbonyl)-2''-N-[S-(p-methoxybenzyl)-N-(p-methoxybenzyloxycarbonyl)-L-cysteinyl]-5-de-O-methyl-KA-6606I as a colorless solid.

Specific rotation: [α]$_D{}^{25}$+25° (c=1, CHCl$_3$)
$^1$H-NMR value: $\delta_{CDCl_3}{}^{TMS}$, ppm
1.02 [3H, d, J=7 Hz, C$^{6'}$—CH$_3$]
3.76, 3.78, 3.79, 3.80, 3.81 (each 3H, s,

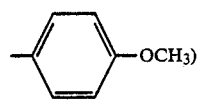

OCH$_3$)

6.7–7.0 (10H, m, aromatic H)
7.1–7.4 (10H, m, aromatic H)
Elemental analysis for C$_{63}$H$_{78}$N$_6$O$_{19}$S:

|  | C | H | N | S |
|---|---|---|---|---|
| Calculated (%): | 60.27 | 6.26 | 6.69 | 2.55 |
| Found (%): | 60.41 | 6.39 | 6.82 | 2.44 |

(b) 732 mg of the N-protected compound obtained in (a) was dissolved in 8 ml of acetic acid, and 720 mg of p-toluenesulfonic acid monohydrate and 0.4 ml of anisole were added. The mixture was left to stand at room temperature for 2 hours. The reaction mixture was concentrated under reduced pressure, and 50 ml of water and 50 ml of chloroform were added to the residue. The mixture was shaken, and the aqueous layer was separated. The aqueous layer was washed with chloroform and then neutralized. Water was added to make to total amount 250 ml. The solution was charged on a column of CM-Sephadex C-25 (NH$_4{}^+$ form). The column was washed with water and then eluted with water and 0.5N aqueous ammonia by the concentration gradient method. Fractions containing the captioned compound were collected and lyophilized. The resulting free base was dissolved in water, and 4N sulfuric acid was added to the solution to adjust its pH to 5.8. The solution was then lyophilized to give 314 mg of the sulfate of the captioned compound as a colorless solid.

Specific rotation: [α]$_D{}^{25}$+72° (c=1, H$_2$O)
$^1$H-NMR value: $\delta_{D_2O}{}^{TMS}$, ppm
1.34 (3H, d, J=6.5 Hz, C$^{6'}$—CH$_3$)
3.03 (2H, d, CH—C$\underline{H_2}$—S)
3.17 (3H, s, N—CH$_3$)
3.83 (2H, s,

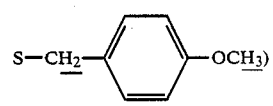

S—C$\underline{H_2}$—

OCH$_3$)

3.85 (3H, s, 4.21 (2H, s, COCH₂NH)
5.40 (1H, d, J=3.5 Hz, H-1')
7.02 (2H, d, J=8.5 Hz, aromatic H)
7.38 (2H, d, J=8.5 Hz, aromatic H)
Elemental analysis for C₂₇H₄₆N₆O₇S.2H₂SO₄.H₂O:

|  | C | H | N | S |
|---|---|---|---|---|
| Calculated (%): | 39.89 | 6.45 | 10.34 | 11.83 |
| Found (%): | 40.05 | 6.69 | 10.20 | 11.65 |

EXAMPLE 52

Production of 2''-N-[S-(p-nitrobenzyl)-L-cysteinyl]-5-de-O-methyl-KA-6606I:

(a) 810 mg of 1,2',6'-tris-N-(p-methoxybenzyloxycarbonyl)-5-de-O-methyl-KA-6606II and 810 mg of an N-hydroxysuccinimide ester of S-(p-nitrobenzyl)-N-(p-methoxybenzyloxycarbonyl)-L-cysteinylglycine were reacted and worked up in the same way as in Example 51, (a). The reaction product was purified by silica gel column chromatography [solvent: chloroform/methanol (40:1)] to give 666 mg of 1,2',6'-tris-N-(p-methoxybenzyloxycarbonyl)-2''-N-[S-(p-nitrobenzyl)-N-(p-methoxybenzyloxycarbonyl)-L-cysteinyl]-KA-6606I as a colorless solid.

Specific rotation: $[\alpha]_D^{20} +34°$ (c=1, CHCl₃)
¹H-NMR value: $\delta_{CDCl_3}^{TMS}$, ppm
1.01 [3H, d, J=7 Hz, C⁶'—CH₃]
3.75 (12H, s,

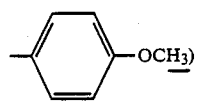

6.70–6.86 (8H,

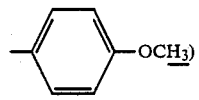

7.08–7.28 (8H,

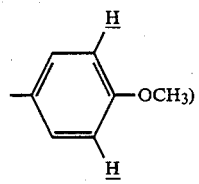

7.37, 8.05 (each 2H, d, J=8 Hz,

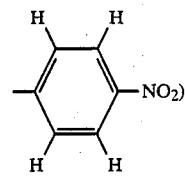

Elemental analysis for C₆₂H₇₅N₇O₂₀S:

|  | C | H | N | S |
|---|---|---|---|---|
| Calculated (%): | 58.62 | 5.95 | 7.72 | 2.52 |
| Found (%): | 58.06 | 5.88 | 7.43 | 2.47 |

(b) 645 mg of the N-protected compound obtained in (a) was reacted and worked up in the same way as in Example 51, (b) to give 680 mg of the sulfate of the captioned compound as a pale yellow solid.

Specific rotation: $[\alpha]_D^{20} +82°$ (c=1, H₂O)
¹H-NMR value: $\delta_{D_2O}^{TMS}$, ppm
1.35 (3H, d, J=6.7 Hz, C⁶'—CH₃)
3.18 (3H, s, N—CH₃)
3.97 (2H, s,

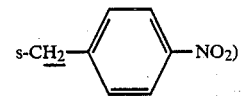

4.22 (2H, s, CO—CH₂—NH)
5.45 (1H, d, J=3.5 Hz, H-1')
7.64 (2H, d, J=8.5 Hz, aromatic H)
8.26 (2H, d, J=8.5 Hz, aromatic H)
Elemental analysis for C₂₆H₄₃N₇O₈S.2H₂SO₄.H₂O:

|  | C | H | N | S |
|---|---|---|---|---|
| Calculated (%): | 37.72 | 5.97 | 11.84 | 11.62 |
| Found (%): | 37.56 | 6.18 | 11.36 | 11.51 |

EXAMPLE 53

Production of 2''-N-(S-diphenylmethyl-L-cysteinyl)-5-de-O-methyl-KA-6606I:

(a) 756 mg of 1,2',6'-tris-N-(p-methoxybenzyloxycarbonyl)-5-de-O-methyl-KA-6606II and 700 mg of an N-hydroxysuccinimide ester of S-diphenylmethyl-N-(p-methoxybenzyloxycarbonyl)-L-cysteinylglycine were reacted and worked up in the same way as in Example 51, (a). The reaction product was purified by silica gel column chromatography [solvent: chloroform/methanol (40:1)] to give 640 mg of 1,2',6'-tris-N-(p-methoxybenzyloxycarbonyl)-2''-N-[S-diphenylmethyl-N-(p-methoxybenzyloxycarbonyl)-L-cysteinyl]-5-de-O-methyl-KA-6606I as a colorless solid.

Specific rotation: $[\alpha]_D^{24} +25°$ (c=1, CHCl₃)
¹H-NMR value: $\delta_{CDCl_3}^{TMS}$, ppm
1.02 [3H, d, J=6 Hz, C⁶'—CH₃]
3.74 (3H, s, —O—CH₃)
3.78 (6H, s, —O—CH₃)
3.79 (3H, s, —O—CH₃)
6.8–7.0 (8H, m, aromatic H)
7.1–7.5 (18H, m, aromatic H)
Elemental analysis for C₆₈H₈₀N₆O₁₈S:

|  | C | H | N | S |
|---|---|---|---|---|
| Calculated (%): | 62.75 | 6.20 | 6.46 | 2.46 |
| Found (%): | 62.98 | 6.37 | 6.55 | 2.20 |

(b) 630 mg of the N-protected compound obtained in (a) was reacted and worked up in the same way as in Example 51, (b) to give 300 mg of the sulfate of the captioned compound as a colorless solid.

Specific rotation: $[\alpha]_D^{26} +59°$ (c=1, H$_2$O)
$^1$H-NMR value: $\delta_{D_2O}^{TMS}$, ppm
1.34 (3H, d, J=6.5 Hz, C$^6{}'$—CH$_3$)
3.00 (2H, d, —CH—C$\underline{H_2}$—S)
3.18 (3H, s, N—CH$_3$)
5.40 (2H, br.s, H-1',

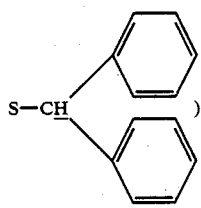

)

7.0–7.7 (10H, m, aromatic H)
Elemental analysis for C$_{32}$H$_{48}$N$_6$O$_6$S$\cdot$2H$_2$SO$_4$$\cdot$H$_2$O:

|  | C | H | N | S |
|---|---|---|---|---|
| Calculated (%): | 44.74 | 6.34 | 9.78 | 11.20 |
| Found (%): | 44.98 | 6.65 | 10.05 | 11.03 |

EXAMPLE 54

Production of 2''-N-[S-(4-picolyl)-L-cysteinyl]-5-de-O-methyl-KA-6606I:

(a) 1.77 g of 1,2',6'-tris-N-(p-methoxybenzyloxycarbonyl)-5-de-O-methyl-KA-6606II and 1.33 g of an N-hydroxysuccinimide ester of S-(4-picolyl)-N-(p-methoxybenzyloxycarbonyl)-L-cysteinylglycine were reacted and worked up in the same way as in Example 51, (a). The reaction product was purified by silica gel column chromatography [solvent: chloroform/methanol (30:1→20:1)], then aluminum column chromatography [solvent: chloroform/methanol (20:1)] to give 901 mg of 1,2',6'-tris-N-(p-methoxybenzyloxycarbonyl)-2''-N-[S-(4-picolyl)-N-(p-methoxybenzyloxycarbonyl)-L-cysteinyl]-5-de-O-methyl-KA-6606I as a colorless solid.

Specific rotation: $[\alpha]_D^{26} +30°$ (c=1, CHCl$_3$)
$^1$H-NMR value: $\delta_{CDCl_3}^{TMS}$, ppm
1.02 [3H, d, J=6 Hz, C$^6{}'$—CH$_3$)
3.74 (3H, s, O—CH$_3$)
3.77 (6H, s, O—CH$_3$)
3.79 (3H, s, O—CH$_3$)
6.8–6.95, 7.15–7.35, 8.42 (total 20H, m, aromatic H)
Elemental analysis for C$_{61}$H$_{75}$N$_7$O$_{18}$S:

|  | C | H | N | S |
|---|---|---|---|---|
| Calculated (%): | 59.74 | 6.16 | 7.99 | 2.61 |
| Found (%): | 59.09 | 6.28 | 7.52 | 2.38 |

(b) 645 mg of the N-protected compound obtained in (a) was reacted and worked up in the same way as in Example 51, (b) to give 288 mg of the sulfate of the captioned compound as a colorless solid.

Specific rotation: $[\alpha]_D^{22} +84°$ (c=1, H$_2$O)
$^1$H-NMR value: $\delta_{D_2O}^{TMS}$, ppm
1.34 (3H, d, J=6.5 Hz, C$^6{}'$—CH$_3$)
3.01 (2H, m, —CH—C$\underline{H_2}$—S)
3.18 (3H, s, N—CH$_3$)
3.79 (2H, s,

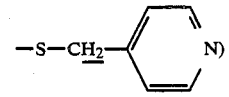

4.19 (2H, s, CO—C$\underline{H_2}$—NH)
5.45 (1H, d, J=3.5 Hz, H-1')
7.54, 8.54 (each 2H, d, aromatic H)
Elemental analysis for C$_{25}$H$_{43}$N$_7$O$_6$S$\cdot$5/2H$_2$SO$_4$$\cdot$H$_2$O:

|  | C | H | N | S |
|---|---|---|---|---|
| Calculated (%): | 36.06 | 6.03 | 11.77 | 13.48 |
| Found (%): | 36.31 | 6.29 | 11.55 | 13.50 |

EXAMPLE 55

Production of 2''-N-(S-decanoyl-L-cysteinyl)-5-de-O-methyl-KA-6606I:

(a) One gram of 1,2',6'-tris-N-(p-methoxybenzyloxycarbonyl)-5-de-O-methyl-KA-6606II and 628 mg of an N-hydroxysucciiimide ester of N-(p-methoxybenzyloxycarbonyl)-S-decanoyl-L-cysteinylglycine were reacted and worked up in the same way as in Example 51, (a). The reaction product was purified by silica gel column chromatography [solvent: chlorofrom/methanol (98:2)] to give 401 mg of 1,2',6'-tris-N-(p-methoxybenzyloxycarbonyl)-2''-N-[S-decanoyl-N-(p-methoxybenzyloxycarbonyl)-L-cysteinyl]-5-de-O-methyl-KA-6606I as a colorless solid.

Specific rotation: $[\alpha]_D^{22} +21°$ (c=2, CHCl$_3$)
IR value: $\nu_{max}^{CHCl_3}$, cm$^{-1}$ 1636 (amide I)
$^1$H-NMR value: $\delta_{CDCl_3}^{TMS}$, ppm
0.87 [3H, t, (CH$_2$)$_8$—C$\underline{H_3}$]
1.01 [3H, d, J=6.5 Hz, C$^6{}'$—CH$_3$)
2.89, 3.07 (total 3H, s, N—CH$_3$) rotational isomer)
3.76, 3.77, 3.79 (total 12H, s, OCH$_3$)
Elemental analysis for C$_{65}$H$_{88}$N$_6$O$_{19}$S:

|  | C | H | N | S |
|---|---|---|---|---|
| Calculated (%): | 60.54 | 6.88 | 6.52 | 2.49 |
| Found (%): | 60.27 | 6.94 | 6.29 | 2.14 |

(b) 361 mg of the N-protected compound obtained in (a) and 360 mg of anisole were dissolved in 4 ml of acetic acid, and 270 mg of p-toluenesulfonic acid monohydrate was added. The mixture was stirred at room temperature for 2 hours. The reaction mixture was concentrated to dryness under reduced pressure. Water and benzene were added to the residue, and the aqueous layer was separated. The aqueous layer was washed with benzene and lyophilized to give 350 mg of the p-toluenesulfonate of the captioned compound as a colorless solid.

Specific rotation: $[\alpha]_D^{23} +42°$ (c=2, H$_2$O)
$^1$N-NMR value: $\delta_{D_2O}^{TMS}$, ppm 0.87 [3H, t, (CH$_2$)$_8$—C$\underline{H}_3$]
1.12 (3H, d, J=7 Hz, C$^{6'}$—CH$_3$)
2.20 (12H, s, C$\underline{H}_3$-, —SO$_3$H)
2.84 (3H, s, —N—CH$_3$)
5.31 (1H, br.s H-1')
7.15 (8H, d, J=8 Hz, aromatic H)
7.62 (8H, d, J=8 Hz, aromatic H)
Elemental analysis for C$_{29}$H$_{56}$N$_6$O$_7$S$_4$·p-TsOH4H$_2$O:

|  | C | H | N | S |
|---|---|---|---|---|
| Calculated (%): | 49.12 | 6.94 | 6.03 | 11.50 |
| Found (%): | 49.73 | 7.29 | 5.69 | 11.92 |

EXAMPLE 56

Production of 2''-N-[N$^\gamma$-(3-decanoyloxypropyl)-L-glutamyl]-5-demethoxy-KA-6606I:

(a) 75 mg of 1,2',6'-tris-N-benzyloxycarbonyl-5-demethoxy-KA-6606I and 98 mg of an N-hydroxysuccinimide ester of N$^\alpha$-benzyloxycarbonyl-N$^\gamma$-(3-decanoyloxypropyl)-L-glutamic acid were reacted and worked up in the same way as in Example 1, (a). The reaction product was purified by silica gel preparative thin-layer chromatography [solvent: chloroform/ethyl acetate/acetone (2:2:1)] to give 65 mg of 1,2',6'-tris-N-benzyloxycarbonyl-2''-N-[N$^\alpha$-benzyloxycarbonyl-N$^\gamma$-(3-decanoyloxypropyl)-L-glutamyl]-5-demethoxy-KA-6606I as a colorless solid.

Specific rotation: $[\alpha]_D^{22}$+31° (c=1, CHCl$_3$)
IR value: $\nu_{max}^{CHCl_3}$, cm$^{-1}$ 1705 (urethane, ester), 1635 (amide I), 1495 (amide II)
$^1$H-NMR value: $\delta_{CDCl_3}^{TMS}$, ppm
0.88 [3H, t, —(CH$_2$)$_8$—C$\underline{H}_3$]
1.05 (3H, d, J=7 Hz, C$^{6'}$—CH$_3$)
1.28 (br.s, decanoyl methylene portion)
7.3 (20H, aromatic H)
Elemental analysis for C$_{66}$H$_{88}$N$_6$O$_{17}$:

|  | C | H | N |
|---|---|---|---|
| Calculated (%): | 64.06 | 7.17 | 6.79 |
| Found (%): | 64.28 | 7.02 | 6.58 |

(b) 54 mg of the N-protected compound obtained in (a) was reacted and worked up in the same way as in Example 1, (b) to give 34 mg of the hydrochloride of the captioned compound as a colorless solid.

Specific rotation: $[\alpha]_D^{22}$+60° (c=1, H$_2$O)
IR value: $\nu_{max}^{KBr}$, cm$^{-1}$ 1710 (ester), 1610 (amide I)
$^1$H-NMR value: $\delta_{D_2O}^{TMS}$, ppm
0.86 [3H, t, —(CH$_2$)$_8$—C$\underline{H}_3$]
1.30 (decanoyl methylene portion)
1.36 (3H, d, J=7 Hz, C$^{6'}$—CH$_3$)
3.19 (3H, s, N—CH$_3$)
5.49 (1H, d, J=3.5 Hz, H-1')
Elemental analysis for C$_{34}$H$_{64}$N$_6$O$_9$·4HCl·H$_2$O:

|  | C | H | N | Cl |
|---|---|---|---|---|
| Calculated (%): | 47.22 | 8.16 | 9.72 | 16.40 |
| Found (%): | 46.97 | 8.40 | 9.55 | 16.13 |

EXAMPLE 57

Production of 2''-N-[N$^\gamma$-(3-decanoylaminopropyl)-L-glutaminyl]-KA-7038I:

(a) One hundred milligrams of 1,2',6'-tris-N-benzyloxycarbonyl-KA-7038I and 70 mg of an N-hydroxysuccinimide ester of N$^\alpha$-benzyloxycarbonyl-N$^\gamma$-(3-decanoylaminopropyl)-L-glutamine were reacted and worked up in the same way as in Example 1, (a). The reaction product was purified by silica gel column chromatography [solvent: chloroform/methanol (40:1)] to give 63 mg of 1,2',6'-tris-N-benzyloxycarbonyl-2''-N-[N$^\alpha$-benzyloxycarbonyl-N$^\gamma$-(3-decanoylaminopropyl)-L-glutraminyl]-KA-7038I as a colorless solid.

Specific rotation: $[\alpha]_D^{24}$+32° (c=1, CHCl$_3$)
$^1$H-NMR value: $\delta_{CDCl_3}^{TMS}$, ppm
0.88 [3H, t, —(CH$_2$)$_8$—C$\underline{H}_3$]
2.91 (6H, s, N—CH$_3$)
3.24 (3H, s, O—CH$_3$)
Elemental analysis for C$_{67}$H$_{92}$N$_8$O$_{16}$:

|  | C | H | N |
|---|---|---|---|
| Calculated (%): | 63.59 | 7.33 | 8.86 |
| Found (%): | 63.63 | 7.12 | 8.65 | in (a) was reacted and worked up in the same way as in Example 1, (b) to give 34 mg of the hydrochloride of the captioned compound as a colorless solid.

Specific rotation: $[\alpha]_D^{21}$+66° (c=1, H$_2$O)
$^1$H-NMR value: $\delta_{D_2O}^{TMS}$, ppm
0.90 [3H, t, —(CH$_2$)$_8$—C$\underline{H}_3$]
2.75 (3H, s, C$^{6'}$—N—CH$_3$)
3.18 (3H, s, C$^4$—N—CH$_3$)
3.44 (3H, s, O—CH$_3$)
5.32 (1H, d, J=3.5 Hz, H-1')
Elemental analysis for C$_{35}$H$_{68}$N$_8$O$_8$·4HCl·H$_2$O:

|  | C | H | N | Cl |
|---|---|---|---|---|
| Calculated (%): | 47.08 | 8.35 | 12.55 | 15.88 |
| Found (%): | 46.61 | 8.58 | 12.33 | 16.06 |

| FORMULATION EXAMPLE 1 | |
|---|---|
| Enteric-coated tablets | Weight per tablet (mg) |
| Main Ingredient | |
| Compound of Example 36 (hydrochloride) | 200 |
| Excipient | |
| Hardened oil | 30 |
| Microcrystalline cellulose | 30 |
| Disintegrant | |
| Carboxymethyl cellulose · calcium | 25 |
| Binder | |
| Hydroxypropyl cellulose | 10 |
| Lubricant | |
| Magnesium stearate | 5 |
| Coating agent | |
| Hydroxypropylmethyl cellulose phthalate | 30 |
| Total | 330 |

The main ingredient, excipient, disintegrant and binder were mixed and granulated, and then the lubricant was added. The mixture was tableted into tablets each weighing 300 mg by means of a pounder having a diameter of 9.5 mm. The tablets were then coated each with 30 mg of the coating agent to form enteric-coated tablets.

| FORMULATION EXAMPLE 2 | |
| --- | --- |
| Enteric-coated tablets | Weight per tablet (mg) |
| Main ingredient | |
| Compound of Example 36 | 200 |
| Excipient | |
| Corn starch | 25 |
| Lactose | 30 |
| Microcrystalline cellulose | 30 |
| Binder | |
| Hydroxypropyl cellulose | 10 |
| Lubricant | |
| Magnesium stearate | 5 |
| Coating agent | |
| Hydroxypropylmethylcellulose phthalate | 30 |
| Total | 330 |

The main ingredient, excipient, binder and lubricant were mixed and granulated. The mixture was tableted into tablets each weighing 300 mg by means of a pounder having a diameter of 9.5 mm. The tablets were then coated each with 30 mg of the coating agent to form enteric-coated tablets.

| FORMULATION EXAMPLE 3 | |
| --- | --- |
| Enteric-coated capsules | Weight per capsule (mg) |
| Main ingredient | |
| Compound of Example 37 | 200 |
| Excipient | |
| Microcrystalline cellulose | 45 |
| Lubricant | |
| Talc | 15 |
| Coating agent | |
| Hydroxypropylmethylcellulose phthalate | 30 |
| Total | 290 |

The main ingredient, excipient and lubricant were mixed, and filled in No. 2 capsules. The capsules were then each coated with 30 mg of the coating agent to form enteric-coated capsules.

| FORMULATION EXAMPLE 4 | |
| --- | --- |
| Enteric-coated capsules | Weight per capsule (mg) |
| Main ingredient | |
| Compound of Example 37 | 200 |
| Excipient | |
| Microcrystalline cellulose | 30 |
| Binder | |
| Hydroxypropylcellulose | 10 |
| Lubricant | |
| Magnesium stearate | 5 |
| Talc | 15 |
| Coating agent | |
| Hydroxypropylmethylcellulose phthalate | 30 |
| Total | 290 |

The main ingredient, excipient, binder and magnesium stearate were mixed and granulated in the dry state. The granules were mixed with talc, and filled in No. 2 capsules. The capsules were then each coated with 30 mg of the coating agent to form enteric-coated capsules.

| FORMULATION EXAMPLE 5 | |
| --- | --- |
| Enteric-coated granules | Weight per 600 mg of granules (mg) |
| Main ingredient | |
| Compound of Example 37 | 200 |
| Excipient | |
| Microcrystalline cellulose | 50 |
| Lactose | 80 |
| Hardened oil | 40 |
| Binder | |
| Hydroxypropylcellulose | 30 |
| Coating agent | |
| Hydroxypropylmethylcellulose phthalate | 200 |
| Total | 600 |

Rod-like granules were prepared from the main ingredient, excipient and binder. The granules were coated with 200 mg (per 600 mg) of the coating agent to form enteric-coated granules.

| FORMULATION EXAMPLE 6 | |
| --- | --- |
| Enteric-coated granules | Weight per 600 mg of granules (mg) |
| Main ingredient | |
| Compound of Example 37 | 200 |
| Excipient | |
| Microcrystalline cellulose | 40 |
| Sucrose | 80 |
| Corn starch | 40 |
| Hardened oil | 20 |
| Binder | |
| Hydroxypropylcellulose | 20 |
| Coating agent | |
| Hydroxypropylmethylcellulose phthalate | 200 |
| Total | 600 |

Spherical granules were prepared from the main ingredient, excipient and binder, and then coated with 200 mg (per 600 mg) of the coating agent to form enteric-coated granules.

| FORMULATION EXAMPLE 7 | |
| --- | --- |
| Suppository (oily) | Weight per suppository (mg) |
| Main ingredient | |
| Compound of Example 38 | 200 |
| Base | |
| Hardened castor oil | 5 |
| Witepsol H-15 | 1145 |
| Total | 1350 |

The bases were melted by heating, and the main ingredient was added. The mixture was stirred and dispersed and injected into containers, and cooled to form suppositories.

| FORMULATION EXAMPLE 8 | |
| --- | --- |
| Suppository (rectal capsule) | Weight per suppository (mg) |
| Main ingredient | |
| Compound of Example 38 | 200 |
| Base | |
| Hardened castor oil | 10 |
| Polyethylene glycol monostearate | 20 |
| Miglyol 810 | 730 |
| Total | 960 |

The above ingredients were well stirred and dispersed, and injected into rectal capsules to form suppositories.

FORMULATION EXAMPLE 9

| Suppository (water soluble) | Weight per suppository (mg) |
|---|---|
| Main ingredient | |
| Compound of Example 38 | 200 |
| Base | |
| Polyethylene glycol 400 | 100 |
| Polyethylene glycol 4000 | 1200 |
| Total | 1500 |

The bases were melted by heating, and the main ingredient was added. The mixture was stirred and dispersed, injected into containers, and cooled to form suppositories.

What is claimed is:

1. An aminoglycoside compound represented by the following formula (I)

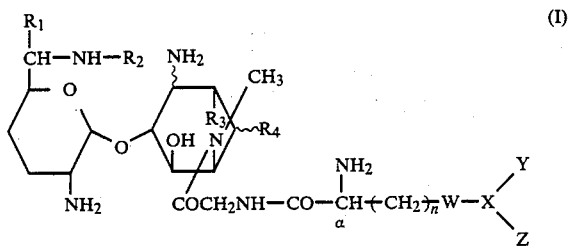

wherein
one of $R_1$ and $R_2$ represents a hydrogen atom, and the other represents a methyl group,
$R_3$ represents a hydrogen atom or a hydroxyl group,
$R_4$ represents a hydrogen atom, a hydroxyl group or a methoxy group,
n represents an integer of 1 to 5,
W represents a divalent group of the formula —NHCO→, —CONH→, —COO→, or —S→ in which → represents a bond to X, and X represents (i) a single bond or (ii) a $C_1$–$C_{20}$ trivalent acyclic saturated hydrocarbon group, with the proviso that
when X represents a single bond (i), the group —Z is absent in the formula, and Y represents a $C_6$–$C_{10}$ aryl group, a 3,12-dihydroxy-24-nor-cholan-23-yl group, the group —O—$Q^1$ or the group —CO—$Q^1$ in which $Q^1$ represents a $C_1$–$C_9$ alkyl group, and that when X represents a $C_1$–$C_{20}$ trivalent acyclic saturated hydrocarbon group (ii), the groups Z and Y, independently from each other, represent a hydrogen atom, a hydroxyl group, a carboxyl group, the group —COO$Q^1$ in which $Q^1$ is as defined, a phenyl group unsubstituted or substituted by lower alkoxy or nitro, a pyridyl group, a phenyl($C_1$–$C_3$)alkyl group, the group —O—$Q^1$ in which $Q^1$ is as defined, the group –(CH$_2$)$_j$O—OCQ$^2$, the group —CO—$Q^3$ or the group —CH$_2$)$_i$NHCOQ$^4$ in which $Q^2$ represents a 3,12-dihydroxy-24-nor-cholan-23-yl group, a 3,12-diacetoxy-24-nor-cholan-23-yl group, a $C_1$–$C_{20}$ alkyl group or a naphthyl group, $Q^3$ represents a $C_3$–$C_8$ alkylamino group, $Q^4$ represents a 3,12-dihydroxy-24-nor-cholan-23-yl group, a 3,12-diacetyloxy-24-nor-chlolan-23-yl group, a 3,12-dipropyloxy-24-nor-cholan-23-yl group or a $C_1$–$C_{25}$ alkyl group, and
l represents 0 or an integer of 1 to 6; or a pharmaceutically acceptable acid addition salt thereof.

2. A pharmaceutical composition comprising an antibiotically effective amount of the aminoglycoside of formula (I) or a pharmaceutically acceptable acid addition salt thereof as claimed in claim 1 and a pharmaceutically acceptable diluent or carrier.

3. The pharmaceutical composition of claim 2 wherein the amount of the aminoglycoside of formula (I) or its pharmaceutically acceptable acid addition salt is about 10 to about 90% by weight based on the weight of the composition.

4. The pharmaceutical composition of claim 2 which is as a formulation administrable through the digestive tract.

5. The pharmaceutical composition of claim 4 which is an orally administrable formulation.

6. The pharmaceutical composition of claim 4 which is as an intrarectally administrable formulation.

* * * * *